US012551652B2

(12) United States Patent
Zoellner et al.

(10) Patent No.: US 12,551,652 B2
(45) Date of Patent: Feb. 17, 2026

(54) SYSTEM AND METHOD FOR NON-INVASIVE VENTILATION

(71) Applicant: Fisher & Paykel Healthcare Limited, Auckland (NZ)

(72) Inventors: Sascha Kristopher Zoellner, Auckland (NZ); Bhavna Prentice, Auckland (NZ); Joseph Jules Nihotte, Auckland (NZ); Grant Leigh Nelson, Auckland (NZ); James Alexander Gordon, Auckland (NZ); Brendan O'Neill, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/636,960

(22) Filed: Apr. 16, 2024

(65) Prior Publication Data

US 2024/0307650 A1 Sep. 19, 2024

Related U.S. Application Data

(63) Continuation of application No. 17/040,007, filed as application No. PCT/IB2019/052329 on Mar. 22, 2019, now Pat. No. 12,337,118.

(Continued)

(51) Int. Cl.

*A61M 16/20* (2006.01)
*A61M 16/08* (2006.01)

(Continued)

(52) U.S. Cl.

CPC ...... *A61M 16/206* (2014.02); *A61M 16/0875* (2013.01); *A61M 16/0883* (2014.02);

(Continued)

(58) Field of Classification Search

CPC ............ A61M 16/206; A61M 16/0875; A61M 16/0883; A61M 16/1015; A61M 16/161;

(Continued)

(56) References Cited

U.S. PATENT DOCUMENTS 1,362,766 A 12/1920 Martin
5,005,571 A * 4/1991 Dietz .................... A61M 16/06 128/207.18

(Continued)

FOREIGN PATENT DOCUMENTS

WO WO 2009/017952 2/2009
WO 2013/067592 A1 5/2013

(Continued)

OTHER PUBLICATIONS

PCT Search Report for International Search Report for PCT/IB2019/052329 dated Jul. 22, 2019.

(Continued)

*Primary Examiner* — Brandy S Lee
*Assistant Examiner* — Tina Zhang
(74) *Attorney, Agent, or Firm* — Knobbe Martens Olson & Bear LLP

(57) ABSTRACT

Systems and methods for non-invasive ventilation are provided. The systems may include a gas source that provides breathing gases to a patient through one or more of a primary flow path (PFP) and a flushing flow path (FFP). The system may include a control assembly configured to open and restrict gas flow through the PFP. When the PFP is open, a significant portion of the gas flows through the PFP while the remaining gas flows through the FFP. When the PFP is restricted, a significant portion of the gas flows through the FFP. Increased flow through the FFP may have a high velocity (especially relative to the flow through the PFP). Gas delivered through the FFP may be used to flush dead (Continued)

space. One or both flow paths may contribute to inspiratory positive airway pressure (IPAP), expiratory positive airway pressure (EPAP), and/or positive end expiratory pressure (PEEP).

11 Claims, 33 Drawing Sheets

Related U.S. Application Data

(60) Provisional application No. 62/646,745, filed on Mar. 22, 2018.

(51) Int. Cl.
*A61M 16/10* (2006.01)
*A61M 16/16* (2006.01)

(52) U.S. Cl.
CPC ...... *A61M 16/1015* (2014.02); *A61M 16/161* (2014.02); *A61M 16/208* (2013.01); *A61M 2205/3334* (2013.01); *A61M 2205/3368* (2013.01)

(58) Field of Classification Search
CPC ........ A61M 16/208; A61M 2205/3334; A61M 2205/3368; A61M 16/201; A61M 16/0816; A61M 16/0866; A61M 16/0066; A61M 16/024; A61M 16/0858; A61M 16/16; A61M 16/204; A61M 2016/0027; A61M 2016/0039; A61M 2202/0225; A61M 2205/3344; A61M 2205/502; A61M 2210/1053; A61M 16/0833; A61M 16/0666; A61M 2205/3331; A61M 2210/0618; A61M 16/06; A61M 39/105; A61M 39/24; A61M 2039/246; A61M 16/0683; A61M 16/20; A61M 16/107; A61B 5/087; A61B 5/097; A62B 18/02; A62B 23/025
USPC ............ 128/205.25, 206.21, 207.18, 204.18, 128/205.24, 206.24, 204.23, 206.11, 128/206.15, 207.12, 206.28
See application file for complete search history.

(56) References Cited

U.S. PATENT DOCUMENTS

| | | | | |
|---|---|---|---|---|
| 5,460,174 | A * | 10/1995 | Chang .................... | A62B 9/022 128/205.24 |
| 6,253,767 | B1 | 7/2001 | Mantz | |
| 8,136,527 | B2 * | 3/2012 | Wondka ............ | A61M 16/0605 128/207.14 |
| 8,365,731 | B2 | 2/2013 | Ho | |
| 8,616,209 | B2 * | 12/2013 | Amarasinghe ...... | A61M 16/065 128/207.18 |
| 10,179,218 | B2 | 1/2019 | Ahmad | |
| 10,307,562 | B2 | 6/2019 | Cragg | |
| 2002/0096178 | A1 | 7/2002 | Ziaee | |
| 2002/0170557 | A1 * | 11/2002 | Schmidt ............ | A61M 15/0018 128/200.23 |
| 2004/0255948 | A1 | 12/2004 | Smith | |
| 2006/0112962 | A1 | 6/2006 | Tebbutt | |
| 2006/0201514 | A1 | 9/2006 | Jones et al. | |
| 2009/0032019 | A1 * | 2/2009 | Green ............... | A61M 15/0086 128/203.29 |
| 2009/0159084 | A1 | 6/2009 | Sher et al. | |
| 2011/0315143 | A1 * | 12/2011 | Frater ............... | A61M 16/0616 128/206.28 |
| 2015/0059759 | A1 * | 3/2015 | Frater ............... | A61M 16/0638 128/205.25 |
| 2015/0128941 | A1 | 5/2015 | Holley | |
| 2016/0136371 | A1 | 5/2016 | Rapoport | |
| 2016/0220781 | A1 | 8/2016 | Arrowsmith | |
| 2021/0016050 | A1 | 1/2021 | Zoellner et al. | |

FOREIGN PATENT DOCUMENTS

| | | |
|---|---|---|
| WO | WO 2013/171705 | 11/2013 |
| WO | WO 2015/041545 | 3/2015 |
| WO | WO 2016/157106 | 10/2016 |
| WO | WO 2017/096428 | 6/2017 |
| WO | 2018/033863 A1 | 2/2018 |
| WO | 2019/173869 A1 | 9/2019 |

OTHER PUBLICATIONS

Extended European Search Report for European Application No. 24164689.2 dated Aug. 20, 2024.

* cited by examiner

SYSTEM AND METHOD FOR NON-INVASIVE VENTILATION

BACKGROUND

Field

The application relates generally to systems and methods for non-invasive ventilation, and more specifically, relates to various control assemblies for controlling airflow and/or delivery to a patient interface and, ultimately, to a patient.

Description of the Related Art

Respiratory therapy systems are typically used for the treatment of respiratory conditions such as, for example, obstructive sleep apnea (OSA) or chronic obstructive pulmonary disease (COPD). Respiratory therapy systems typically deliver heated and humidified gases for various medical or therapy procedures, including respiratory treatment. Such systems can be configured to control temperature, humidity and flow rates.

Respiratory therapy systems generally include a gas source (such as a ventilator, a CPAP generator or other flow generator), a patient interface worn by a patient and a breathing circuit that connects the gas source to the patient interface. Respiratory therapy systems generally include an inspiratory flow path along which breathing gas is delivered from the gas source to the patient interface, and an expiratory flow path along which expiratory gas flows from the patient. The inspiratory and expiratory flow paths may be the same, but are typically different. The main components of the inspiratory path are commonly known as the inspiratory limb of the system, and typically comprise one or more sections of inspiratory gas delivery conduit and one or more connectors that connect the section(s) of conduit between the source of breathing gas and the patient interface. A humidifier may be included between the gas source and the breathing circuit to humidify the breathing gas.

One method of treating respiratory distress and certain respiratory disorders (including Chronic Obstructive Pulmonary Disease or COPD and Obstructive Sleep Apnea or OSA) is the provision of Continuous Positive Airway Pressure (CPAP) or other forms of positive airway pressure (PAP) to support a user's respiratory system. One form of PAP treatment is non-invasive respiratory pressurization or non-invasive ventilation (NIV) which is administered by delivering pressurized breathing gases to a user's mouth and/or nose.

Noninvasive ventilation therapy is a category of therapies that includes at least continuous positive airway pressure therapy (CPAP) and bi-level therapy positive airway pressure. Noninvasive ventilation (NIV) is used to improve alveolar gas exchange in patients with ventilation difficulty (e.g., Chronic Obstructive Pulmonary Disease (COPD)), pulmonary edema, obesity hypoventilation Syndrome (OHS), and other breathing related illnesses). Noninvasive ventilation, and in particularly bi-level therapy, may operate, at least in part, by providing pressure support to patients. The pressure may be beneficial to patients because it may increase tidal volume, recruit more alveoli, reduce the work of breathing, and splint airways open (which, in some patients, can be prone to collapsing). These benefits can result in improved alveolar gas exchange. CPAP delivers gas at a constant set pressure to a patient via a face mask that seals, or substantially seals, against the patient's face. Pressures delivered in CPAP therapy typically range from about 5-25 $cmH_2O$, but can go as high as about 40 $cmH_2O$. This therapy requires a flow source that controls the pressure delivered: examples of potential flow sources include, among others, CPAP generators, critical care ventilators, or a flow source with a PEEP valve (a valve that controls the maximum pressure in the system). Challenges to the success of CPAP therapies may include, among other things, user intolerance to patient interface pressures (manifested by, for example, localized pain and/or pressure sores) and poor patient compliance (which may be caused by elevated therapy pressures and its potential downstream effects).

Bi-level therapy delivers gases to a patient at two different set pressures, e.g., via a face mask that seals against the patients face. The two different pressures may be set to provide Inspiratory Positive Airway Pressure (IPAP) during the inspiration part of the breath cycle, and a lower Expiratory Positive Airway Pressure (EPAP) during the expiration part of the breath cycle. The difference between IPAP and EPAP is commonly referred to as the pressure support. Increasing the IPAP pressure or the pressure support (IPAP-EPAP) may advantageously improve alveolar gas exchange with noninvasive ventilation therapies. Typical pressures for IPAP range from about 8-25 $cmH_2O$, but can go as high as about 40 $cmH_2O$. Typical pressures for EPAP range from about 4-12 $cmH_2O$. Though, pressures for both IPAP and EPAP may vary considerably between clinician and patients. To provide this therapy, a more sophisticated flow source may be required as the flow source should actively synchronize with the patient's breathing cycle. Appropriate flow sources are generally Bi-level devices or critical care ventilators. Oxygen can also be advantageously, accurately delivered with these devices. In an acute setting, Bi-level may be used to treat patients with hypoxemia or hypercapnia (high levels of $CO_2$ in the blood). Challenges to the success of Bi-level therapy may include, among other things, user intolerance to patient interface pressures (manifested by, for example, localized pain and/or pressure sores), patient-ventilator asynchrony, and poor patient compliance (which may be caused by elevated therapy pressures and its potential downstream effects).

Although high therapy pressure is a primary mechanism by which noninvasive ventilation improves alveolar gas exchange for patients, it may require conditions that promote therapy failure. For example, ventilating at higher pressures demands more effective sealing of mask to the patient's face, which generally requires high headgear tension and leads to high forces being applied to the patient's skin. Over time, such high pressure may cause skin break down (pressure sores) which can lead to severe patient discomfort as well as penalties for the hospitals in some cases. The likelihood of gastric distention (gas build-up in the stomach), barotrauma and volutrauma (internal tissue damage caused by pressurized gas) may also be worsened by higher pressures. Ultimately, these side effects can often result in poor patient tolerance and failure of the therapy.

Conventional patient interfaces are configured to form a seal with the user's face or upper airway to facilitate adequate pressurization of the user's respiratory system. Eson™, Simplus™ and Nivairo™ are examples of sealing respiratory patient interfaces produced by Fisher & Paykel Healthcare Limited. Interfaces generally comprise a mask body and scaling cushion and are configured to seal with one or more of a user's face, mouth, nose, and nares. Typically the mask body is more rigid than the cushion, and may include a connector for connecting the interface to a gas delivery conduit. The connector can comprise an elbow connector which may, in turn, have a non-aligned inlet and outlet. The cushion is typically of a softer, more flexible material, such as silicone, foam and/or fabric, that, at least to some extent, molds to the shape of the user's face.

The seal formed between the interface and user's respiratory system allows the mask pressure to be regulated by reducing gas leaks and providing a controlled breathing gases exhaust. Gases may be exhausted from the patient interface directly to the surrounding atmosphere through outlet vents or to another component in the breathing assistance system responsible for controlling the exhaust of breathing gas.

SUMMARY

Systems and methods for non-invasive ventilation are provided. The systems may include a gas source that provides breathing gases to a patient through one or more of a primary flow path and a flushing flow path. The flushing flow path may have a higher resistance to flow than the primary flow path. The system may include a control assembly that is configured to open and restrict gas flow (for example, with a flow restrictor) through the primary flow path. When the primary flow path is open, a significant portion of the gas flow passes to the patient interface therethrough. When the primary flow path is open, a relatively small fraction of the gas flow passes through the flushing flow path. When the primary flow path is restricted, more of the gas flow, e.g., a significant portion, from the gas source passes through the flushing flow path. When a significant portion of the gas flow from the gas source passes through the flushing flow path, it may have a high velocity (in particular relative to the velocity of the gas flow through the primary flow path). Gas delivered through the flushing flow path may be used to flush dead space. One or both of the flow paths may contribute to at least one of inspiratory positive airway pressure (IPAP), expiratory positive airway pressure (EPAP), and positive end expiratory pressure (PEEP).

The control assembly may be located between the gas source and the patient interface. The control assembly may be provided in or form part of the primary flow path. The control assembly may be integrated in the patient interface and/or the gas source. The control assembly may have a gas source side and a patient interface side. The control assembly may be operable such that when the pressure on the gas source side of the control assembly is higher than pressure on the patient side of the control assembly, flow through the primary flow path is open or less restricted by the control assembly. Increased pressures on the gas source side relative to the patient interface side may correspond to decreased restriction of the primary flow path. The control assembly may be operable such that when pressure on the patient interface side of the control assembly is greater than the pressure on the gas source side of the control assembly, flow through the primary flow path is restricted or more restricted by the control assembly. Increased pressures on the patient interface side relative to the gas source side may correspond to increased restriction of the flow through the primary flow path. The control assembly may therefore be configured to vary the flow resistance of the primary flow path.

The control assembly may comprise a movable member such as a diaphragm(s) or flap(s). The movable member may be flexible. The movable member may form part of the primary flow path. The movable member may close over an opening (which may be an inlet opening) of the primary flow path. The movable member may have a gas source side and a patient interface side. The control assembly may comprise a housing in which the movable member is located and wherein the gas source side and patient interface side of the movable member are volumes within the housing. The movable member may be operable such that when the pressure on the gas source side of the movable member is higher than pressure on the patient side of the movable member, flow through the primary flow path is open or less restricted by the movable member. Greater pressures on the gas source side relative to the patient interface side may correspond to decreased restriction of the primary flow path. The movable member may be operable such that when pressure on the patient interface side of the movable member is greater than the pressure on the gas source side of the movable member, flow through the primary flow path is restricted or more restricted by the movable member. Greater pressures on the patient interface side relative to the gas source side may correspond to increased restriction of the primary flow path.

Disclosed herein is a system for providing respiratory gas to a patient, the system comprising: a patient interface; a breathing circuit to provide fluid communication between a source of respiratory gas and the patient interface, the breathing circuit and patient interface defining a primary flow path and a flushing flow path from the source of respiratory gas; and a control assembly configured to dynamically vary flow through the primary flow path by opening and restricting the primary flow path in response to dynamic changes in gas flow or resistance to gas flow, such that when the control assembly increases the restriction to flow through the primary flow path, flow of respiratory gas through the flushing flow path increases.

The system may comprise an exhaust vent for venting gas at a venting leak rate, and the exhaust vent may be configured to provide a venting leak rate greater than the patient exhaled gas flow rate.

The system may comprise an exhaust vent for venting gas from the system, and the control assembly may be configured to open and restrict flow through the exhaust vent such that when the control assembly increases the restriction to flow through the primary flow path, the control assembly decreases the restriction to flow through the exhaust vent.

The primary flow path may have a first resistance to gas flow, the flushing flow path may have a second higher resistance to gas flow, and the control assembly may be configured to increase the resistance to gas flow of the primary flow path in response to a pressure change within a breathing chamber of the patient interface.

The system may comprise the control assembly may be configured to increase the resistance of the primary flow path to gas flow when a pressure in the breathing chamber of the patient interface increases to substantially equal to or greater than about the gas source pressure.

Disclosed herein also is a system for non-invasive ventilation comprising: a gas source conduit adapted to be fluidly coupled at a first end to a gas source and comprising at a second end a bifurcation having a first branch and a second branch; a primary flow path conduit adapted to be coupled to the first branch of the bifurcation as part of a primary flow path; a flushing flow path conduit adapted to be coupled to the second branch of the bifurcation as part of a flushing flow path having a higher resistance to gas flow than primary flow path; a patient interface comprising a breathing chamber and a nasal flow delivery part, constructed such that the breathing chamber is in the primary flow path and the nasal flow delivery part is in the flushing flow path; and a control assembly coupled or adapted to be coupled to the primary flow path, the control assembly comprising a movable member movable between a first position in which the movable member increases the resistance to gas flow through the primary flow path and a second position in which the movable member does not increase the resistance to gas flow through the primary flow path, the movable member configured to move between the first position and the second position in response to pressure changes within the breathing chamber of the patient interface.

The movable member may be configured to move to the first position when gas pressure within the breathing chamber of the patient interface is greater than about a gas source pressure and move to the second position when gas pressure within the breathing chamber is less than or equal to about a gas source pressure.

The control assembly may also comprise a feedback port adapted to fluidly couple to the breathing chamber of the patient interface, and be configured to increase the resistance to gas flow of the primary flow path when a feedback pressure coupled from the breathing chamber to the control assembly is greater than about a gas source pressure.

The control assembly may also comprise a feedback port adapted to fluidly couple to the breathing chamber of the patient interface, and be configured to operate in response to a feedback pressure from the breathing chamber coupled to the control assembly.

The control assembly may also comprise a movable member. The movable member may comprise a flap valve. The movable member may comprise a diaphragm. The control assembly may comprise a primary flow port and a flushing flow port, and the movable member may be movable between a position in which the movable member opens the primary flow port and a position in which the movable member restricts the primary flow port. The primary flow port may surround flushing flow port or the flushing flow port may surround the primary flow port, and the movable member associated with the primary flow port. The movable member may be arranged to open when primary gas flow pressure on a gas source side of the movable member is higher than pressure on an opposite side of the movable member and to restrict the primary gas flow port when pressure on a patient side of the movable member is higher than primary gas flow pressure on the gas source side of the movable member.

Disclosed herein is a control assembly for a system for providing respiratory gas to a patient, the control assembly configured to be located between a source of respiratory gas and a patient interface, and comprising: a gas flow inlet; a primary flow outlet; a flushing flow outlet; and a movable member configured to operate in response to patient inspiration and expiration to restrict flow through the primary flow outlet, thereby also increasing flow of respiratory gas through the flushing flow outlet, on a pressure increase in the breathing chamber on patient expiration, and open gas flow through the primary flow outlet on patient inspiration. In embodiments the control assembly may incorporate elements as outlined above.

Disclosed herein is a system for providing respiratory gas to a patient, the system comprising: a patient interface; a source of respiratory gas; and a breathing circuit arranged to provide fluid communication between the source of respiratory gas and the patient interface, wherein the system defines a primary flow path and a flushing flow path and is configured to provide respiratory gas to a patient from the source of respiratory gas through the primary and flushing flow paths; and wherein the system also comprises: a control assembly configured to open and restrict flow through the primary flow path, wherein when the control assembly increases the restriction to flow through the primary flow path, the flow of respiratory gas through the flushing flow path increases.

The source of respiratory gas generates a flow of gases at a gas source pressure. The control assembly may be configured to restrict flow through the primary flow path in response to the pressure within a breathing chamber of the patient interface.

The control assembly may be configured to restrict flow through the primary flow path in response to the pressure within a breathing chamber of the patient interface relative to the gas source pressure.

The control assembly may be configured to restrict flow through the primary flow path in response to a difference between the pressure in a breathing chamber of the patient interface and the gas source pressure.

The restriction to flow applied by the control assembly to the primary flow path may be correlated to the difference between the pressure in a breathing chamber of the patient interface and the gas source pressure.

Disclosed herein is a control assembly for a system for providing respiratory gas to a patient, the control assembly configured to be located between a source of respiratory gas and a patient interface, the control assembly comprising: a portion of a primary flow path of the system; a portion of a flushing flow path of the system; and a moveable member configured to open and restrict flow through the primary flow path, wherein when the movable member increases the restriction to flow through the primary flow path, the flow of respiratory gas through the flushing flow path increases.

Disclosed herein is a system for providing respiratory gas to a patient, the system comprising: a patient interface; a source of respiratory gas; a breathing circuit arranged to provide fluid communication between the source of respiratory gas and the patient interface; and an exhaust vent for venting gas at a venting leak rate from the system, wherein the system is configured to provide, at least during patient exhalation, a flow of gas from the source of respiratory gas at a flow rate that is greater than the difference between the venting leak rate and the flow rate of gases exhaled by the patient, and the venting leak rate is greater than the flow rate of gases exhaled by the patient.

Disclosed herein is a system for providing respiratory gas to a patient, the system comprising: a patient interface; a source of respiratory gas; a breathing circuit arranged to provide fluid communication between the source of respiratory gas and the patient interface; and an exhaust vent for venting gas from the system, wherein the system defines a primary flow path and is configured to provide respiratory gas to a patient through the primary flow path from the source of respiratory gas; and wherein the system also comprises: a control assembly configured to open and restrict flow through the primary flow path and to open and restrict flow through the exhaust vent, wherein when the control assembly increases the restriction to flow through the primary flow path, the control assembly decreases the restriction to flow through the exhaust vent.

Disclosed herein is a control assembly for a system for providing respiratory gas to a patient, the control assembly configured to be located between a source of respiratory gas and a patient interface, the control assembly comprising: a portion of a primary flow path of the system; an exhaust vent for venting gas from the system; and a moveable member configured to open and restrict flow through the primary flow path and to open and restrict flow through the exhaust vent, wherein when the movable member increases the restriction to flow through the primary flow path, the control assembly decreases the restriction to flow through the exhaust vent.

Disclosed herein is a system for non-invasive ventilation comprising: a gas source configured to generate a flow of gases; a patient interface having a breathing chamber; a primary flow path fluidly coupled to both the gas source and the patient interface, the primary flow path having a first resistance to flow of gases; a flushing flow path fluidly coupled to both the gas source and the patient interface, the flushing flow path having a second resistance to flow of gases, the second resistance to flow of gases being higher than the first resistance to flow of gases; a control assembly configured to increase the resistance of the primary flow path in response to a pressure within the breathing chamber.

The control assembly may be configured to increase the resistance of the primary flow path to a third resistance. The second resistance (of the flushing flow path) may be higher than the resistance of the third resistance (of the primary flow path). The second resistance may be lower than the third resistance.

Disclosed herein is a system for non-invasive ventilation comprising: a gas source configured to generate a flow of gases; a patient interface having a breathing chamber; a primary flow path fluidly coupled to both the gas source and the patient interface, the primary flow path having a dynamic resistance to flow of gases; a flushing flow path fluidly coupled to both the gas source and the patient interface, the flushing flow path having a static resistance to flow of gases; a control assembly configured to increase the resistance of the primary flow path in response to a pressure within the breathing chamber.

Disclosed herein is a system for non-invasive ventilation comprising: a gas source configured to generate a flow of gases; a patient interface having a breathing chamber; a primary flow path fluidly coupled to both the gas source and the patient interface, the primary flow path having a dynamic resistance to flow of gases changeable between a higher dynamic resistance and a lower dynamic resistance; a flushing flow path fluidly coupled to both the gas source and the patient interface, the flushing flow path having a static resistance to flow of gases greater than at least the lower dynamic resistance of the primary flow path; a control assembly configured to increase the first dynamic resistance of the primary flow path in response to a pressure within the breathing chamber.

The gas source generates a flow of gases at a gas source pressure. The control assembly may be configured to alter the resistance of the primary flow path in response to the pressure within the breathing chamber relative to the gas source pressure.

The control assembly may be configured to alter the resistance of the primary flow path in response to a difference between the pressure in the breathing chamber and the gas source pressure.

The resistance applied by the control assembly to the primary flow path may be correlated to the difference between the pressure in the breathing chamber and the gas source pressure.

Disclosed herein is a system for non-invasive ventilation comprising: a gas source configured to generate a flow of gases at a gas source pressure; a patient interface having a breathing chamber; a primary flow path fluidly coupled to both the gas source and the patient interface, the primary flow path having a dynamic resistance to flow of gases changeable between a higher dynamic resistance and a lower dynamic resistance; a flushing flow path fluidly coupled to both the gas source and the patient interface, the flushing flow path having a static resistance to flow of gases greater than at least the lower dynamic resistance of the primary flow path; a control assembly configured to increase the first dynamic resistance of the primary flow path when a pressure in the breathing chamber is greater than about the gas source pressure.

Disclosed herein is a system for non-invasive ventilation comprising: a gas source configured to generate a flow of gases; a gas source conduit having a first end and a second end, wherein the first end of the gas source conduit is fluidly coupled to the gas source and the second end of the gas source conduit comprises a bifurcation having a first branch and a second branch; a primary flow path coupled to the first branch of the bifurcation, wherein the primary flow path comprises a first end and a second end and has a first resistance to gas flow; a flushing flow path coupled to the second branch of the bifurcation, wherein the flushing flow path comprises a first end and a second end and has a second resistance to gas flow greater than the first resistance to gas flow, wherein the first end of the flushing flow path is coupled to the second branch of the bifurcation; a control assembly coupled to the primary flow path, the control assembly comprising a movable member having and movable between a first position in which the movable member increases the resistance to gas flow through the primary flow path and a second position in which the movable member does not increase the resistance to gas flow through the primary flow path; a patient interface comprising a breathing chamber and a nasal delivery portion, wherein the breathing chamber is coupled to the second end of the primary flow path and the nasal delivery portion is coupled to the second end of the flushing flow path wherein the movable member moves between the first position and the second position in response to a pressure within the breathing chamber of the patient interface.

Disclosed herein is a system for non-invasive ventilation comprising: a gas source configured to generate a flow of gases at a gas source pressure; a gas source conduit having a first end and a second end, wherein the first end of the gas source conduit is fluidly coupled to the gas source and the second end of the gas source conduit comprises a bifurcation having a first branch and a second branch; a primary flow path coupled to the first branch of the bifurcation, wherein the primary flow path comprises a first end and a second end and has a dynamic first resistance to gas flow changeable between a higher dynamic resistance and a lower dynamic resistance; a flushing flow path coupled to the second branch of the bifurcation, wherein the flushing flow path comprises a first end and a second end and has a second static resistance to gas flow greater than at least the lower dynamic resistance to gas flow, wherein the first end of the flushing flow path is coupled to the second branch of the bifurcation; a control assembly coupled to the primary flow path, the control assembly comprising a movable member having and movable between a first position in which the primary flow path has the higher dynamic resistance and a second position in which the primary flow path has the lower dynamic resistance; a patient interface comprising a breathing chamber and a nasal delivery portion, wherein the breathing chamber is coupled to the second end of the primary flow path and the nasal delivery portion is coupled to the second end of the flushing flow path, wherein the movable member is configured to move to the first position when a pressure within the breathing chamber of the patient interface is greater than about the gas source pressure and move to the second position when the pressure within the breathing chamber of the patient interface is less than or equal to about the gas source pressure.

Disclosed herein is a system for non-invasive ventilation comprising: a gas source configured to generate a flow of gases having a gas source pressure; a patient interface having a breathing chamber and a nasal delivery portion; a primary flow path fluidly coupling the breathing chamber of the patient interface to the gas source and having a first resistance to flow; a flushing flow path fluidly coupling the nasal delivery portion of the patient interface to the gas source and having a second resistance to flow the second resistance to flow being greater than the first resistance to flow; a control assembly configured to dynamically change the resistance to flow of the primary flow path; a feedback arrangement fluidly coupling the breathing chamber of the patient interface to the control assembly, wherein the control assembly is configured to increase the resistance to flow of the primary flow path when a pressure communicated from the breathing chamber to the control assembly by the feedback arrangement is greater than about the gas source pressure.

Disclosed herein is a system for non-invasive ventilation comprising: a gas source configured to generate a flow of gases having a gas source pressure; a patient interface having a breathing chamber and a nasal delivery portion; a primary flow path fluidly coupling the breathing chamber of the patient interface to the gas source and having a dynamic first resistance to flow changeable between a higher dynamic resistance and a lower dynamic resistance; a flushing flow path fluidly coupling the nasal delivery portion of the patient interface to the gas source and having a static second resistance to flow greater than at least the lower dynamic resistance of the primary flow path; a control assembly configured to change the dynamic first resistance to flow of the primary flow path; a feedback arrangement fluidly coupling the breathing chamber of the patient interface to the control assembly, wherein the control assembly is configured to increase the dynamic first resistance to flow of the primary flow path when a pressure communicated from the breathing chamber to the control assembly by the feedback arrangement is greater than about the gas source pressure.

Disclosed herein is a system for non-invasive ventilation comprising: a gas source configured to generate a flow of gases; a gas source conduit having a first end and a second end, wherein the first end of the gas source conduit is fluidly coupled to the gas source and the second end of the gas source conduit comprises a bifurcation having a first branch and a second branch; a primary flow path coupled to the first branch of the bifurcation, wherein the primary flow path comprises a first end and a second end and a dynamic first resistance to gas flow changeable between a higher dynamic resistance and a lower dynamic resistance; a flushing flow path coupled to the second branch of the bifurcation, wherein the flushing flow path comprises a first end and a second end and second static resistance to gas flow greater than at least the lower dynamic resistance of the primary flow path, wherein the first end of the flushing flow path is coupled to the second branch of the bifurcation; a control assembly coupled to the primary flow path, the control assembly comprising a movable member having and movable between a first position in which the primary flow path has the higher dynamic resistance and a second position in which the primary flow path has the lower dynamic resistance; a patient interface comprising a breathing chamber coupled to the second end of the primary flow path and a nasal delivery portion coupled to the second end of the flushing flow path; a feedback arrangement fluidly coupling the control assembly to the breathing chamber of the patient interface, wherein the movable member is configured to move between the first position and the second position in response to a pressure communicated to the control assembly by the feedback arrangement.

Disclosed herein is a control assembly for a system for providing respiratory gas to a patient, the control assembly configured to be located between a gas source and a patient interface, the control assembly comprising: a portion of a primary flow path of the system, the primary flow path having a dynamic resistance to flow of gases; a portion of a flushing flow path of the system, the flushing flow path having a static resistance to flow of gases; and a moveable member having and movable between a first position in which the primary flow path has a higher dynamic resistance and a second position in which the primary flow path has a lower dynamic resistance.

Disclosed herein is a control assembly for a system for providing respiratory gas to a patient, the control assembly configured to be located between a gas source and a patient interface, the control assembly comprising: a portion of a primary flow path of the system; a portion of a flushing flow path of the system; and a movable member having and movable between a first position in which the movable member increases the resistance to gas flow through the primary flow path and a second position in which the movable member does not increase the resistance to gas flow through the primary flow path.

Disclosed herein is a patient interface for providing respiratory gas to a patient, incorporating any control assembly as outlined above.

Disclosed herein is a patient interface for providing respiratory gas to a patient, comprising: a frame and cushion defining a breathing chamber having a primary gas flow inlet to the breathing chamber; a nasal flow delivery part to deliver a separate nasal flushing gas flow; and flow control valving integral with the interface and dynamically responsive to patient inhalation and exhalation to limit primary gas flow and increase flushing gas flow when the patient exhales and enable primary gas flow and decrease flushing gas flow when the patient inhales.

Disclosed herein is a one way valve for a patient interface for providing respiratory gas to a patient, the system comprising a vent and a valve associated with the vent, the valve comprising an expanding gas flow control element. The one way valve may be incorporated in any system disclosed herein.

The gas flow control element may comprise a hollow interior for primary gas flow through the gas flow control element and may be within a valve body defining a gas flow space between the exterior of the expanding flow control element and an interior of the valve body, and be expandable under inspiration primary gas flow pressure, against the interior of the valve body to close or restrict the gas flow space.

The valve may also comprise a secondary flow control element between the expanding gas flow control element and a gas port into the valve, arranged to operate under patient expiration gas pressure to restrict the primary gas flow path through the hollow interior of the exhaust gas flow control element.

The valve may be configured as a one way exhaust valve, in which the vent is an exhaust vent, and the expanding gas flow control element is an expanding exhaust gas flow control element.

Disclosed herein is a patient interface comprising a one way valve as outlined above wherein the vent and valve associated with the vent are incorporated in a part of the patient interface.

Disclosed herein is a conduit comprising a one way valve as outlined above, adapted to be coupled to a patient interface, wherein the valve is incorporated in the conduit.

BRIEF DESCRIPTION OF THE DRAWINGS

FIG. 3A illustrates an interface incorporating a control assembly with the control assembly in a first configuration. FIG. 3B illustrates the interface of FIG. 3A with the control assembly in a second configuration. FIG. 3C illustrates an enlarged view of the control assembly in the configuration of FIG. 3A. FIG. 3D illustrates an enlarged view of the control assembly in the configuration of FIG. 3B.

FIG. 4A illustrates the patient interface from the patient side. FIG. 4B illustrates the patient interface from the front.

FIG. 5A illustrates a partial patient interface and control assembly from the patient side. FIG. 5B illustrates a cross-sectional, vertical or sagittal view of the partial patient interface and control assembly of FIG. 5A.

FIG. 6A illustrates the control assembly of FIGS. 5A-5B in a first configuration. FIG. 6B illustrates the partial control assembly of FIGS. 5A-5B in a second configuration.

FIGS. 7A-7C show various views of a first embodiment of a valve. FIGS. 7D-7E show various views of a second embodiment of a valve.

FIGS. 7F-7G show various views of a third embodiment of a valve. FIGS. 7H-7I show various views of a fourth embodiment of a valve. FIGS. 7J-7K show various views of a fifth embodiment of a valve.

FIG. 9A illustrates the patient interface and a control assembly. FIG. 9B illustrates a side view of the patient interface only.

FIG. 11A illustrates the exterior of the control assembly, including various gas ports. FIG. 11B illustrates a three-quarter view of the control assembly partially disassembled. FIG. 11C illustrates a top view of the control assembly partially disassembled.

FIG. 12A shows a partially exploded view of the control assembly. FIG. 12B shows a longitudinal cross-section view of the control assembly. FIG. 12C shows a cut-away view of the control assembly.

FIG. 13A shows a partially exploded view of the control assembly. FIG. 13B shows a longitudinal cross-section view of the control assembly.

FIG. 14B shows the control assembly and patient interface of FIG. 14A in vertical cross-section and with the control assembly in a first operational configuration. FIG. 14C shows the control assembly and patient interface of FIG. 14A in vertical cross-section and with the control assembly in a second operational configuration.

FIG. 15A shows patient interface and control assembly from the front. FIG. 15B shows patient interface and control assembly from one side

FIGS. 17A-17B show the control assembly in longitudinal cross-section and in a first operational configuration. FIGS. 17C-17D show the control assembly in longitudinal cross-section and in a second operational configuration. FIG. 17E shows a ghost view of the control assembly.

FIG. 18A illustrates the control assembly in longitudinal cross-section and in a first operational configuration. FIG. 18B illustrates the control assembly in longitudinal cross-section and in a second operational configuration.

FIG. 19A shows the control assembly of FIGS. 18A-18C in a first operational configuration. FIG. 19B shows the control assembly of FIGS. 18A-18C in a second operational configuration.

FIG. 20A shows the control assembly in side view. FIG. 20B illustrates the control assembly in longitudinal cross-section and in a first operational configuration. FIG. 20C illustrates the control assembly in longitudinal cross-section and in a second operational configuration.

DETAILED DESCRIPTION

Figure 1:
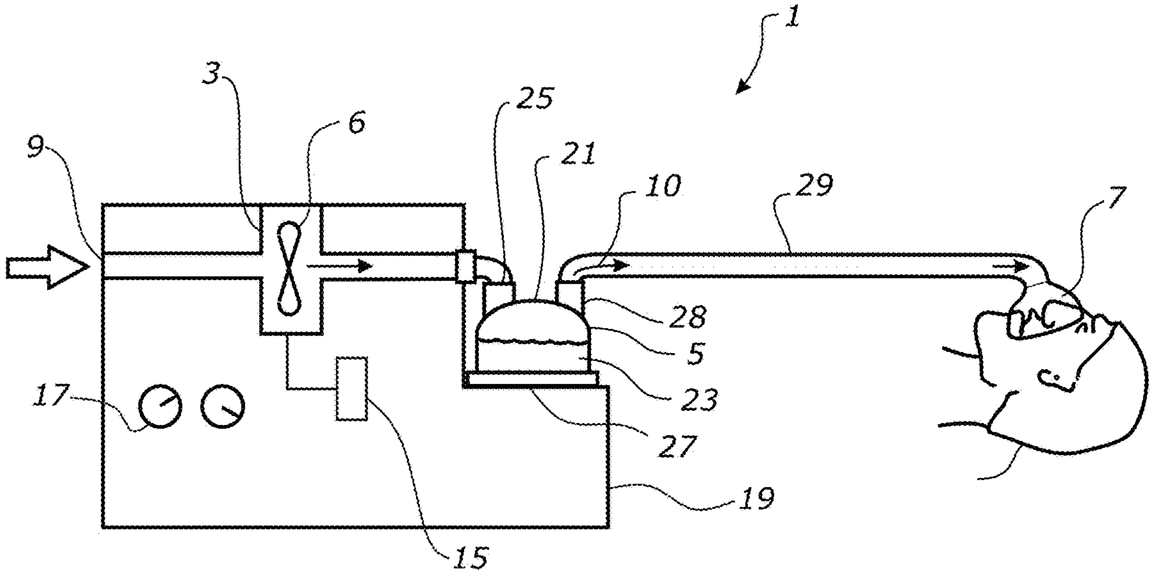
FIG. 1 is a schematic representation of a respiratory system configured to supply pressurized and humidified breathing gases to a user through a patient interface.

An example respiratory therapy system suitable for supplying breathing gases to a user for noninvasive ventilation therapy is illustrated in FIG. 1. The example respiratory therapy system 1 may include a gas source 3, a humidifier 5, a patient interface 7 and a breathing gas circuit 29 that connects the humidifier (or gas source) to the patient interface 7. The gas source 3 can provide a supply of breathing gas to the humidifier 5. The gas source could comprise a source of supplementary breathing gas, such as pressurized supplementary oxygen, as might be provided in a hospital environment for example. The gas source may alternatively or additionally comprise a blower in which breathing gas, e.g., ambient air, is drawn into the gas source 3 through an inlet 9 in the gas source casing by an impeller 11. The rotational speed of the impeller 11 may be modulated to regulate the quantity of air drawn into the gas source 3 and the supply of breathing gas delivered to the respiratory therapy system. Breathing gas may include any single gas or multiple gases that are breathable by a user of the system 1.

The pressure and/or flow rate of breathing gas exiting the gas source 3 may be regulated by a controller 15. The controller 15 may modulate the rotational speed of the impeller 11 according to one or more predetermined algorithms and in accordance with one or more user inputs that may be provided via a user input 17.

The gas source 3 represents an actively controlled flow generator. Other gas sources, such as a compressed air cylinder with suitable pressure or flow regulation, may also be used to supply breathing gas. The outlet of the gas source 3 may be coupled to a separate humidifier 5. The humidifier 5 may be configured to heat and/or humidify the breathing gas prior to delivery, e.g., delivery to the user. In some embodiments, the humidifier is integrated with the gas supply. The humidifier 5 may include a base 19 and a humidifier chamber 21. The chamber 21 may be configured to hold humidification fluid 23, such as water, and may be disengaged, e.g., temporarily disengaged or permanently disengaged, from the humidifier base 19 to allow it to be filled or replaced. The humidifier 5 receives gases from the gas source 3 through chamber inlet 25. The humidifier base 19 can include a heater such as a heater plate 27. The chamber 21 rests on the heater plate 27 when engaged with the humidifier base 19. The heater plate 27 dissipates heat, e.g., heat generated by electrical resistance, to the chamber 21. The chamber 21 preferably has a heat conductive base to enable the heat generated by the heater plate 27 to pass efficiently to the humidification fluid 23. Controller 15 can also control the humidifier 5, and in particular the supply of electrical energy to the heater plate 27, to regulate any function of the humidifier 5, e.g., the temperature and humidity of the breathing gas supplied to the user.

The breathing gas can be supplied to the user via a chamber outlet 28 and the breathing gas circuit 29 in the form of a conduit which may incorporate a heating or warming element, e.g., a heater wire, to heat or warm (e.g., keep hot or warm) the breathing gases during transportation to the patient interface 7. The electrical energy supplied to the heater wire may be controlled by controller 15. The controller 15 may receive feedback from one or more sensors incorporated in a control network throughout the respiratory therapy system to monitor properties of the breathing gas, such as, but not limited to, pressure, flow, temperature, and/or humidity.

The patient interface 7 couples the user with the respiratory therapy system 1, such that gases, e.g., heated and humidified gases from the humidifier 5, may be delivered to the user's respiratory system. Breathing gases can be delivered to the user at, or near, optimal temperature and humidity (e.g., warmed and fully saturated with water vapor at temperatures of between 27 and 37° C.) as the gases are delivered to the user's nares and or mouth. Emulating the conditions within healthy adult lungs (37° C., 44 mg/L humidity) can help maintain healthy mucociliary function in users with respiratory disorders affecting secretion and for all patients humidifying the gas helps maintain comfort and compliance. A number of different patient interface styles may be used in the systems and methods disclosed herein.

FIG. 2 illustrates a block diagram of an embodiment of a system for providing and/or maintaining noninvasive ventilation. As shown, the noninvasive ventilation system 200 includes at least a gas source 210, a control assembly 220, a patient interface 230, a breathing circuit 235 that connects the gas source 210 to the patient interface 230, and an exhaust vent 270. The gas source 210 may be, for example, a ventilator, a CPAP generator, a flow generator or a pressurized cylinder of gas.

The patient interface 230 may couple the user with the noninvasive ventilation system 200, such that respiratory gases from the gas source 210 may be delivered to the user's respiratory system. In some embodiments, the patient interface 230 comprises a mask that seals or substantially seals to the user's face about their nose and/or mouth and a nasal delivery portion for delivering gas into at least one of the user's nares. The nasal delivery portion has at least one opening positioned close to or inside one or more nares of the user such that, in use, gas exiting the nasal delivery portion is directed into at least one of the user's nares. The nasal delivery portion may include a non-sealing nasal cannula comprising, for example, one or more nasal prongs configured to be inserted into one or more nare(s) of the user; one or more nasal pillows that at least partially seal with a respective nare of the user (e.g., one nasal prong is sealed against the nare into which it directs gases, while the other nasal prong does not seal against the nare into which it directs gases); one or more stems that extend towards, but not into a user's nare(s); or one or more openings or holes configured to direct gas flow towards and or into a user's nare(s). The nasal delivery portion may be enclosed between the user's face and the mask of the patient interface 230. In some embodiments, the nasal delivery portion is integrally formed with the mask. In some embodiments, the nasal delivery portion is connected (e.g., reversibly, removably, or fixedly), coupled (e.g., reversibly, removably, or fixedly), or otherwise attached (e.g., reversibly, removably, or fixedly) to the mask.

In some embodiments, the mask of the patient interface 230 is configured to seal to a patient's face, surrounding at least the nasal delivery portion. In some embodiments, the patient interface 230 has a single sealing portion, e.g., seal, that seals to the face around both the mouth and the nose. In some embodiments, the patient interface 230 has at least two sealing portions, e.g., one sealing portion that seals around the mouth and a second sealing portion that seals around the nose. In some embodiments, the mask incorporates a separate opening to the nasal delivery portion (e.g., the at least one opening of the nasal opening) for gas to flow to the patient from the gas source. The mask may define a breathing chamber such that the mask opening is an opening in the breathing chamber. Gas may flow into the breathing chamber from the breathing circuit through the mask opening. In use, the breathing chamber may be maintained at an elevated pressure, e.g., above atmospheric, in order to provide a non-invasive ventilation therapy to the patient. By sealing the mask to the patient's face around the nasal delivery portion, gas flow through either the mask opening or the nasal delivery portion that is not inhaled by the patient may remain (at least temporarily) in the breathing chamber to assist in maintaining therapy pressure.

References in this specification to a patient interface may include a patient interface comprising a full face mask sealing around the mouth and nose of the user, and/or a patient interface comprising a nasal mask covering only the nose of the user. FIGS. 2B-2E illustrate various different types of patient interfaces that may be used with one or more different systems and/or methods of therapy disclosed herein. FIG. 2B illustrates a full face interface 201 that includes a nasal cannula 202 and seals around the patient's nose and mouth, and is supplied with gas flow by conduit 203. FIG. 2C illustrates a total face interface 204 that includes a nasal cannula 202 and substantially or fully seals around the patient's face, including at least the patient's nose, mouth, and eyes. FIG. 2D illustrates a subnasal interface 205 that includes a nasal cannula 202 and seals around the patient's mouth and nares on the underside of the nose. FIG. 2E illustrates a nasal interface 206 that includes a nasal cannula and seals around only the nares of the patient. Where this specification refers to nasal cannula, it is to be appreciated that other forms of a nasal delivery portion as described elsewhere herein could be used.

The noninvasive ventilation system 200 may be configured so that the gas source 210 delivers respiratory gas to the patient via at least a flushing flow path 250 and a primary flow path 260. The control assembly 220 may be configured to control or modulate (e.g., increase, decrease, start, stop) gas flow to the patient through the primary flow path 260. By controlling the primary flow path 260, the control assembly may be configured to affect and therefore indirectly control gas flow to the patient interface 230 through the flushing flow path 250. The control assembly is schematically illustrated as being incorporated within the breathing circuit at a location between the patient interface and the gas source. However, as discussed elsewhere herein, the control assembly may be incorporated into the patient interface and/or the gas source.

In some embodiments, the flushing flow path 250 includes the nasal delivery portion of the patient interface 230 (e.g., the cannula or nasal prong(s) of the patient interface 230). In some embodiments, the primary flow path 260 includes the breathing chamber of the patient interface 230.

In some embodiments, the flow of gases through the flushing flow path 250, which may include the nasal delivery portion, is continuous and unidirectional. In some embodiments, the flow of gases through the flushing flow path 250, which may include the nasal delivery portion, is not continuous. In some embodiments, the flow of gases through the flushing flow path 250, which may include the nasal delivery portion, may constantly flush at least a portion of the patient interface 230 (e.g., a mask) and/or one or more anatomical dead spaces of expired gases. In some embodiments, the flow of gases through the flushing flow path 250, which may include the nasal delivery portion, does not constantly flush either the a portion of the patient interface 230 (e.g., a mask) or one or more anatomical dead spaces of expired gases. "Dead space" as used here refers to either or both apparatus dead space and anatomical dead space. Apparatus dead space refers to zones in any equipment of the system such as the mask and breathing circuit where the expired gases have not been completely cleared during exhalation and can be re-breathed again. Anatomical dead space includes areas in the nose, pharynx, trachea and bronchi where $CO_2$ levels can build up. The systems and methods disclosed herein may advantageously provide improved flushing of the anatomical and/or apparatus dead space.

Re-inhalation of $CO_2$ can be reduced by purging or flushing, e.g., continuously or intermittently, the user's nares and/or nasal cavity (or other anatomical or device dead spaces) with fresh gas, e.g., gas having a lower concentration of $CO_2$. Expired gases may be evacuated from the patient interface 230, e.g., through the exhaust vent 270. In some embodiments, the velocity of breathing gases delivered to the user through the nasal delivery portion increases and decreases dynamically due to one or more factors, including, for example, the pressure being provided by the gas source (which may be configured to cycle between a comparatively higher pressure and a comparatively lower pressure, e.g., to deliver an IPAP and an EPAP, or may be configured to deliver a constant pressure flow to the patent interface), the exhalation flow pressure generated by the patient when they exhale (which may be non-constant within a single breath and/or between different breaths), and/or the inhalation flow pressure generated by the patient when they inhale (which may be non-constant within a single breath and/or between different breaths). In some embodiments, the velocity of breathing gases delivered to the patient through the nasal delivery portion is controlled passively by the control assembly and may vary throughout a breathing cycle.

Breathing gases may be delivered, e.g., delivered to the patient interface, at a flow rate exceeding the patient's peak inspiratory flow requirements to ensure that expired gases are purged throughout one or more portions of the respiratory cycle (e.g., the entire respiratory cycle). Either or both of the delivery of breathing gases to the mask and exhaust of gases from the mask may be controlled, e.g., passively or actively, to regulate the pressure within the mask. In some embodiments, exhaust gas flow rates are regulated actively by a component within the breathing assistance system (e.g., by the gas supply device). In some embodiments, exhaust gas flow rates are regulated passively (e.g., by fixing the restriction to gas flow using variable or non-variable outlet vents (for example, bias vents). In some embodiments, exhaust gas flow rates are regulated by a combination of active and passive venting. In some embodiments, exhaust may be modulated (e.g., restricted or allowed) by a movable component of a control assembly. For example, a diaphragm of the control assembly may have a flow restricting position in which it restricts the primary flow path and allows flow through an exhaust flow path. The diaphragm of the control may have a less restricting position in which it allows flow through the primary flow path and restricts flow through the exhaust flow path.

Using the systems and methods disclosed herein, a patient's airway pressure can be regulated/modulated by manipulating one or more of the gas delivery flow rate supplied to the nasal delivery portion, the gas delivery flow rate supplied to the mask, and the outlet flow rate vented or exhausted from the mask. In some embodiments, the systems and methods disclosed herein are configured to generate and/or maintain Inspiratory Positive Airway Pressure (IPAP). In some embodiments, the systems and methods disclosed herein are configured to generate and/or maintain Expiratory Positive Airway Pressure (EPAP). In some embodiments, the systems and methods disclosed herein are configured to generate and/or maintain Positive End Expiratory Pressure (PEEP). A Positive End Expiratory Pressure (PEEP) can keep the airways and alveoli from collapsing at the end of expiration and also serve to reopen airways and alveoli that have already collapsed. PEEP can improve gas exchange (by way of decreased intra pulmonary shunt), reduce the resistance to airflow (by reducing flow resistance within the lungs), levels of oxygen and carbon dioxide also may improve, reducing the need for supplemental oxygen and the sensation of breathlessness by the patient. PEEP may also improve cardiac performance by increasing mean intra thoracic pressure. PEEP may be particularly advantageous in connection with the treatment of obstructive lung diseases and heart failure, including emphysema, bronchiectasis, chronic bronchitis, cystic fibrosis and pulmonary edema.

As is described herein, delivering high velocity flow at a sufficiently high volumetric flow rate (and flushing dead space) during one or more portions of respiration, e.g., exhalation only, may sufficiently improve patient gas exchange to enable or permit a reduction in of one or more of IPAP, EPAP, and PEEP, in noninvasive ventilation treatment(s). Alternatively, the amount of $CO_2$ in the dead space may be reduced and better gas exchange achieved at about the same pressure(s) as compared to conventional non-invasive ventilation systems. Therefore, better gas exchange at the same IPAP, EPAP and/or PEEP may be achieved using the embodiments disclosed herein. In some embodiments, the control assembly 220 is configured to control the flow of gases from the gas source 210 and thereby create a primary pressure flow and/or a high(er) velocity flow for flushing. In some embodiments, the control assembly 220 is configured to control the flow of gases from the gas source 210 to create a primary flow, e.g., a high pressure flow, which may be delivered through the primary flow path 260, in particular or preferentially during patient inhalation. In some embodiments, the control assembly 220 is configured to control the flow of gases from the gas source 210 to create a flushing flow, e.g., a high velocity flow, which may be delivered through the flushing flow path 250, in particular or preferentially during patient exhalation. In this manner, the control assembly 220 may be configured to create two flows having different characteristics from a single source, e.g., the gas source 210. The control assembly is configured to provide gas flow to the patient interface from a single gas source that is configured to maintain the required treatment pressure for the patient (e.g., at all times) while also flushing dead space. Some embodiments of the control assembly 220 disclosed herein provide passive control, e.g., passively controls the flow of gas received from the gas source 210 to split it into the flushing flow path 250 and the primary flow path 260.

One or more embodiments of the methods for noninvasive ventilation disclosed herein advantageously foster dead space flushing while maintaining the pressure required for noninvasive ventilation in a portion of a patient interface (e.g., in the mask of the patient interface) by including one or more of: directing flow into a portion of a patient interface (e.g., the nasal delivery portion, which may include a nasal cannula or prong(s)), maintaining flow into the portion of the patient interface (e.g., the nasal delivery portion, which may include a nasal cannula or prong(s)), or increasing and/or decreasing flow into a portion of the patient interface (e.g., the nasal delivery portion, which may include a nasal cannula or prong(s)) at/during appropriate times in the patient's breath cycle.

In some embodiments, the gas source 210 comprises a ventilator. In some embodiments, the gas source 210 is configured to provide a flow of gases at a rate of between about 1-240 L/min, between about 2.5-230 L/min, between about 5-220 L/min, between about 7.5-210 L/min, between about 10-200 L/min, between about 12.5-190 L/min, between about 15-180 L/min, between about 17.5-170 L/min, between about 20-160 L/min, between about 22.5-150 L/min, between about 25-140 L/min, between about 27.5-130 L/min, between about 30-120 L/min, between about 32.5-110 L/min, between about 35-100 L/min, between about 37.5-90 L/min, between about 40-80 L/min, between about 42.5-70 L/min, between about 45-60 L/min, or between about 47.5-50 L/min. In some embodiments, the gas source 210 is configured to provide a flow of gases at a rate of less than about 240 L/min, less than about 230 L/min, less than about 220 L/min, less than about 210 L/min, less than about 200 L/min, less than about 190 L/min, less than about 180 L/min, less than about 170 L/min, less than about 160 L/min, less than about 150 L/min, less than about 140 L/min, less than about 130 L/min, less than about 120 L/min, or less than about 110 L/min. In some embodiments, the gas source 210 is configured to provide a flow of gases at a rate of between about 1-100 L/min, between about 2.5-95 L/min, between about 5-90 L/min, between about 7.5-85 L/min, between about 10-80 L/min, between about 12.5-75 L/min, between about 15-70 L/min, between about 17.5-65 L/min, between about 20-60 L/min, between about 22.5-55 L/min, between about 25-50 L/min, between about 27.5-45 L/min, or between about 30-40 L/min. The gas source 210 may be configured to provide a flow of gases at a rate of less than about 100 L/min, less than about 95 L/min, less than about 90 L/min, less than about 85 L/min, less than about 80 L/min, less than about 75 L/min, less than about 70 L/min, less than about 65 L/min, less than about 60 L/min, less than about 55 L/min, less than about 50 L/min, less than about 45 L/min, less than about 40 L/min, less than about 35 L/min, less than about 30 L/min, less than about 25 L/min, less than about 20 L/min, less than about 15 L/min, less than about 10 L/min, or any other rate of flow that advantageously delivers therapy as disclosed herein (e.g., promotes dead space flushing of the user's nasal cavity and or delivery of pressure inducing or maintaining flow rates into the patient interface).

In some embodiments, the gas source 210 is configured to provide gases at a pressure of less than about 60 $cmH_2O$, less than about 55 $cmH_2O$, less than about 50 $cmH_2O$, less than about 45 $cmH_2O$, less than about 40 $cmH_2O$, less than about 35 $cmH_2O$, less than about 30 $cmH_2O$, less than about 25 $cmH_2O$, less than about 20 $cmH_2O$, less than about 15 $cmH_2O$, less than about 10 $cmH_2O$, or less than about 5 $cmH_2O$. In some embodiments, the gas source 210 is configured to provide a constant pressure, e.g., during user inhalation and user exhalation. In some embodiments, the gas source 210 is configured to provide gases at a first pressure during inhalation and at a second pressure, different from the first pressure, during exhalation. In some embodiments, during user inhalation the gas source 210 is configured to provide gases at a pressure of between about 5-40 $cmH_2O$, between about 6-38 $cmH_2O$, between about 7-36 $cmH_2O$, between about 8-34 $cmH_2O$, between about 9-32 $cmH_2O$, between about 10-30 $cmH_2O$, between about, 11-28 $cmH_2O$, between about 12-26 $cmH_2O$, between about 13-24 $cmH_2O$, between about 14-22 $cmH_2O$, between about 15-20 $cmH_2O$, between about 16-18 $cmH_2O$, between about 8-25 $cmH_2O$, or any other pressure that advantageously delivers therapy as disclosed herein (e.g., that generates or maintains IPAP during user inhalation). In some embodiments, during user exhalation the gas source 210 is configured to provide gases at a pressure of between about 0-16 $cmH_2O$, between about 1-15, $cmH_2O$, between about 2-14 $cmH_2O$, between about, 3-13 $cmH_2O$, between about 4-12 $cmH_2O$, between about 5-11 $cmH_2O$, between about, 6-10 $cmH_2O$, between about, 7-9 $cmH_2O$, or any other pressure that advantageously delivers therapy as disclosed herein (e.g., that generates or maintains EPAP during user exhalation). In some embodiments, the gas source 210 is configured to provide gases at a pressure sufficient to maintain PEEP.

The gas source 210 may be connected to the breathing circuit 235, e.g., by an outlet through which the gas source supplies breathing gas. The pressure and flow at the outlet of the gas source 210, e.g., of the gases leaving the gas source 210, may be at a first pressure, P1 and a first volumetric flow rate, F1. The gas source 210 may be controlled to provide a first pressure (P1) and first flow rate (F1) to achieve a desired pressure at the patient interface, e.g., in the breathing chamber of the mask. The first pressure (P1) and first flow rate (F1) may be controlled to account/compensate for losses, e.g., system pressure losses, between the gas source 210 and the patient interface 230. As mentioned, the pressure at the patient interface may vary during the user's respiration cycle (e.g., between an IPAP and an EPAP).

The breathing circuit 235 divides, bifurcates, or splits into the flushing flow path 250 and the primary flow path 260. Each of the flushing flow path 250 and the primary flow path 260 may have a separate outlet in the patient interface through which breathing gas may be delivered to the user. The pressure and flow at the outlet of the flushing flow path may be at a second pressure, P2, and a second volumetric flow rate, F2. The pressure and flow at the outlet of the primary flow path may be at a third pressure, P3, and a third volumetric flow rate, F3.

The control assembly 220 may define an inlet to the primary flow path 260, e.g., an inlet from the gas source 210. The flushing flow path 250 may be connected to the gas source 210 via a set flow path, e.g., a flow path that is not directly changed or modified by the control assembly 220. When the control assembly 220 restricts the primary flow path 260, one or more of the volume and velocity of gases flowing through the flushing flow path 250 may increase. The control assembly 220 may be configured to have both a gas source side and a patient interface side. The gas source side of the control assembly 220 may include an inlet to the control assembly. The patient interface side of the control assembly 220 may include an outlet for the primary flow path 260. The control assembly 220 may be configured to vary the resistance to flow of the primary flow path 260.

The control assembly 220 may be operable such that when the pressure on the gas source side of the control assembly (e.g., generally corresponding to P1 less any pressure losses between the gas source 210 and the control assembly 220) is higher than the pressure on the patient interface side of the control assembly 220 (generally corresponding to P3 plus any loss of pressure between the patient interface side of the control assembly and the outlet of the primary flow path), flow through the primary flow path 260 is open, unrestricted, or comparatively less restricted by the control assembly 220. The control assembly 220 may be configured to respond dynamically to the aforementioned pressure differential. For example, the amount of restriction provided by the control assembly 220 may be correlated to the size of the pressure differential. Greater pressure differentials between the gas source side and the patient interface side of the control assembly (with the gas source side being a higher pressure than the patient interface side) may correspond to lessened restriction of the primary flow path 260.

The control assembly 220 may also be operable such that when the pressure on the patient interface side of the control assembly 220 (generally corresponding to P3 plus any loss of pressure from the patient interface side of the control assembly and the outlet of the primary flow path) is higher than the pressure on the gas source side of the control assembly 220 (generally corresponding to P1 less any pressure losses between the gas source 210 and the control assembly 220), flow through the primary flow path 260 is closed, restricted, or comparatively more restricted by the control assembly 220. The control assembly 220 may be configured to respond dynamically to the aforementioned pressure differential. For example, the amount of restriction provided by the control assembly 220 may be correlated to the size of the pressure differential. Greater pressure differentials between the gas source side and the patient interface side of the control assembly (with the patient interface side being a higher pressure than the gas source side) may correspond to increased restriction of the primary flow path 260.

When the control assembly 220 restricts flow through the primary flow path 260, for the same pressure (P1) at the outlet of the gas source 210, the flow through the primary flow path 260 (F3) is reduced and the flow through the flushing flow path 250 (F2) is increased, e.g., by the volume (or approximately the volume) the flow through the primary flow path 260 was decreased. As the volumetric flow rate through the flushing flow path 250 (F2) is increased, the velocity of the gas flow through the flushing flow path 250 is also increased. The system may be configured so that the velocity and/or the volumetric flow rate of the gas flow through the flushing flow path 250 (F2) is sufficiently high for a sufficient duration of the patient's breathing cycle to achieve flushing of at least a portion of the anatomical and/or apparatus dead space. Similarly, when the control assembly 220 opens or lessens restriction to flow through the primary flow path 260, for the same pressure (P1) at the outlet of the gas source 210, the flow through the primary flow path 260 (F3) is increased and the flow through the flushing flow path 250 (F2) is decreased due to the lowered resistance to flow through the primary flow path. As the volumetric flow rate through the primary flow path 260 (F3) is increased, the velocity of the gas flow through the primary flow path 260 is also increased. However, as the resistance to flow of the primary flow path 260 when fully open or unrestricted may be comparatively less than the resistance to flow of the flushing flow path 250 when fully open or unrestricted, the increase in velocity of the gases flowing through the primary flow path 260 when fully open in comparatively less than the increase in velocity of the gases flowing through the flushing flow path 250 when the primary flow path is closed, restricted, or more restricted (e.g., when the control assembly closes or restricts the primary flow path 260).

An increase in pressure on the patient interface side of the control assembly 220 relative to the pressure on the gas source side of the control assembly 220 generally occurs during patient exhalation. This is because the patient is breathing out (exhaling) and adding mass to the fixed volume of gas in the patient interface 230 (e.g., the breathing chamber of the patient interface) and thus increasing the pressure P3 in the primary flow path 260, e.g., at the outlet of the primary flow path 260. During patient inhalation, the pressure on the patient interface side of the control assembly 220 is usually lowered relative to the pressure on the gas source side of the control assembly 220 because the patient is drawing air in (inhaling) and removing mass from the fixed volume of gas in the patient interface 230. The system 200 may be configured to provide flushing of at least a portion of the anatomical and/or apparatus dead space during exhalation and in at least some embodiments flushing is rarely, if at all provided during inhalation.

As the control assembly 220 restricts the flow through the primary flow path 260 (F3), localized back pressure on the gas flow at the gas source side of the control assembly 220 may increase. Hence, to further restrict the flow through the primary flow path 260 (F3), a higher pressure may be required on the patient interface side of the control assembly 220. Therefore, the control assembly 220 may not fully close/restrict (e.g., may not be capable of fully closing/restricting) the primary flow path 260. It also provides for smooth operation of the control assembly 220. That is, the control assembly 220 may provide a controlled and smooth restricting and unrestricting of flow through the primary flow path 260 and may not cause sudden and/or uncomfortable changes of flow to/for the patient through either the primary flow path 260 or the flushing flow path 250.

The pressures, flow rates, and/or flow velocities in the different parts or portions, e.g., flow paths, of the ventilator system may vary dynamically during use. For example, when the gas source 210 operates with different IPAP and EPAP pressures, the first pressure (P1) may cycle between different pressures (e.g., the first pressure (P1) may cycle between IPAP and EPAP pressures). The second pressure (P2) and second flow rate (F2) and third pressure (P3) and third flow rate (F3) in the flushing flow path 250 and primary flow path 250, respectively, may also vary due to variations in the first pressure (P1) and/or operation of the control assembly 220, which itself may vary depending on or in response to the patient's breathing patterns. In some embodiments, the flushing flow path 250 and the primary flow path 260 are configured to provide gases (e.g., to provide gases when the control assembly 220 is open, e.g., in a relatively unrestricted configuration, such as during user inhalation) at pressures sufficient to generate and/or maintain IPAP. In some embodiments, the primary flow path 260 substantially alone (e.g., with little, minimal, or substantially no contribution from the flushing flow path 250) is configured to provide gases (e.g., to provide gases when the control assembly 220 is open, e.g., in a relatively unrestricted configuration, such as during user inhalation) at pressures sufficient to generate and/or maintain IPAP. In some embodiments, the flushing flow path 250 and the primary flow path 260 are configured to provide gases (e.g., to provide gases when the control assembly 220 is closed, e.g., in a relatively restricted configuration, such as during user exhalation) at velocities sufficient to fully, substantially, and/or partially flush at least a portion of the user's anatomical dead space. In some embodiments, the flushing flow path 250 substantially alone (e.g., with little, minimal, or substantially no contribution from the primary flow path 260) is configured to provide gases (e.g., to provide gases when the control assembly 220 is closed, e.g., in a relatively restricted configuration, such as during user exhalation) at velocities and/or volumetric flow rates sufficient to fully, substantially, and/or partially flush at least a portion of the user's anatomical dead space. In some embodiments, one or both of the flushing flow path 250 and the primary flow path 260 are configured to provided gases at pressures sufficient to maintain PEEP.

The third pressure (P3) and third flow rate (F3) in the primary flow path 260 and the second pressure (P2) and second flow rate (F2) in the flushing flow path 250 are dependent on a number of factors, including, but not limited to, the first pressure (P1) and the first flow rate (F1) provided by the gas source 210, the restriction of flow provided by the flushing flow path 250, the length of the flushing flow path 250, the restriction of flow provided by the primary flow path 260, the length of the primary flow path 260, and the user inhalation and exhalation flow rates. The control assembly 220 may be configured to increase or decrease the resistance to flow of the primary flow path 260. By modifying the length of one or both of the flow paths or the resistance of one or both of the flow paths, the system may be tuned for uses in varying circumstances.

The flushing flow path 250 may have one or more characteristics that restrict or inhibit flow by comparison to the primary flow path 260. Therefore, unimpeded (e.g., unimpeded by the control assembly 220 or any other modulating component), a higher volume of breathing gas will proceed to the patient interface 230 through the primary flow path 260 than through the flushing flow path 250. That is to say, unimpeded, the first flow rate (F1) is greater than the third flow rate (F3) (the first flow is split into the second flow and third flow, and must therefore be greater), which is, in turn, greater than the second flow rate (F2). The sum of the second flow rate (F2) and the third flow rate (F3) is equal to the first flow rate (F1) less any leaks or other losses in the system between the gas source 210 and the outlets of the primary flow path 260 and the flushing flow path 250. In some embodiments, the sum of the second flow rate (F2) and the third flow rate (F3) is approximately equal to the first flow rate (F1). However, the second flow rate (F2) and the third flow rate (F3) may vary (e.g., upon action of the control assembly 220 or other modulating component(s) of the system).

The flushing flow path 250 can provide a flow path, e.g., a continuous or continuously-open flow path, from the gas source 210 to the nasal delivery portion associated with the patient interface 230. The flushing flow path 250 may have a higher resistance to flow than the primary flow path 260. Higher resistance to flow in the flushing flow path 250 may be due to a smaller cross-sectional area of at least a portion of the flushing flow path 250 relative to the cross-sectional area of the primary flow path 260. Thus, given equivalent flow rates, gas flowing through the flushing flow path 250 will have a higher velocity, e.g., a substantially higher velocity, than gas flowing through the primary flow path 260 (e.g., when the primary flow path 260 is unimpeded by the control assembly 220).

The primary flow path 260 can provide a flow path from the gas source 210 to the patient interface 230, e.g., a breathing chamber defined by the mask of the patient interface 230. Due to the flow rate that may pass through the primary flow path 260, the primary flow path 260 may be configured to contribute substantially to (e.g., generate and/or maintain) one or more of inspiratory positive airway pressure (IPAP), expiratory positive airway pressure (EPAP), and positive end expiratory pressure (PEEP).

The control assembly 220 may be configured to respond to changes, e.g., one or more of increases and decreases, in the pressure within the breathing chamber of the patient interface 230 (PPI). For example, the control assembly 220 may be configured to inhibit, or reduce, or stop flow in the primary flow path 260 when the pressure within the breathing chamber of the patient interface 230 (PPI) increases above a value (e.g., a dynamic value), which may be or correspond to the pressure on the gas source side of the control assembly 220 (which may correspond to the gas source pressure (P1) less any pressure losses in the system between the gas source and the control assembly). Pressure within the patient interface 230 may increase due to patient exhalation. Similarly, the control assembly 220 may be configured to encourage, or increase, or start flow in the primary flow path 260 when the pressure within the patient interface 230 (PPI) decreases below a value (e.g., a dynamic value), which may be or correspond to the pressure on the gas source side of the control assembly 220 (which may correspond to the gas source pressure (P1) less any pressure losses in the system between the gas source and the control assembly). Pressure within the patient interface 230 may decrease due to patient inhalation as the patient inhales a greater volume of air than is entering the mask. In some embodiments, the control assembly 220 is configured to respond to relative or comparative pressure values, e.g., one or more pressure(s) within the breathing chamber of the patient interface 230 (PPI) compared to the pressure(s) within another portion of the system, such as the first pressure (P1), the second pressure (P2), the third pressure (P3), or some combination of the first pressure (P1), second pressure (P2) and third pressure (P3). In some embodiments, the control assembly 220 operates passively, e.g., responds to system feedback or conditions, e.g., systemic or localized pressure changes.

Figure 2A:
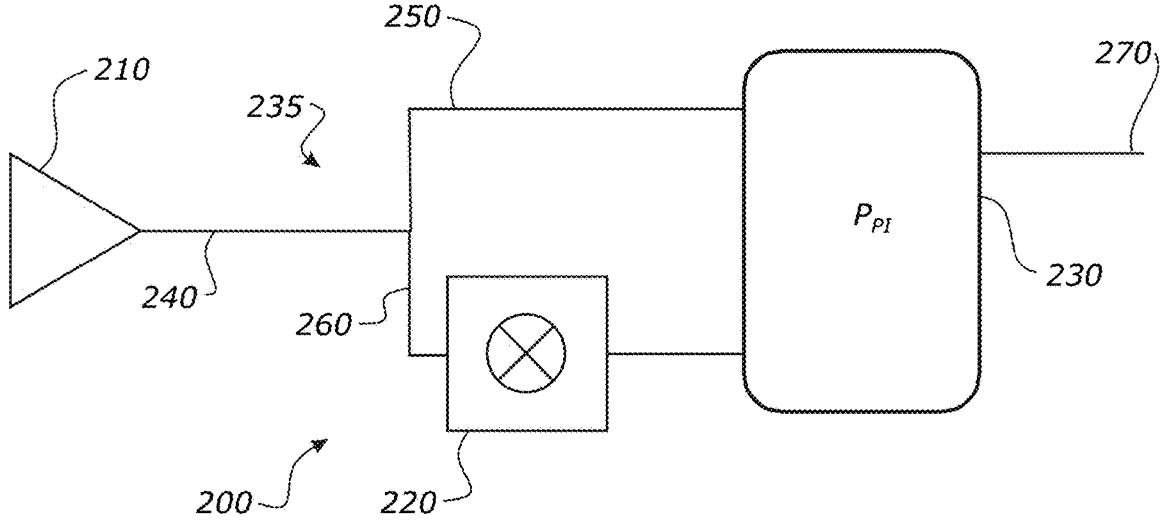
FIG. 2A is a block diagram of an embodiment of a system that may be used for noninvasive ventilation.
Figure 2B:
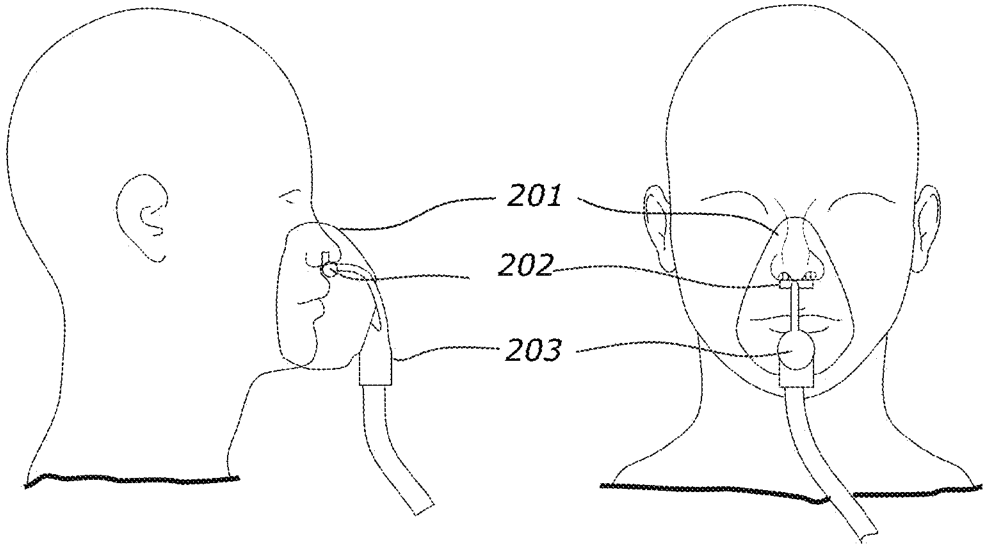
FIGS. 2B-2E illustrate various embodiments of patient interfaces, each in side and front view on a patient.
Figure 2C:
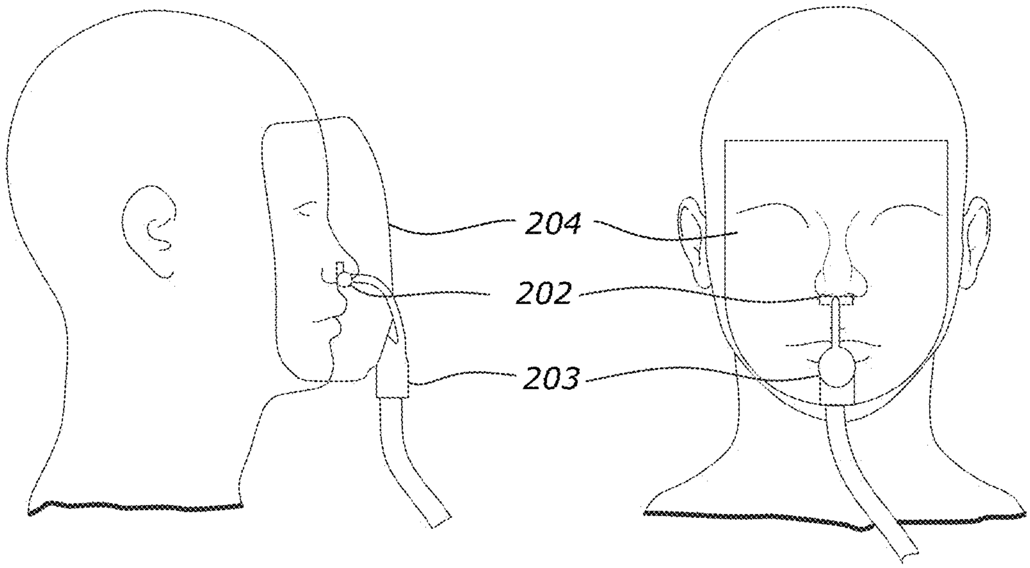
Figure 2D:
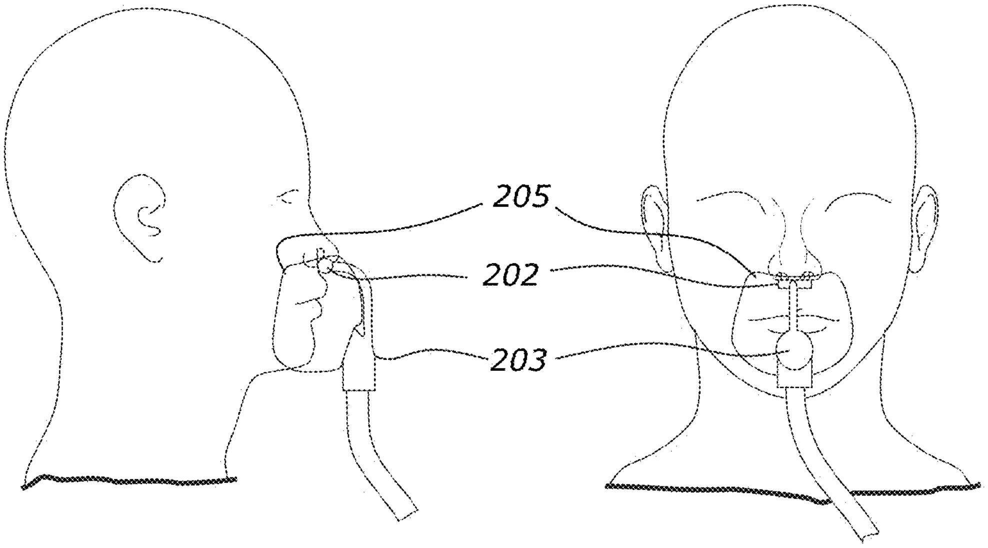
Figure 2E:
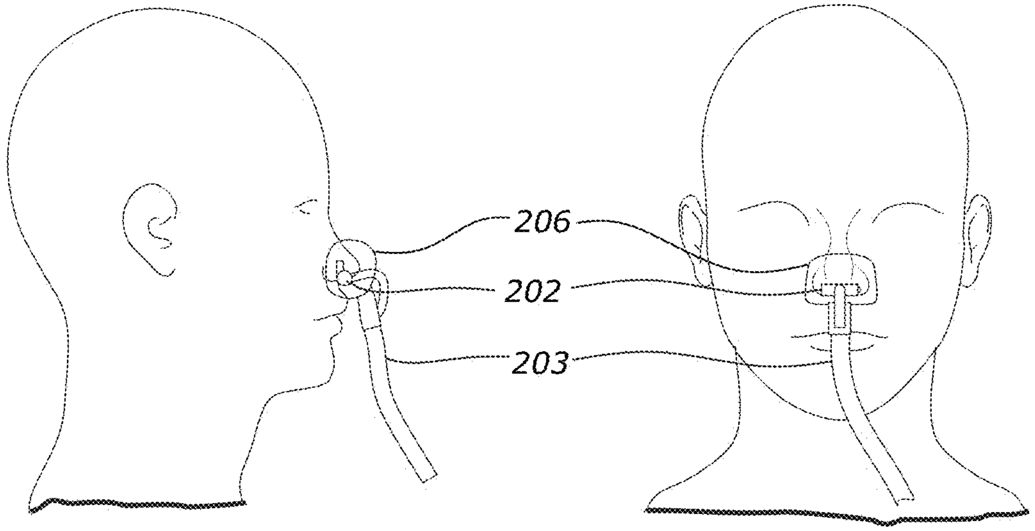

The delivery of breathing gases to the patient interface 230 of FIG. 2A may be determined based on a pressure balance. When the pressure within the breathing chamber of the patient interface 230 (PPI) is above a value (e.g., a dynamic value), which may be or correspond to the pressure on the gas source side of the control assembly 220 (which may correspond to the gas source pressure (P1) less any pressure losses in the system between the gas source and the control assembly) all, substantially all, most, or a substantial portion of the gas delivered to the patient interface 230 will be through the flushing flow path 250 because the control assembly 220 limits, inhibits, or diminishes flow through the primary flow path 260. When the pressure within the breathing chamber of the patient interface 230 (PPI) is equal to or below a value (e.g., a dynamic value), which may be or correspond to the pressure on the gas source side of the control assembly 220 (which may correspond to the gas source pressure (P1) less any pressure losses in the system between the gas source and the control assembly) gas will be delivered to the patient interface 230 through both the flushing flow path 250 and the primary flow path 260 because the control assembly 220 is not limiting, inhibiting, or diminishing (or is inhibiting or diminishing less) flow through the primary flow path 260. When flow through the primary flow path 260 is not being inhibited by the control assembly 220, the third gas flow rate (F3) through the primary flow path 260 is greater than the second gas flow rate (F2) through the flushing flow path 250, due to the higher resistance to flow of the flushing flow path 250 (or, stated alternatively, flow in the primary flow path 260 may be higher than flow in the flushing flow path 250 due to the primary flow path 260 having a lower resistance to flow than the flushing flow path 250).

In some embodiments, the control assembly 220 may be configured to close or substantially close or restrict flow through the primary flow path 260 when the pressure within the breathing chamber of the patient interface 230 (PPI) is greater than the first pressure (P1) at the outlet of the gas source 210 or the pressure within the gas source conduit 240. In some embodiments, the control assembly 220 may be configured to close or substantially close or restrict flow through the primary flow path 260 when the pressure within the breathing chamber of the patient interface 230 (PPI) is greater than the third pressure (P3) within the primary flow path 260 (e.g., the pressure in the primary flow path 260 on the gas source side of the control assembly).

The noninvasive ventilation system 200 may be balanced such that during patient inhalation, or at least a portion thereof, the pressure within the breathing chamber of the patient interface 230 (PPI) is equal to or less than a value (e.g., a dynamic value), which may be or correspond to the pressure on the gas source side of the control assembly (which may correspond to the gas source pressure P1 less any pressure losses in the system between the gas source and the control assembly). This is because during inhalation, the patient is drawing gas out of the breathing chamber. Thus, the control assembly 220 opens or remains open such that flow may pass unimpeded or substantially unimpeded through the primary flow path 260. When the control assembly 220 is open, flow may prefer the primary flow path 260 over the flushing flow path 250 because the primary flow path 260 may have a lower resistance to flow than the flushing flow path 250. Stated alternatively, the flushing flow path 250 may have a higher resistance to flow than the primary flow path 260; consequently, when the control assembly 220 is open, gases will flow through both the flushing flow path 250 and the primary flow path 260, but because of the higher resistance to flow of the flushing flow path 250 the gases will flow preferentially through the primary flow path 260. Thus, during inhalation, the control assembly 220 may substantially supply the patient with gas through the primary flow path 260. During inhalation, the primary flow path 260 may contribute substantially to (e.g., generate and/or maintain) IPAP.

Noninvasive ventilation systems have a venting arrangement to improve system performance. Venting is an intentional leak in the system, e.g., mask or patient interface, that allows gases, e.g., in particular, $CO_2$ rich gas, to escape from the breathing circuit. Conventional systems may typically vent up to around 20-50 Liters per minute at typical therapy pressures. However, patients generally exhale gases at about 30 Liters per minute. This means that in conventional systems (and assuming no significant unintentional leaks), 10 Liters per minute or more of exhaled gases ($CO_2$ rich) are expired into the patient interface and breathing circuit. As a result, on the next inhalation, the patient rebreathes this $CO_2$ rich gas and receives less than optimal gas exchange due to the lowered overall quality of the gas inhaled (e.g., the increased concentration of $CO_2$). In some embodiments of the non-invasive ventilation systems disclosed herein, the system is configured to vent at a higher volumetric flow rate than the patient's exhalation rate. In order to maintain EPAP, the first flow rate (F1) may be greater, e.g., marginally or slightly greater, than the difference between the venting leak rate and the flow rate of gases exhaled by the patient. Therefore, for example, if the exhaust vent 270 vents exhaust at about 50 Liters per minute, the gas source 210 may advantageously provide gases to the patient interface 230 at a flow rate (F1) of greater than about 20 Liters per minute (~30 L/min exhaled+~20 L/min flow=~50 L/m exhausted). Additionally, for example, if the exhaust vent 270 vents exhaust at a higher rate of about 70 Liters per minute, the gas source 210 may advantageously provide gases to the patient interface 230 at a flow rate (F1) of about 40 Liters per minute (~30 L/min exhaled+~40 L/min flow=~70 L/m exhausted). In some embodiments, the second flow rate (F2) of the flushing flow path may be greater, e.g., marginally or slightly greater, than the difference between the venting leak rate and the flow rate of gases exhaled by the patient. In this way, EPAP may be maintained. Venting may be provided on the patient interface 230, e.g., the patient mask, or the breathing circuit, or the gas source.

In some embodiments, the exhaust vent 270 is configured to vent exhaust gases, e.g., to the atmosphere, at least about 25 L/min, at least about 30 L/min, at least about 35 L/min, at least about 40 L/min, at least about 45 L/min, at least about 50 L/min, at least about 55 L/min, at least about 60 L/min, at least about 65 L/min, at least about 70 L/min, at least about 75 L/min, at least about 80 L/min.

In some embodiments, the exhaust vent 270 is passive and provides some resistance to venting, e.g., the exhaust vent 270 vents to the atmosphere as a function of pressure inside the patient interface 230. In some embodiments, the exhaust vent 270 provides active resistance to venting, e.g., the exhaust vent 270 vents to the atmosphere as a rate responsive to a sensor or other mechanism (e.g., vents faster or slower in response to sensor feedback). Therefore, upon exhalation, the pressure within the breathing chamber of the patient interface 230 (PPI) increases relative to the pressure of the flow (P1) from the gas source 210. The noninvasive ventilation system 200 may be balanced such that during patient exhalation, or at least a portion thereof, the pressure within the breathing chamber of the patient interface 230 (PPI) is greater than a value (e.g., a dynamic value), which may be or correspond to the pressure on the gas source side of the control assembly 220 (which may, in turn, correspond to the gas source pressure P1 less any pressure losses in the system between the gas source and the control assembly), and the control assembly 220 restricts flow through the primary flow path 260 such that flow through the primary flow path 260 is blocked or substantially blocked. When the flow through the primary flow path 260 is blocked or substantially blocked, a portion, e.g., a substantial portion, of the gas flow from the gas source 210 may be diverted through the flushing flow path 250 to the patient interface 230 (e.g., which may specifically include the nasal delivery portion of the patient interface 230, e.g., a nasal cannula and/or prong(s)). Thus, during exhalation, a portion of the gases supplied to the patient interface 230 are supplied with high velocity (a comparatively increased velocity) through the flushing flow path 250. Additionally, due to an advantageous balance of volumetric gas delivery and venting, an expiratory positive airway pressure may be maintained during exhalation.

Returning again to the balance of flow between the flushing flow path 250 and the primary flow path 260, as disclosed herein, the noninvasive ventilation system 200 may be balanced such that when both the flushing flow path 250 and the primary flow path 260 are unobstructed or substantially unobstructed, flow is biased to the primary flow path 260 due to resistance provided by the flushing flow path 250. Such higher resistance to flow may be due to a diameter of all or a portion of the flushing flow path 250 (e.g., a global restriction). Alternatively, higher resistance to flow may be due to one or more narrowings in the flushing flow path 250 (e.g., localized restrictions), for example, but not limited to, reduced cross-sectional area of one or more of a gas-carrying conduit of the flushing flow path 250 and the nasal delivery portion, e.g., nasal prongs or a nasal cannula. For example, in some embodiments the flushing flow path 250 restricts flow by employing a comparatively smaller diameter tubing. The restriction to flow provided by the flushing flow path 250 may be located anywhere between the terminal end of the flushing flow path 250 (e.g., where the flushing flow path 250 releases gas flow into the patient's nares) and the proximal end of the flushing flow path 250 (e.g., where the breathing circuit 235 (e.g., the gas source conduit 240) bifurcates into the flushing flow path 250 and the primary flow path 260.

The control assembly 220 may comprise a movable member such as a diaphragm, flap or flaps. The movable member may be flexible. The movable member may form part of the primary flow path 260. The movable member may close over or cover the inlet of the primary flow path 260. The movable member may have a gas source side and a patient interface side. The control assembly may comprise a housing in which the movable member is located or held (e.g., the gas source side and patient interface side of the movable member may define or divide first and second volumes within the housing). The first volume (e.g., on the gas source side of the movable member) may be located between the inlet of the control assembly 220 and the inlet of the primary flow path 260. The second volume (e.g., on the patient interface side of the movable member) may be located between the inlet of the primary flow path 260 and the control assembly outlet for the primary flow path.

In some embodiments, the control assembly 220 is operable such that when the pressure on the gas source side of the movable member (generally corresponding to P1 less any pressure losses between the gas source outlet and the movable member) is greater than the pressure on the patient side of the movable member (generally corresponding to P3 plus any loss of pressure from the patient interface side of the movable member and the outlet of the primary flow path), the movable member decreases resistance to flow through the primary flow path 260. In some embodiments, the greater the pressure differential between the gas source side and the patient interface side of the movable member (with pressure on the gas source side being higher than on the patient interface side), the less restricted the primary flow path 260 will be.

In some embodiments, the control assembly is operable such that when the pressure on the patient interface side of the movable member (generally corresponding to P3 plus any loss of pressure from the patient interface side of the movable member and the outlet of the primary flow path) is greater than the pressure on the gas source side of the movable member (generally corresponding to P1 less any pressure losses between the gas source outlet and the movable member), the movable member increases resistance to flow through the primary flow path 260. In some embodiments, the greater the positive pressure differential between the patient interface side and the gas source side of the moveable member (with pressure on the patient interface side being higher than pressure on the interface side), the more restricted the flow through the primary flow path 260 will be.

Figure 3A:
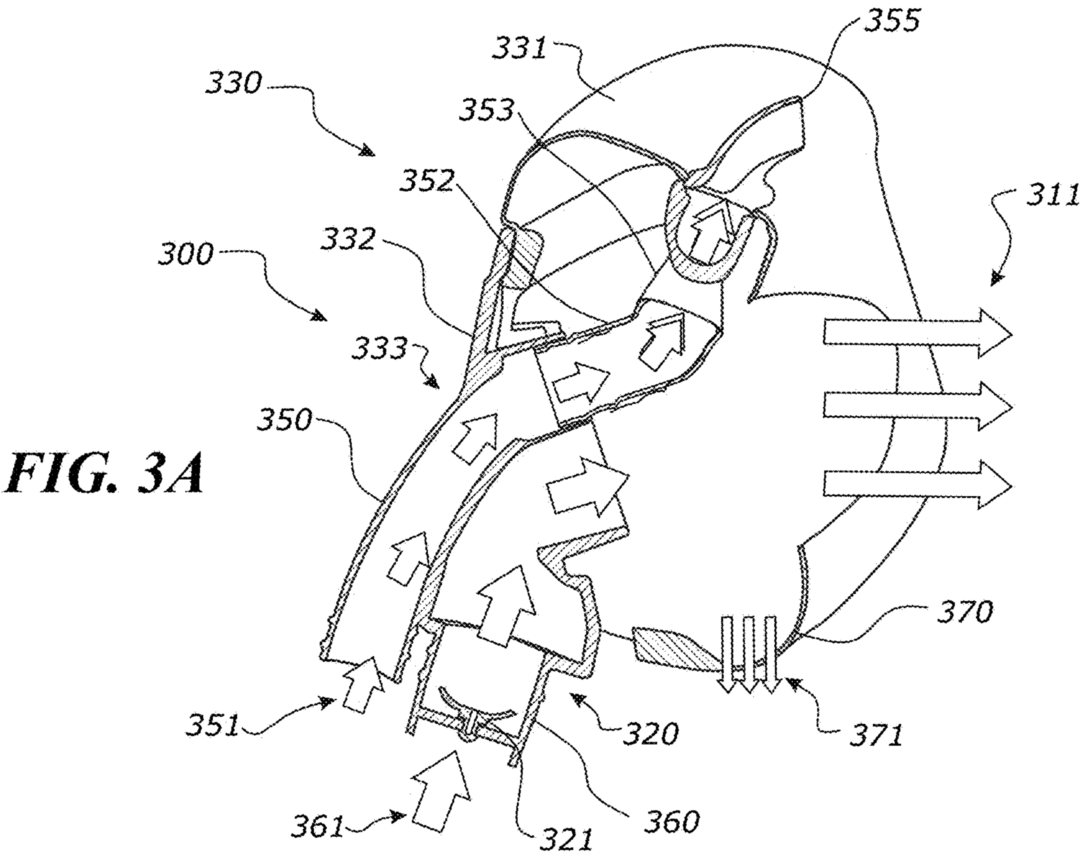
FIGS. 3A-3D are vertical cross-sectional views of a portion of an embodiment of a system that may be used for noninvasive ventilation, the portion of the system including at least a patient interface and a control assembly.
Figure 3B:
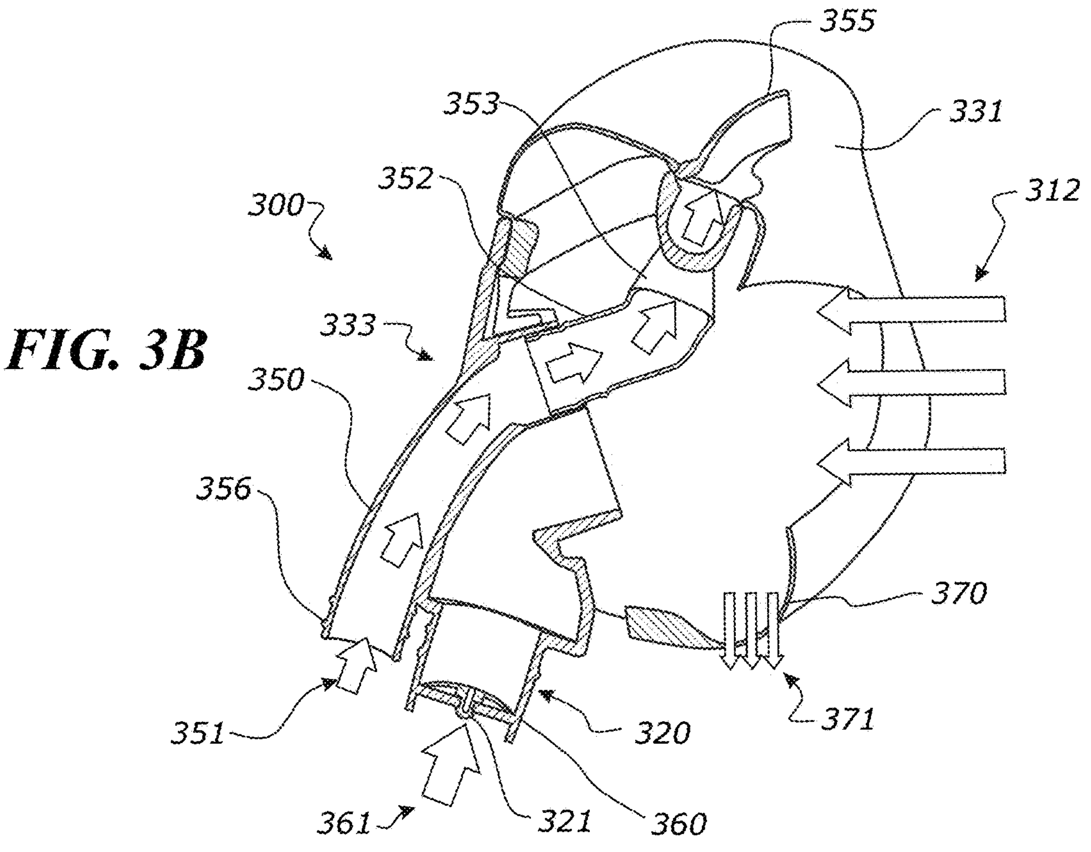

FIGS. 3A-3B illustrate select portions of an embodiment of a system for noninvasive ventilation. As will be discussed in greater depth, FIG. 3A illustrates the system while a patient (not pictured) is inhaling, and FIG. 3B illustrates the system while the patient is exhaling. The embodiment shown in FIGS. 3A-3B operates, at least partially, using the principles discussed in connection with the more generic system of FIG. 2A (e.g., the embodiment shown in FIGS. 3A-3B may be a more specific embodiment of at least select principles disclosed in connection with the diagram of FIG. 2A).

FIG. 3A shows a non-invasive ventilation system 300 that incorporates a patient interface 330, a flushing flow path 350, a primary flow path 360, and a control assembly 320 comprising a flap valve in the form of an umbrella valve 321. The patient interface 330 may comprise a mask body 332 and a mask cushion 331. The mask body 332 may be formed from a rigid or semi-rigid material, such as a plastic. The edge(s) of the mask body 332 may be surrounded by a mask cushion 331. The mask cushion 331 may be relatively soft and flexible and may be configured, by one or more of shape and material selection, to conform to the user's face while in use and thereby discourage, reduce, or eliminate uncontrolled leaking of the gas in the non-invasive ventilation system 300 out of the patient interface 330, e.g., from between the user's face (or portion thereof) and the mask cushion 331. The mask body 332 and mask cushion 331 together define a breathing chamber of the patient interface 330. The non-invasive ventilation system 300 may also include a flushing flow path 350 and a primary flow path 360.

The flushing flow path 350 comprises a conduit that enters the mask body 332 where it connects to a nasal elbow 353, which is connected via a nasal elbow fitting 352 to the mask body 332. The nasal elbow 353 terminates in one or more nasal prongs 355. The separate nasal elbow 353 may be omitted (also, thereby, omitting the nasal elbow fitting 352) and instead the flushing flow path 350 may comprise a conduit extending through the mask body 332, and up to the nasal prongs 355. The nasal elbow fitting 352 between the nasal elbow 353 and the mask body 332 substantially seals the gas flow between the conduit and the nasal elbow 353. The nasal coupling could form an interference or friction fit with the conduit, or the coupling could comprise a positive engagement mechanism, such as a snap-fit type mechanism. In some embodiments, the nasal elbow fitting 352 allows some degree of rotation of the nasal elbow 353, and therefore the nasal prongs 355, with respect to the flushing flow path 350 and the mask body 332. Rotation of the nasal elbow 353 and the nasal prongs 355 may improve user fit and/or comfort as the nasal prongs 355 may move with respect to one or more of the mask cushion 331 and the mask body 332 to accommodate different sizes, positions, etc. of patient nares.

The nasal elbow 353 and nasal prongs 355 may be configured to guide gas flow received from a gas source, such as a ventilator, to the patient's nares, e.g., the flushing gas flow 351. In some embodiments, the one or more nasal prongs 355 do not seal with the nares of the patient. In this way, the nasal cavity of the patient is always in fluid communication with the interior of the patient interface 330, in particular the breathing chamber. Because the nasal cavity of the patient is in fluid communication with the breathing chamber, safety and functionality may be promoted. First, communication between the nasal cavity and the breathing chamber allows the venting of gases from within the patient's nasal cavity even were the patient's mouth to close (e.g., rather than building up uncomfortable or unsafe pressures within the nasal cavity or any other anatomical structure). Second, communication between the nasal cavity and the breathing chamber allows flushing of the nasal cavity to diminish and/or eliminate anatomical dead space. Also, communication between the nasal cavity and the breathing chamber of the patient interface 230 may enable the flushing flow path 350 to provide or contribute to one or more of inspiratory positive airway pressure (IPAP), expiratory positive airway pressure (EPAP), and positive end expiratory pressure (PEEP).

In some embodiments, the nasal prongs 355 are configured to limit flow, e.g., limit the flushing gas flow 351 flowing through the flushing flow path 350. For example, in some embodiments, the nasal prongs 355 are configured to limit the flushing gas flow 351 to less than about 60 L/min, less than about 55 L/min, less than about 50 L/min, less than about 45 L/min, less than about 40 L/min, less than about 35 L/min, less than about 30 L/min, less than about 25 L/min, less than about 20 L/min, or less than about 15 L/min, less than about 10 L/min, less than about 5 L/min, or any other flow rate sufficient to flush or partially flush an anatomical dead space (e.g., the nasal cavity) of the patient. The nasal prongs 355 may limit the flushing gas flow due to a decreased cross-sectional diameter. The restriction to flow of the flushing gas flow through the flushing flow path 250 provided by the nasal prongs 355 may also serve to increase the velocity of the flushing gas flow. For example, the velocity of the flushing gas flow exiting the flushing flow path 250 when the control assembly 320 is restricting the primary flow path 360 is comparatively greater than the velocity of the flushing gas flow exiting the flushing flow path 350 when the control assembly 320 is not restricting the primary flow path. The volume and velocity of the flushing gas flow may be sufficiently large so as to flush at least a portion of one or more of an anatomical and an apparatus dead space.

In some embodiments, the flushing flow path 350, e.g., the nasal prongs 355, is configured to accelerate (e.g., increase the velocity) the flushing gas flow 351. Providing a significant volumetric flow rate of gas flow through the flushing flow path 350 may serve to accelerate the flushing gas flow 351 exiting the flushing flow path 350 (e.g., out of the nasal prongs 355) such that it may flush or partially flush an anatomical dead space (e.g., the nasal cavity) of the patient. In some embodiments, a decreased/reduced cross-sectional dimension, e.g., diameter or area, of at least one of the flushing flow path 350 and the nasal prongs 355 accelerates the flushing gas flow 351 exiting the flushing flow path 350. Increased velocity of the flushing gas flow 351 leaving the nasal prongs 355 may correlate (up to a limit) with increased efficiency of anatomical dead space flushing.

The primary flow path 360 may enter the mask body 332 at any location convenient for the delivery of a substantial volume of gas into the patient interface 330 and to the patient. In some embodiments, the primary flow path 360 is configured such that it provides or contributes to one or more of inspiratory positive airway pressure (IPAP), expiratory positive airway pressure (EPAP), and positive end expiratory pressure (PEEP). The mask body 332 may include a coupling portion 333 that allows one or more conduits of a breathing circuit, e.g., primary flow path 360 and/or flushing flow path 350, to fluidly couple the patient interface 330 to a gas source, e.g., a ventilator. In the embodiment shown in FIGS. 3A and 3B separate conduits for the primary flow path 360 and flushing flow path 350 couple to the coupling portion of the mask body 330.

In the non-invasive ventilation system 300 of FIGS. 3A-3B a control assembly 320 is contained in-line with the primary flow path 360. The control assembly 320 may be housed within the primary flow path 360 of the breathing circuit. As shown enlarged in FIGS. 3C-3D, the control assembly 320 comprises an umbrella valve 321 held within the primary flow path 360. The umbrella valve 321 comprises a generally circular flap 322 that is arranged to extend over one or more openings in the control assembly 320, e.g., openings between the gas source side of the control assembly 320 and the patient interface side of the control assembly 320. The flap 322 may be sufficiently flexible to enable at least portions of the flap 322 to move in response to differences in pressure on either side of the flap 322, e.g., the pressure on the gas source side of the control assembly 320 and the pressure on the patient interface side of the control assembly 320. The umbrella valve 321 may have a stem 323 extending from a central portion of the flap 322. The stem 323 is received in a mounting frame 324 of the control assembly 320 to hold and position the umbrella valve 321 in position. The mounting frame 324 extends between inner side walls of the primary flow path 360. The umbrella valve 321 of the control assembly 320 may be configured to allow substantially one way flow of gas, e.g., primary gas flow 361, through the primary flow path 360. FIG. 3A shows the umbrella valve 321 in a first state, e.g., an open state, in which the umbrella valve 321 of the control assembly 320 allows respiratory gas to flow through the primary flow path 360 and into the breathing chamber of the patient interface 330. FIG. 3B shows the umbrella valve 321 in a second state, e.g., a closed state, in which the umbrella valve 321 of the control assembly 320 closes or substantially closes (e.g., inhibits/restricts or substantially inhibits/restricts) to limit gas flow through the primary flow path 360. Therefore, when the umbrella valve 321 is in its second state (e.g., restricted state), less, e.g., significantly less respiratory gas passes through the primary flow path 360 into the breathing chamber of the patient interface 330. While a flap valve 321 is shown, other types of valves may be used.

The pressure within the breathing chamber of the patient interface 330 may change dynamically and the umbrella valve 321 may be configured to change states at appropriate times during a patient's breathing cycle (e.g., in response to pressures generated by the patient). The umbrella valve 321 of the control assembly 320 may be configured to change states, e.g., from the second state to the first state and/or from the first state to the second state, based on a characteristic of the ventilation system, e.g., a pressure within the breathing chamber of the patient interface 330 and/or a pressure of the primary gas flow 361. In some embodiments, the umbrella valve 321 of the control assembly 320 is configured to restrict the primary flow path 360 (e.g., inhibit, or reduce, or stop flow in the primary flow path 360) when the pressure on the patient interface side of the control assembly (e.g., which may be correlated with the pressure within the breathing chamber of the patient interface 330 (PPI)) increases above a value (e.g., a dynamic value), which may be or correlate to the pressure on the gas source side of the control assembly 320 (similar to the system disclosed in connection with FIG. 2A). In some embodiments, the umbrella valve 321 of the control assembly 320 is configured to open or maintain open the primary flow path 360 (e.g., lessen or minimize restriction of flow in the primary flow path 360) when the pressure on the patient interface side of the control assembly (e.g., which may be correlated with the pressure within the breathing chamber of the patient interface 330 (PPI)) drops below a value (e.g., a dynamic value), which may be or correlate to the pressure on the gas source side of the control assembly 320. The umbrella valve 321 may increase restriction to flow through the primary flow path 360 when the pressure on a patient interface side of the valve is higher than a pressure on a ventilator side of the valve. The umbrella valve, may reduce restriction to flow through the primary flow path 360 when the pressure on the patient interface side of the valve is less than the pressure on the ventilator side of the valve.

The exhaust vent 370 may be configured to vent at a rate such that that excess pressure is not built up within the patient interface 330, but to ensure that sufficient pressure is built, e.g., during or after patient exhalation, to cause the umbrella valve 321 of the control assembly 320 to close. The exhaust vent 370 of the non-invasive ventilation system 300 may be similar to the exhaust vent 270 discussed in connection with FIG. 2A.

Figure 3C:
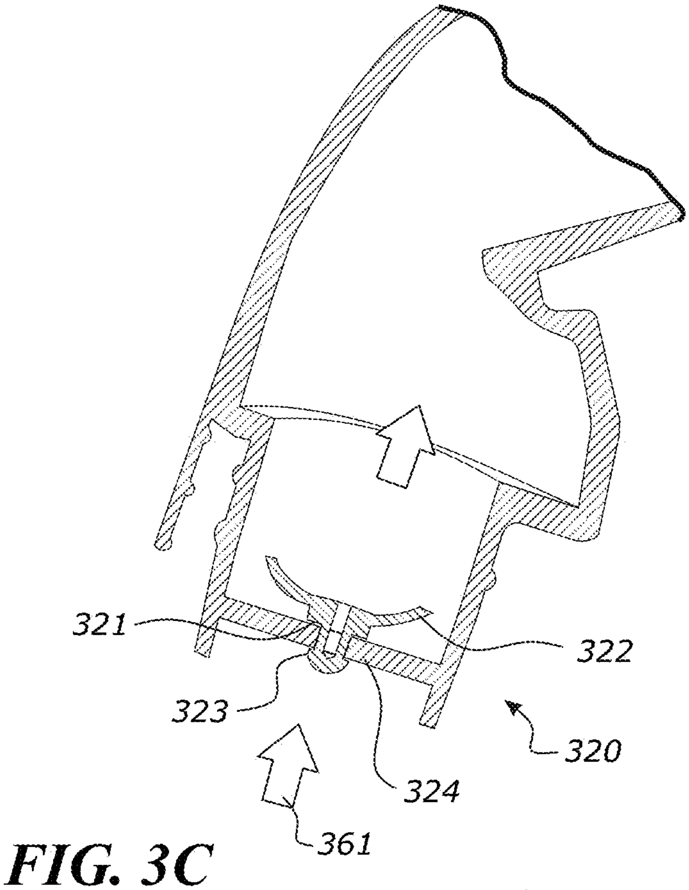
Figure 3D:
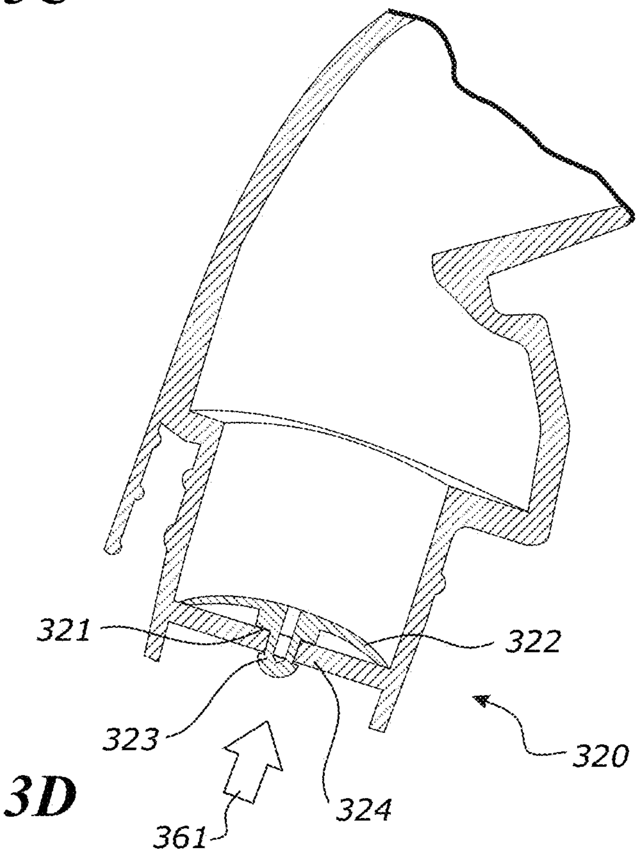

FIG. 3A shows the non-invasive ventilation system 300 during patient inhalation. In some embodiments, the flushing flow path 350 including the nasal prongs 355 is never closed. Therefore, respiratory gases may be continuously delivered to the nares of the patient through the nasal prongs 355. During inhalation, the inspiration gas flow 311 being drawn by the patient from the patient interface 330 into the patient's respiratory system reduces pressure within the breathing chamber of the patient interface 330 of the non-invasive ventilation system 300 sufficiently that the umbrella valve 321 of the control assembly 320 can open. When the umbrella valve 321 is open, such as is shown in FIGS. 3A & 3C, it allows gas to travel with relatively little restriction through the primary flow path 360 and into the patient interface 330. Because the flushing flow path 350 is always open, some gas may flow through this flow path to the patient interface during inhalation. However, due to the preference of the flow to follow the primary flow path 360 (e.g., due to lower path resistance), the flow in the flushing flow path 350 may be comparatively low, e.g., very low or negligible. However, in some embodiments, the flow may be sufficient to flush. That is, during inhalation, the second flow rate (F2) may be substantially lower than the third flow rate (F3) (by analogy to the system of FIG. 2A). The smallest cross-sectional dimension, e.g., diameter, radius, area, etc., of the primary flow path 360 may be substantially greater than the smallest cross-section al dimension, e.g., diameter, radius, area, etc., of the flushing flow path 3550 (which may be at the cross-section of the nasal prongs). Therefore, the primary flow path 360 may have a lower resistance to flow than the flushing flow path 350 when the control assembly is relatively open and not impeding, e.g., significantly impeding, flow through the primary flow path 360.

FIG. 3B shows the non-invasive ventilation system 300 of FIG. 3A during patient exhalation. During exhalation, the expiration gas flow 312 being forced into the breathing chamber of the patient interface 330 from the patient's respiratory system increases pressure within the breathing chamber patient interface 330 of the non-invasive ventilation system 300 sufficiently that the umbrella valve 321 of the control assembly 320 can close. When the umbrella valve 321 closes, such as is shown in FIG. 3B, the flow of gas through the primary flow path 360 is blocked or substantially blocked (similar to the blockage discussed in connection with the control assembly 220 of FIG. 2A). As a result, a significant portion of the gas provided by the ventilator flows through the flushing flow path 350 and to the patient, e.g., into the patient's nares through the nasal prongs 355. The flushing gas flow 351 traveling through the flushing flow path 350 due to the closed umbrella valve 321, advantageously flushes the nasal cavity with fresh air such that at the beginning of the patient's next inhalation, the nasal cavity is filled substantially with the fresh air, rather than $CO_2$ rich air.

The umbrella valve 321 of the control assembly 320 may not fully close (e.g., may not fully occlude the primary flow path 360) during exhalation. Consequently, at least some gas may flow to the patient interface 330 via the primary flow path 360 during exhalation, when the control assembly 320 is restricting or inhibiting flow through the primary flow path 360, as well as during inhalation, when the control assembly 320 is restricting the primary flow path less.

During exhalation, even though the flow of gases through the primary flow path 360 is limited, there may be sufficient flow through one or more of the primary flow path 360 and the flushing flow path 350 to generate and/or maintain at least one of EPAP and PEEP in the breathing chamber of the patient interface 330 during exhalation. In some embodiments, the limited flow of respiratory gases through the primary flow path 360 is sufficient to maintain at least one of EPAP and PEEP in the breathing chamber of the patient interface 330 during exhalation. In some embodiments, the increased flow of respiratory gas through the flushing flow path 350 is sufficient to maintain at least one of EPAP and PEEP in the breathing chamber of the patient interface 330 during exhalation. In some embodiments, the limited flow of respiratory gases through the primary flow path 360 and the increased flow of respiratory gases through the flushing flow path 350 combine to maintain at least one of EPAP and PEEP in the breathing chamber of the patient interface 330 during exhalation. The gas flow through the unsealed cannula, e.g., nasal prongs 355, is open to the breathing chamber (generally via the patient's nares) of the patient interface 330 and may assist in providing at least one of EPAP and PEEP.

Figure 4A:
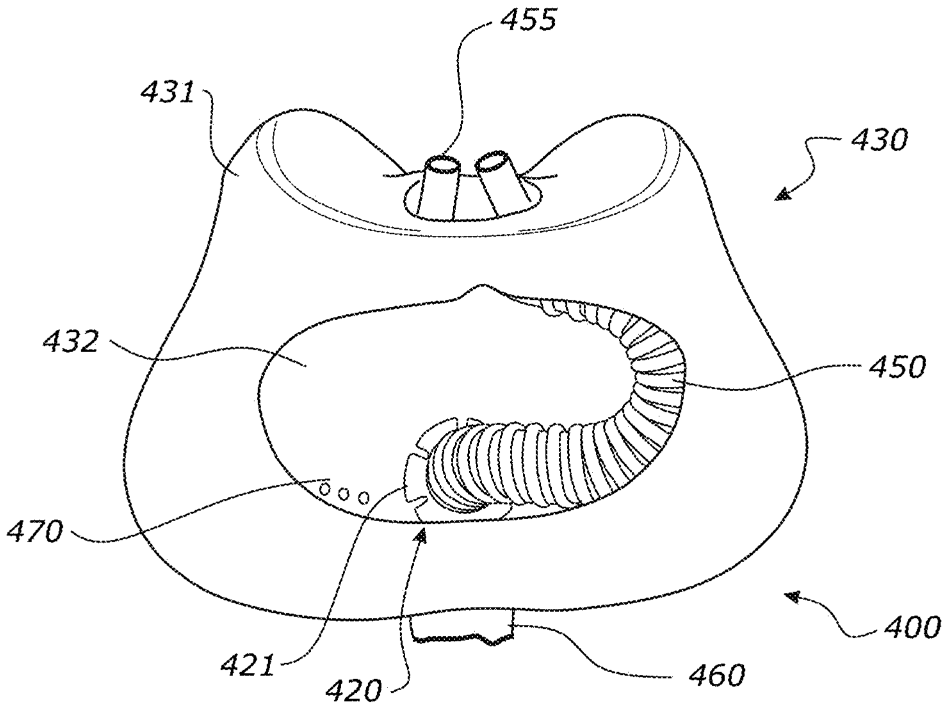
FIGS. 4A-4B are various views of an embodiment of an interface, the interface incorporating a control assembly.
Figure 4B:
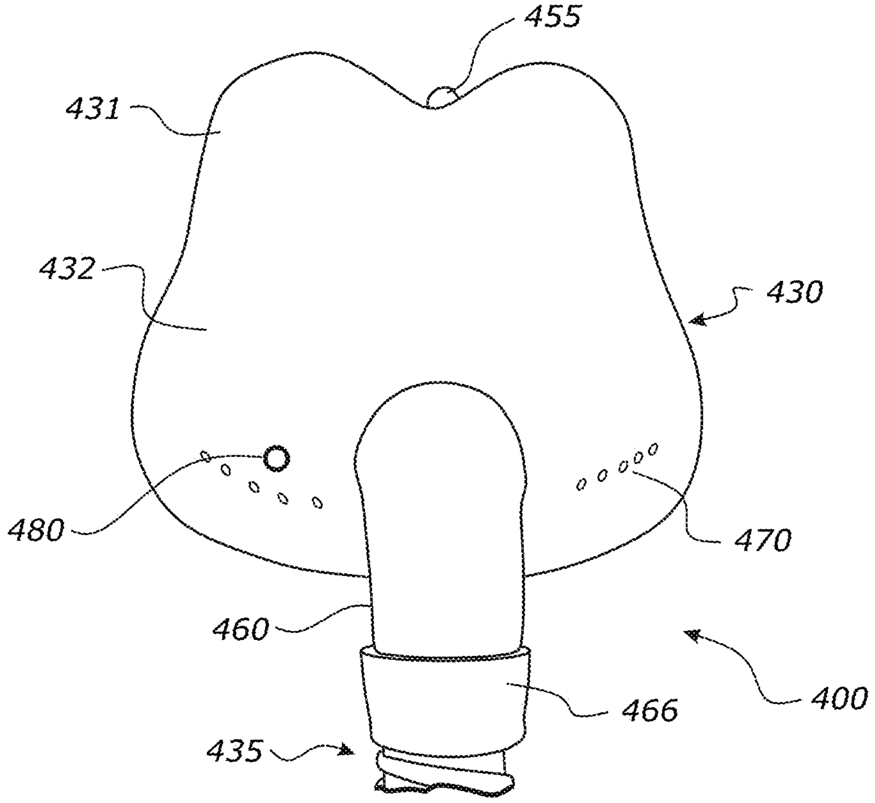

FIGS. 4A-4B illustrate portions of an embodiment of a system for noninvasive ventilation. FIG. 4A illustrates the patient-facing side of a non-invasive ventilation system 400, e.g., the posterior side of the non-invasive ventilation system 400. FIG. 4B illustrates the anterior side of the non-invasive ventilation system 400.

The non-invasive ventilation system 400 may include parts or components similar to the non-invasive ventilation system 300 of FIGS. 3A and 3B. The non-invasive ventilation system 400 generally incorporates a patient interface 430, a primary flow path 460, a flushing flow path 450, and a control assembly 420. Structure for the non-invasive ventilation system 400 may be provided, at least partially, by the patient interface 430, which may comprise a mask body 432 and a mask cushion 431. The patient interface 430, mask body 432, mask cushion 431 and breathing circuit 435 of FIG. 4A-4B may be similar to the patient interface 330, mask body 332, mask cushion 331, and breathing circuit 335 of FIGS. 3A-3B. The breathing circuit 435 may have only a single conduit to transport respiratory gases from a gas source or ventilator to the patient interface 430.

Figure 5A:
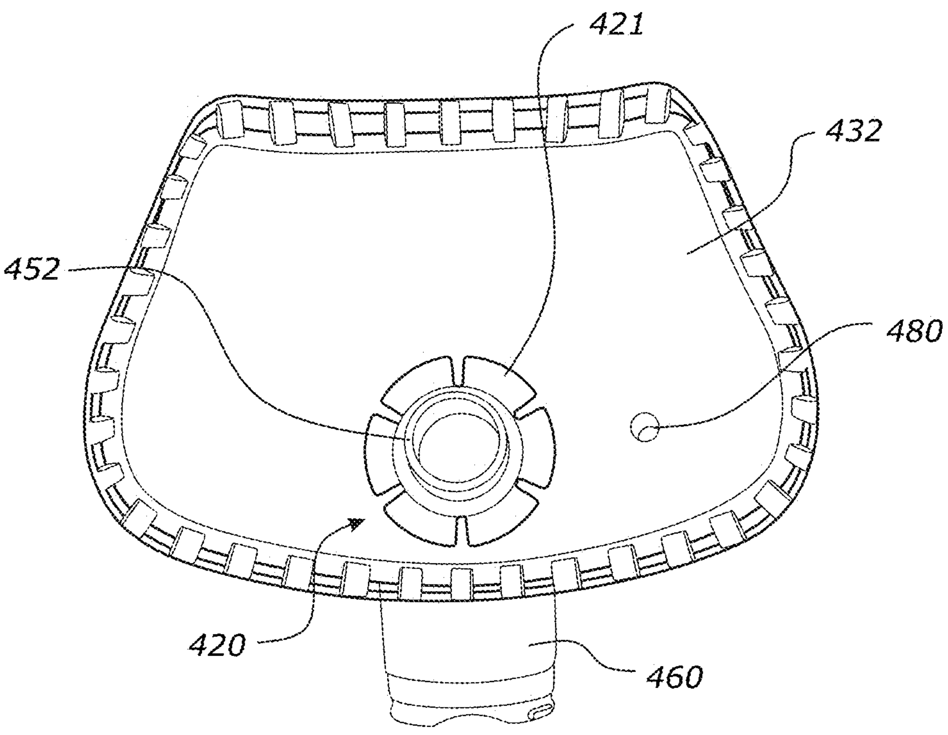
FIGS. 5A-5B are various views of portions of a patient interface and control assembly.
Figure 5B:
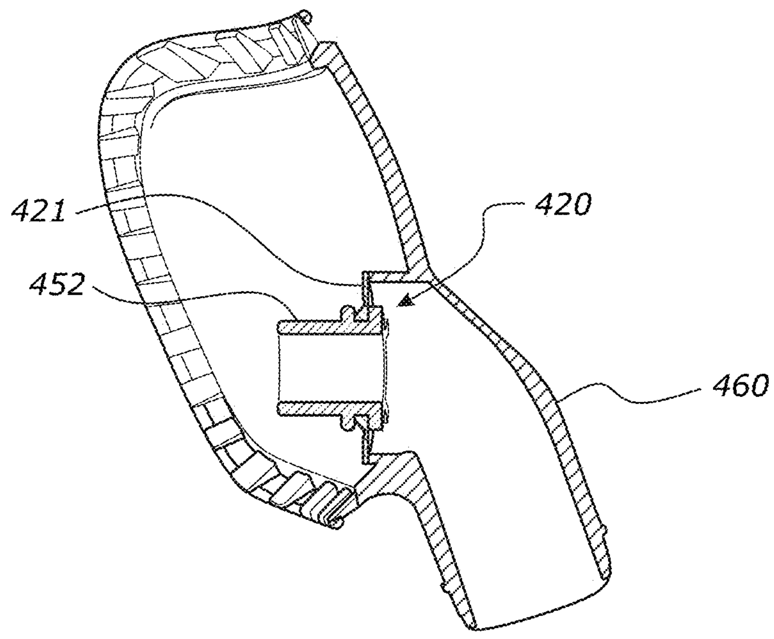

FIGS. 5A-5B illustrate various views of selected portions of the non-invasive ventilation system 400 of FIGS. 4A-4B. More specifically, FIG. 5A illustrates an anterior view of the patient interface 430 and select portions of the control assembly 420. FIG. 5B illustrates a sagittal cross-sectional view of the pieces of the non-invasive ventilation system 400 shown in FIG. 5B. As shown in FIGS. 5A-5B, the control assembly 420 splits the breathing circuit into two flow paths, e.g., two separate and/or distinct flow paths, including a flushing flow path 450 (which may ultimately be delivered to or end at a nasal delivery portion, specifically nasal prongs 455) and a primary flow path 460. The control assembly 420 may be substantially at the junction of the primary flow path 460 and the mask body 432. The control assembly 420 includes a one-way valve 421 having a plurality of movable flaps and a mounting frame 452 for mounting the one way valve 421 in the control assembly 420. The mask body 432 may include a port 480. In some embodiments, the port 480 may be used to communicate pressures to another part of the non-invasive ventilation system 400. Or, the port 480 may be used to pass a catheter or tube, such as a nasogastric tube (NG tube).

In some embodiments, the mounting frame 452 of the control assembly 420 is positioned substantially at the center of the primary flow path 460, e.g., coaxial, as shown in FIG. 5A. In some embodiments, the mounting frame 452 of the control assembly 420 is positioned off-center to the primary flow path 460. The mounting frame 452 may be entirely open to the primary flow path 460, and may define the inlet of the flushing flow path 450.

As shown in FIG. 5A, the one-way valve 421 may surround the mounting frame 452. The mounting frame acts as a divider to split the respiratory gases flowing through the breathing circuit 435 into the primary flow path 460 and the flushing flow path 450. The one-way valve 421 may be any type of valve that controls flow into the primary flow path while allowing continuous flow into a second flow path (flushing flow path). The one-way valve 421 may split the flow of respiratory gases depending on one or more factors, including, but not limited to: the pressure in a breathing chamber of the mask body 432 (PPI), the pressure of the flow from the gas source (which may be analogous to P1, discussed above in connection with FIG. 2A), and the pressure at the outlet of the primary flow path (which may be analogous to P3, discussed above in connection with FIG. 2A). As shown in FIG. 5B, the one-way valve 421 is attached to the mounting frame 452, e.g., in a groove around the base of the mounting frame 452. Depending on the pressures in the system, the outer edges of the one-way valve 421, e.g., the flaps of the one-way valve 421, may lift away from the frame and permit greater flow of respiratory gases around the flaps of the one-way valve 421, e.g., through the one-way valve 421. In this way the valve may be configured to dynamically adjust the amount of flow passing through due to the pressure differential experienced.

The flushing flow path 450 may comprise, e.g., terminate in, a nasal delivery portion, which may include nasal prongs. In some embodiments, the flushing flow path 450 comprises nasal prongs attached to the mounting frame 452 of the control assembly 420. In some embodiments, the nasal prongs are formed integrally with the mounting frame 452. In some embodiments, the high flushing flow path 450 comprises an elbow, similar to the nasal elbow 353 shown in FIG. 3A. The flushing flow path 450 provides a continuous flow path through the mounting frame 452 to the outlet of the flushing flow path 450, e.g., the nasal prongs 455.

The nasal prongs 455 may be configured to limit flow, e.g., limit or restrict the respiratory gases flowing through the flushing flow path 450. The nasal prongs 455 may be similar to the nasal prongs 355 disclosed in connection with FIGS. 3A-3B. The nasal prongs 455 may be configured to accelerate (e.g., increases the velocity) the gas flow through the flushing flow path 450. Decreased cross-sectional dimension, e.g., diameter or area, etc., may serve to accelerate the gases flowing through the flushing flow path 450. Providing a significant volumetric flow rate of gas through the flushing flow path 450, the accelerated gas flow exiting the flushing flow path 450, e.g., via the nasal prongs 455, flushes or partially flushes one or more of an anatomical dead space (e.g., the nasal cavity) of the patient or an apparatus dead space. Increased velocity of the gas flow leaving the flushing flow path 450, e.g., via the nasal prongs 455, may correlate (up to a limit) with increased efficiency of dead space flushing.

Figure 6A:
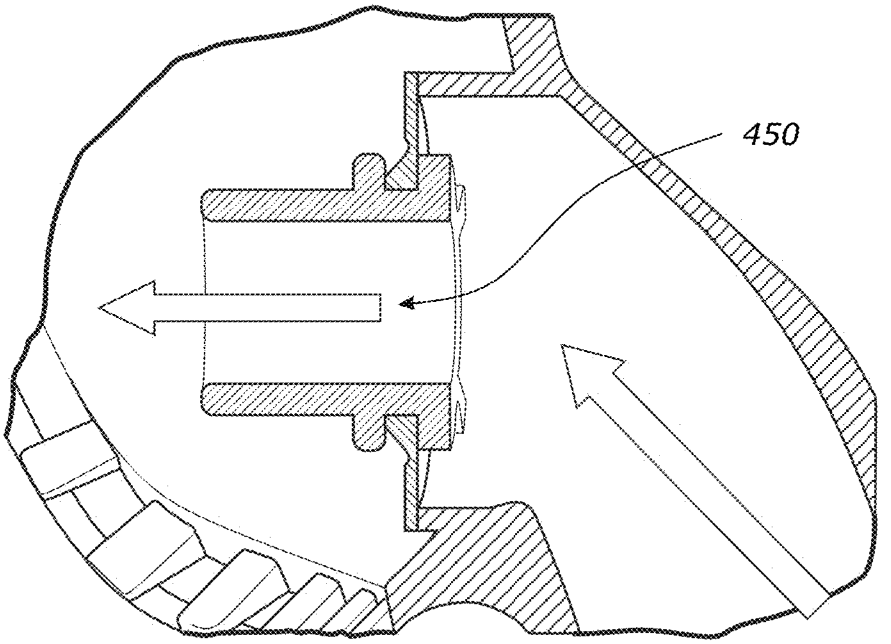
FIGS. 6A-6B show operational views of the control assembly of FIGS. 5A-5B.
Figure 6B:
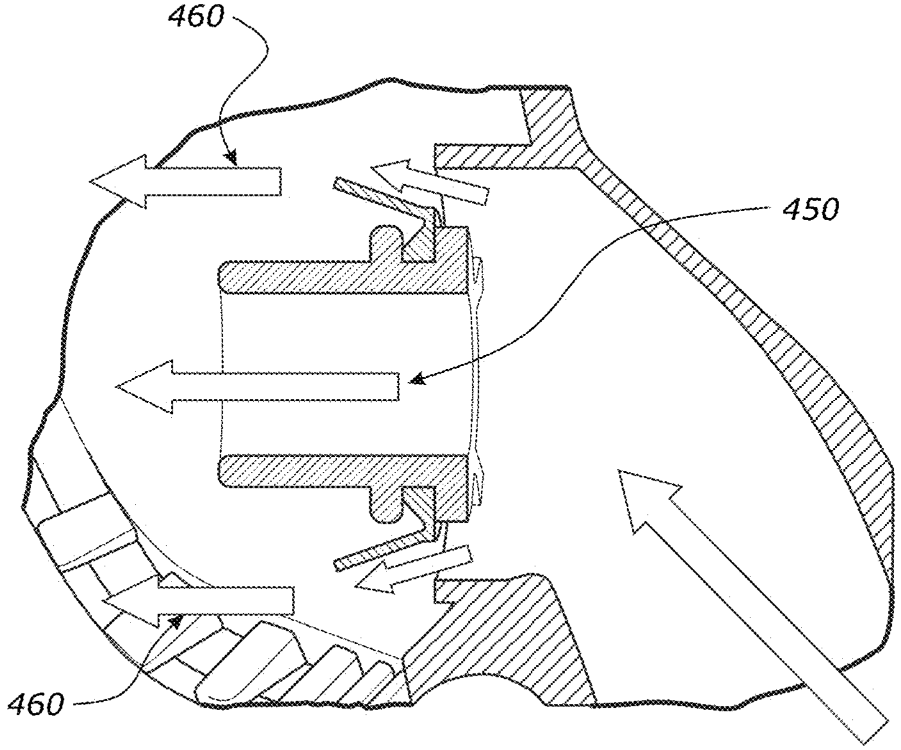

In some embodiments, the non-invasive ventilation system 400 may use pressures generated by the patient to create a passive response system. FIGS. 6A-6B illustrate the non-invasive ventilation system 400 of FIGS. 4A-4B and 5A-5B in different states (e.g., states of operation). When the pressure within the breathing chamber of the patient interface 430 is less than the pressure on the opposite side of the valve to the patient interface (e.g., on the gas source side), the one-way valve 421 is opened due to the pressure differential which reduces the restriction on the primary flow path (see FIG. 6B). When the pressure within the breathing chamber of the patient interface 430 is greater than the pressure on the opposite side of the valve to the patient interface (e.g., on the gas source side), the one-way valve 421 is forced into increasing restriction on the primary flow path (see FIG. 6A). When the one-way valve 421 is in its maximum unrestricting or open state, gas is allowed to flow relatively unrestricted through the primary flow path 460 and into the patient interface 430 (some flow may also continue to flow through the flushing flow path 350 and out of the nasal prongs 455). When the one-way valve 421 is in a substantially closed or restricted state, flow is inhibited or substantially inhibited from passing through the one-way valve 421 of the control assembly 420 into the primary flow path 460. This causes an increased portion, e.g., a substantial portion, of the flow from the gas source to pass through the flushing flow path 450 and out of the nasal prongs 455 when the pressure inside the patient interface is higher than the pressure on the opposite side of the valve to the patient interface (e.g., on the gas source side), the one-way valve 421. Due to the increased volume of respiratory gases flowing through the nasal prongs 455, the respiratory gases leaving the nasal prongs 455 may have a high velocity, sufficient to flush at least one of at least a portion of the anatomical dead space of the patient and the apparatus dead space.

The valve in the control assembly 420 of the non-invasive ventilation system 400 (e.g., the one-way valve 421) may be responsive to the magnitude of the pressure differential across the valve 421. For example, when the pressure on the gas source side of the valve (generally corresponding to the pressure at the outlet of the ventilator less any pressure losses between the ventilator and the valve) is significantly greater than the pressure on the patient interface side of the valve (generally corresponding to the pressure within the breathing chamber of the patient interface 430), the flaps of the one-way valve 421 may lift significantly, such as shown in FIG. 6B, thereby allowing a relatively high volume of flow past. When the pressure on the gas source side of the valve is only marginally greater than the pressure on the gas source side of the valve (e.g., the pressure within the breathing chamber of the patient interface 430), the flaps of the one-way valve 421 may lift only a short distance thereby allowing only a relatively small volume of flow past. As is discussed herein, particularly with reference to FIGS. 7A-7K, the one-way valve 421 may be configured to allow more or less flow based on a certain (e.g., a given or set) pressure differential. The ability of the one-way valve 421 to respond to a pressure differential may be advantageous in configuring the control assembly 420 of the non-invasive ventilation system 400 to respond dynamically to a real patient's breaths (and the difference between breaths of different patients).

FIG. 6B shows the control assembly 420 of the non-invasive ventilation system 400 during patient inhalation. In some embodiments, the flushing flow path 450 connected to the nasal prongs 455 is never closed. However, the flushing flow path 450 may be comparatively more restricted (e.g., has a higher resistance) to flow than the primary flow path 460 when the one-way valve 421 is in at least its most open condition. Therefore, when the control assembly 420 is open, e.g., during user inhalation, the majority of respiratory gas will flow from the primary flow path 460 and through the one-way valve 421 of the control assembly 420—only a comparatively small, minor, or minimal volume of gas will flow through the continuously open flushing flow path 450 and the nasal prongs 455 at its end. During inhalation, the respiratory gas flow being drawn by the patient from the patient interface 430 into the patient's respiratory system reduces pressure within the breathing chamber of the patient interface 430 of the non-invasive ventilation system 400 sufficiently that the one-way valve 421 of the control assembly 420 can open due to the pressure being supplied by the gas source being lower than the pressure within the breathing chamber.

FIG. 6A shows the control assembly 420 of the non-invasive ventilation system 400 during patient exhalation.

During exhalation, the expiration gases being forced into the breathing chamber of the patient interface 430 from the patient's respiratory system increase the pressure within the breathing chamber of the patient interface 430 sufficiently that the one-way valve 421 of the control assembly 420 closes at least partially. As the one-way valve 421 moves towards closure, the flow of respiratory gases through the primary flow path 460 is blocked or substantially blocked (similar to the blockage discussed in connection with the control assembly 220 of FIG. 2A). Closure of the one-way valve 421 can cause an increase, e.g., a relatively immediate increase, in the volumetric flow of respiratory gases flowing through the flushing flow path 450 and into the patient's nares through the nasal prongs 455. As the flushing flow path 450 comprises nasal prongs 455 with comparatively small outlets, the increased volumetric flow of respiratory gases through the flushing flow path 450 increases the velocity of the gas at the nasal prong outlets.

Exhalation generally forces $CO_2$ rich air into the patient's nasal cavity and out of the patient's nares. The non-sealing nasal prongs 455 allow the expiration gases to be expired through the nares. Additionally, the increased volume and velocity of the respiratory gases traveling through the flushing flow path 450, e.g., due to the substantially closed one-way valve 421, serve to flush the nasal cavity with fresh air such that at the beginning of the patient's next inhalation, the nasal cavity is filled substantially with the fresh air, rather than $CO_2$ rich air.

During exhalation, even though the flow of gases from the primary flow path 460 through the one-way valve 421 may be limited (e.g., severely limited), there may be sufficient flow from/through one or more of the primary flow path 460 through the one-way valve 421 and the flushing flow path 450 to generate and/or maintain at least one of EPAP and PEEP in the breathing chamber of the patient interface 430 during exhalation. In some embodiments, the limited flow of respiratory gases from the primary flow path 460 through the one-way valve 421 is sufficient to maintain at least one of EPAP and PEEP in the breathing chamber of the patient interface 330 during exhalation. In some embodiments, the increased flow of respiratory gas through the flushing flow path 450 is sufficient to maintain at least one of EPAP and PEEP in the breathing chamber of the patient interface 430 during exhalation. In some embodiments, the limited flow of respiratory gases from the primary flow path 460 through the one-way valve 421 and the increased flow of respiratory gases, e.g., the exhaled breath from the patient, combine to maintain at least one of EPAP and PEEP in the breathing chamber of the patient interface 430 during exhalation. The gas flow through the unsealed cannula, e.g., nasal prongs 455, is open to the breathing chamber (generally via the patient's nares) of the patient interface 430 and may assist in providing at least one of EPAP and PEEP.

FIGS. 7A-7K show various embodiments of a one-way valve in the form of a flap valve. The flap valve comprises a mounting structure in the form of ring having an aperture through a generally cylindrical body. The mounting structure enables the flap valve to be mounted in the primary flow path. The flap valve further comprises a plurality of projections radially disposed around the mounting structure. Each projection may be referred to as a flap of the flap valve. In some embodiments, each projection is offset from one side of the ring. This provides the mounting structure with a raised lip to enable more secure mounting in the flow path. However, in other embodiments, each projection may have the same thickness as the ring body so that the projections have flush surfaces with the ring.

Each projection or flap may comprise a recessed region on one side of the flap located adjacent the junction between the ring and the projection. These recessed regions enable each projection to be deformed in one direction with a significantly lower force than is required to deform the flap in a second direction. In some embodiments, the recessed regions enable the projection valve to act as a one-way valve. In some embodiments, there is a restricting portion in the flow path and/or on the mounting structure to restrict the flaps from deforming in a second direction.

FIGS. 7A-7K illustrate various different one-way valves that may be used with some embodiments of the noninvasive ventilation systems disclosed herein, such as the non-invasive ventilation system 400 shown in FIGS. 4A-4B, 5A-5B, and 6A-6B. One-way valves, as disclosed herein, may be configured such that each individual projection or flap of the valve may open independently to permit air flow. The use of flaps may allow or improve the case of opening of the valve (e.g., reduce the pressure differential needed for the valve to open/close) and/or its ability to remain open even with comparatively small pressure differentials.

Figure 7A:
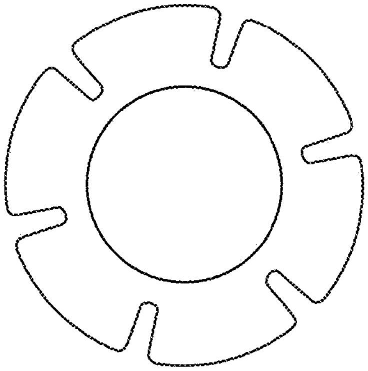
FIGS. 7A-7K show various views of various different embodiments of a valve component of a control assembly.
Figure 7B:
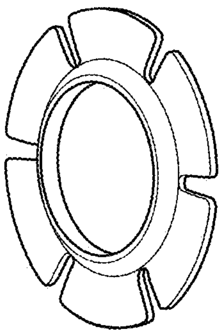
Figure 7C:

FIGS. 7A-7C show a first embodiment of a flap valve with a centrally located aperture. The mounting structure is surrounded by six radially disposed flaps each equidistantly spaced around the perimeter of the mounting surface. The raised lip as shown in FIGS. 7B and 7C provides a locating feature for mounting the flap valve in the primary flow path. Each flap extends away from the central aperture in a direction that is normal to the face of the ring. The flaps are substantially flat and have no curvature. The flaps are radially spaced around the mounting surface with a gap formed between each flap such that they do not contact each other. This gap may correspond with structures used for mounting the flap valve in the primary flow path or structures used to limit the flaps from bending in one direction while allowing for them to bend in a second, opposed direction. Each flap extends equidistantly away from the ring. The distal edges of each flap are curved. In combination, the distal edges of each flap define a circle that is parallel to the ring of the mounting structure.

The one-way valve has an outer diameter (which may be seen in FIG. 7A), an inner diameter (which may be seen in FIG. 7A), a thickness (which may be seen in FIG. 7C), a flap cut depth (which may be seen in FIG. 7A), and a number of flaps (which may be seen in FIGS. 7A and 7B). The inner diameter of the one-way valve may be a function of the structure around which the one-way valve is fixed. For example, the one-way valve shown in FIGS. 7A-7B has an inner diameter that is substantially equal to the diameter of the recess on the mounting frame fitting 452. The inner diameter may be such that the inner surface of the one-way valve forms a gas tight or substantially gas tight seal with the structure around which it is placed. The outer diameter of the one-way valve may be dimensioned such that it covers, substantially covers, or overlaps the outer edge of the port being covered (an example of which is shown in FIG. 7A). The thickness of the one-way valve may affect the performance of the valve, e.g., a thicker one-way valve 421 may require a larger pressure differential to open while a thinner one-way valve 421 may require a smaller pressure differential to open. The one-way valve shown in FIGS. 7A-7C has 6 flaps. In some embodiments, the one-way valve has a number of flaps less than about 20, less than about 18, less than about 16, less than about 14, less than about 12, less than about 10, less than about 8, less than about 6, less than about 4, or less than about 2. In some embodiments, the one-way valve has one flap.

Figure 7D:
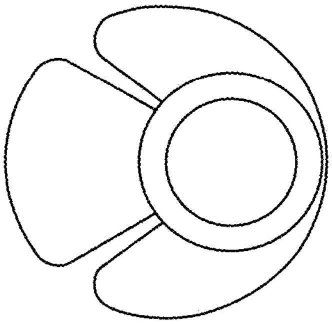
Figure 7E:

FIGS. 7D-7E show a second embodiment of a flap valve with a non-centrally located aperture. The aperture is offset towards one side of the flap valve. Three non-uniformly shaped flaps are spaced around the perimeter of the mounting structure. Although the individual flaps are non-uniform, they are shaped and located so that the outside perimeter of the flap valve is substantially circular. The flaps are spaced apart such that they do not contact each other. The flap valve comprises a central, main flap and two smaller side flaps to either side of the central flap. The central flap is larger than each of the side flaps. The central flap is a different shape to the side flaps. The central flap is triangular shaped with a curved distal edge from the mounting structure.

Figure 7F:
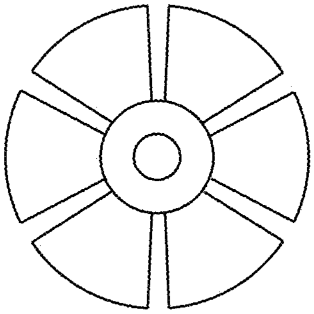
Figure 7H:
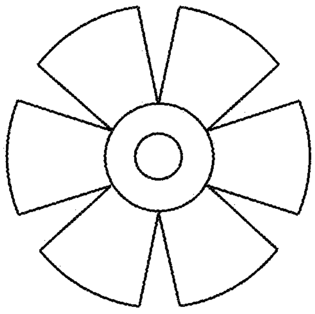
Figure 7J:
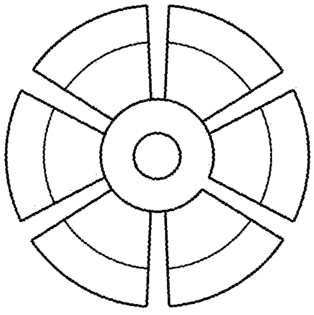
Figure 7G:
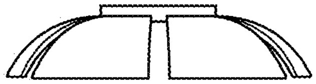

The embodiment of the one-way valve shown in FIGS. 7F-7G has a curved and inclined flap surface. The embodiment of the one-way valve shown in FIGS. 7H-7I has a flat and inclined flap surface. The embodiment of the one-way valve shown in FIGS. 7J-7K has a stepped flap surface.

FIGS. 7F-7G show a third embodiment of a flap valve comprising a centrally located aperture. The raised lip of the mounting structure is surrounded by six uniform and equidistantly spaced flaps. The flaps extend from the mounting structure in two dimensions (upwardly and outwardly). The flaps curve away from the mounting structure. Each flap has a profile that is substantially in the shape of a quarter oval.

Figure 7I:

FIGS. 7H-7I show a fourth embodiment of a flap valve comprising a centrally located aperture. The mounting structure has six uniform radially disposed flaps each equidistantly spaced around the perimeter of the mounting structure. The flaps have surfaces that are flush with surfaces of the ring. The flaps extend from the mounting structure in two dimensions (upwardly and outwardly). The flaps are substantially planar. The side profile of each flap is substantially linear. In this embodiment the spacing between the flaps increases from the mounting surface towards the distal edge of the flap valve creating triangular shaped spaces between adjacent flaps.

Figure 7K:
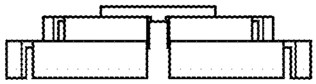

FIGS. 7J-7K show a fifth embodiment of a flap valve comprising a centrally located aperture. The mounting structure has six uniform radially disposed flaps each equidistantly spaced around the perimeter of the mounting structure. The flaps when viewed in a side profile have a substantially stepped profile. Each flap comprises at least two stepped sections. Each stepped section comprises a first portion that extends radially away from the mounting structure and a second portion that extends at an angle to the first portion. The second portion may be substantially perpendicular to the first portion. The second portion may be substantially parallel to the central axis of the aperture of the mounting structure.

Figure 8:
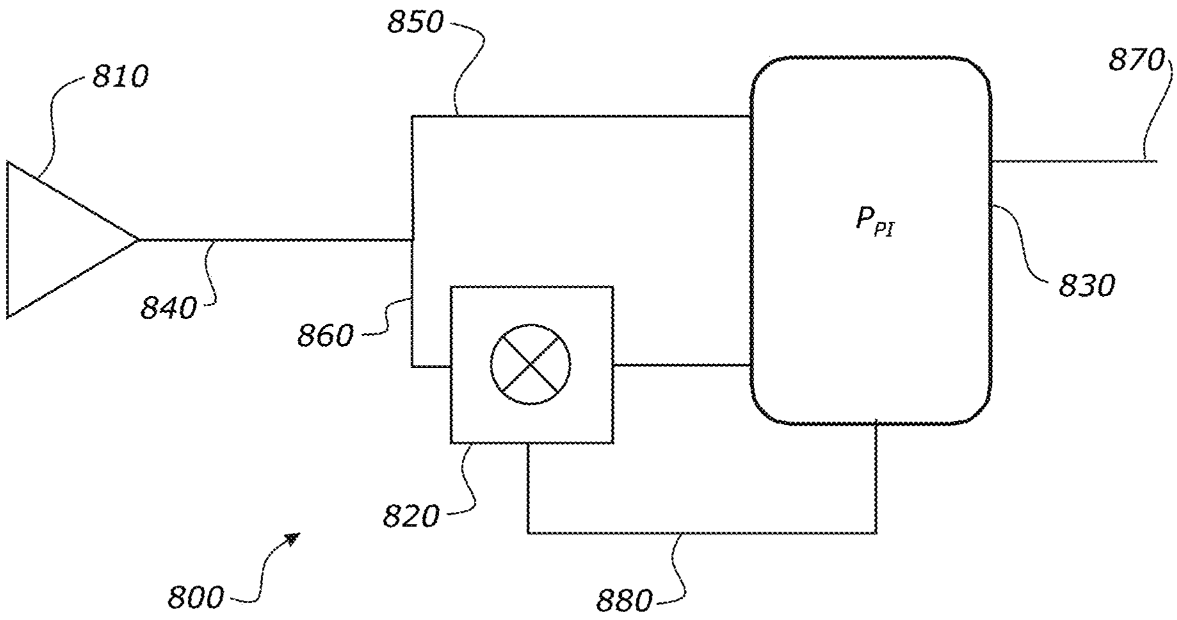
FIG. 8 is a block diagram of an embodiment of a system that may be used for noninvasive ventilation.

FIG. 8 illustrates a block diagram of an embodiment of a system for providing and/or maintaining noninvasive ventilation. As shown, the noninvasive ventilation system 800 includes various components, including, but not necessarily limited to, a gas source 810, a control assembly 820, a patient interface 830, a breathing circuit 835, an exhaust vent 870, and a feedback arrangement 880. The components of the noninvasive ventilation system 800 may be substantially similar to the components of the noninvasive ventilation system 200 discussed in connection with FIG. 2A. For example, the gas source 810 may correspond to the gas source 210, the breathing circuit 835 may correspond to the breathing circuit 235, the flushing flow path 850 may correspond to the flushing flow path 250, etc. While some components may be similar, substantially similar, or even identical between the noninvasive ventilation system 800 and the noninvasive ventilation system 200, none are required to be similar, substantially similar, or identical.

The noninvasive ventilation system 800 may operate substantially the same as the noninvasive ventilation system 200 of FIG. 2A. The gas source 210 has an outlet connected to the breathing circuit 835 by which the gas source supplies breathing gas. The pressure and flow at the outlet of the gas source are nominally a first pressure, P1 and a first volumetric flow rate, F1. The gas source 810 is controlled to provide a first pressure and first flow rate (P1, F1) to achieve a desired pressure at the patient interface, in particular in the breathing chamber of the mask. The first pressure and first flow rate (P1, F1) may therefore be controlled to account for any system pressure losses between the gas source 810 and the patient interface 830. As previously mentioned, the desired pressure at the patient interface may vary during the user's respiration cycle (e.g., between an IPAP and an EPAP).

The breathing circuit 835 divides, bifurcates or splits into the flushing flow path 850 and the primary flow path 860, each flow path having separate outlets in the patient interface through which breathing gas is delivered to the user. The pressure and flow at the outlet of the flushing flow path are nominally a second pressure, P2 and a second volumetric flow rate, F2. The pressure and flow at the outlet of the primary flow path are nominally a third pressure, P3 and a third volumetric flow rate, F3.

The feedback arrangement 880 is in the form of a connection, port or line that communicates the pressure within the patient interface 830 to the control assembly 820. The feedback arrangement may be separate from the breathing circuit 835 and from the primary and flushing flow paths. The control assembly 820 may modulate the flow allowed through the primary flow path 860 based on the pressure of the gas within the patient interface 830, e.g., the pressure communicated to the control assembly 820 by the pressure arrangement 880.

The control assembly 820, at least in part, defines the inlet to the primary flow path 860 from the gas source 810. The flushing flow path 850 is connected to the gas source 810 via a set flow path that is not directly changed or modified by the control assembly. The control assembly 820 has a gas source side and a patient interface side. The gas source side of the control assembly includes an inlet to the control assembly. The patient interface side of the control assembly includes the pressure feedback arrangement 880. The control assembly is configured to vary the flow resistance of the primary flow path. The control assembly is operable such that when the pressure on the gas source side of the control assembly (generally corresponding to P1 less any pressure losses between the gas source outlet and the control assembly) is higher than pressure on the patient side of the control assembly (generally corresponding to the pressure in the patient interface breathing chamber less any pressure loss across the pressure feedback arrangement 880), flow through the primary flow path 860 is open or less restricted by the control assembly. The greater the pressure differential between the gas source side and the patient interface side of the control assembly (with the gas source side being a higher pressure than the patient interface side), the less restricted the primary flow path 860 will be.

The control assembly is also operable such that when pressure on the patient interface side of the control assembly (generally corresponding to the pressure in the patient interface breathing chamber less any pressure loss across the pressure feedback arrangement 880) is greater than the pressure on the gas source side of the control assembly (generally corresponding to P1 less any pressure losses between the gas source outlet and the control assembly), flow through the primary flow path is restricted or more restricted by the control assembly. The greater the positive pressure differential between the patient interface side and the gas source side, the more restricted the flow through the primary flow path may be.

When the control assembly restricts flow through the primary flow path, for the same pressure (P1) at the outlet of the gas source, the flow (F3) through the outlet of the primary flow path is reduced and the flow (F2) through the outlet of the flushing flow path is increased. As the volumetric flow rate through the flushing flow path is increased the velocity of the gas flow through the flushing flow path is also increased. The system is configured so that the velocity of the gas flow through the flushing flow path is sufficiently high enough for a sufficient duration of the user's breathing cycle to achieve flushing of the anatomical and/or apparatus dead space. Similarly, when the control assembly opens flow through the primary flow path, for the same pressure (P1) at the outlet of the gas source, the flow (F3) through the outlet of the primary flow path is increased and the flow (F2) through the outlet of the flushing flow path is decreased due to the lowered resistance to flow through the primary flow path.

An increase in pressure on the patient interface side of the control assembly relative to the pressure on the gas source side of the control assembly generally occurs during user exhalation. This is because the user is breathing out and adding mass to the fixed volume of gas in the patient interface and thus increasing the pressure in the patient interface breathing chamber. During user inhalation, the pressure on the patient interface side of the control assembly is usually lowered relative to the pressure on the gas source side of the control assembly because the user is drawing air in from the patient interface and therefore removing mass from the fixed volume in the patient interface breathing chamber. The system may be configured to provide flushing of the anatomical and/or apparatus dead space mostly during exhalation and may rarely, if at all provide flushing during inhalation.

Figure 9A:
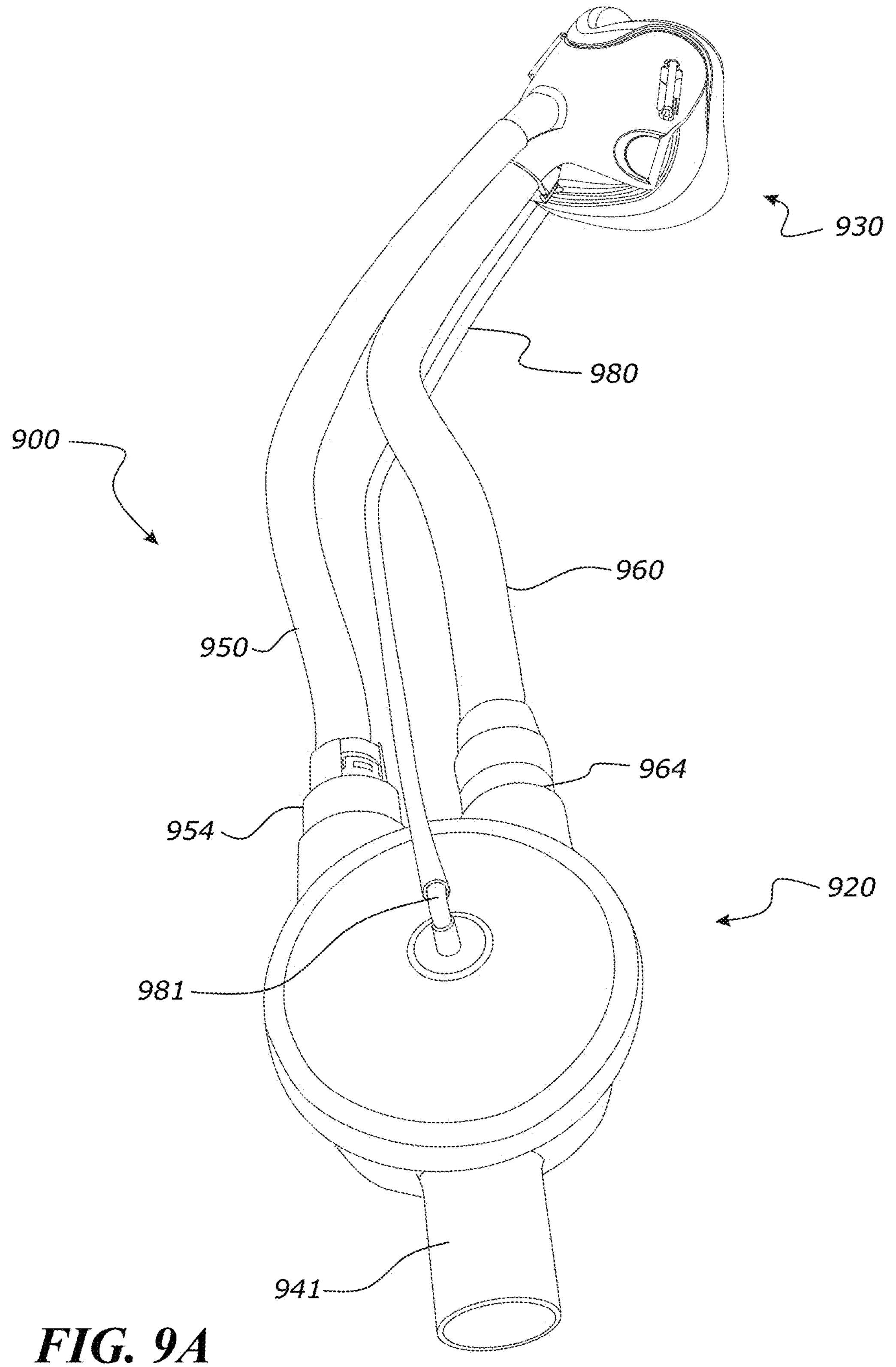
FIGS. 9A-9B are various views of an embodiment of a patient interface and a control assembly.
Figure 9B:
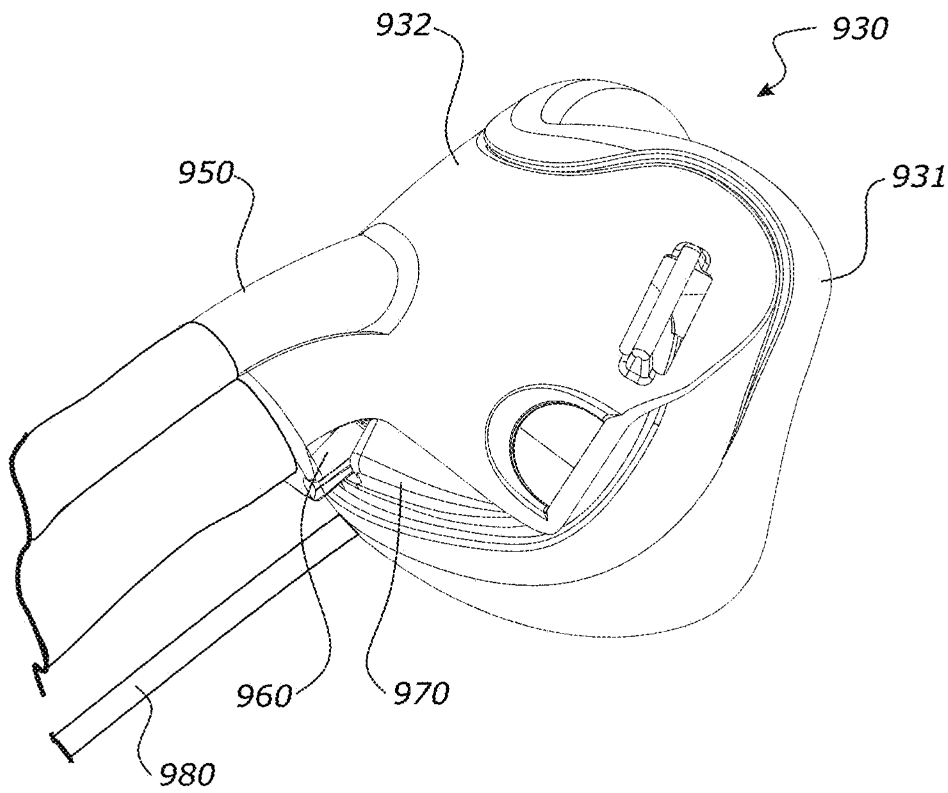

FIGS. 9A-9B illustrate select portions of an embodiment of a system for noninvasive ventilation 900 including a patient interface 930 configured to receive gases from a flushing flow path 950 and a primary flow path 960. FIG. 9A also shows a control assembly 920 having four ports/connectors, including a gas source connector 941, a flushing flow path connector 954, a primary flow path connector 964, and a pressure feedback port 981. The gas source connector 941 is configured to connect the control assembly 920 to a gas source conduit which places the control assembly 920 in fluid communication with a gas source such as a ventilator or other source of pressurized breathing gas. The primary flow path connector 964 is configured to connect the control assembly 920 to the primary flow path 960, which extends between the control assembly 920 and the patient interface 930. The flushing flow path connector 954 is configured to connect the control assembly 920 to the flushing flow path 950, which extends between the control assembly 920 and the patient interface 930.

The patient interface 930 has three paths of fluid communication with the control assembly 920: the primary flow path 960, the flushing flow path 950, and the pressure feedback arrangement 980. The pressure feedback arrangement 980 and the flushing flow path 950 may be continuously open, e.g., in open fluid communication with the breathing chamber of the patient interface. As described elsewhere herein, the primary flow path 960 may be open (e.g., fully or substantially open) or restricted (e.g., fully or substantially closed) depending on the modulation provided by the control assembly 920, which is discussed in further detail elsewhere herein. When the control assembly 920 is connected to a ventilator, breathing gases may be continuously delivered to the patient interface 930. When the control assembly 920 is restricting flow through the primary flow path, a significant portion of breathing gases are delivered to the patient interface 930 through the flushing flow path 950 (the portion of the gases blocked form passing through the primary flow path 960 by the control assembly 920 are passed through the flushing flow path 950). When the control assembly 920 is open and not restricting flow through the primary flow path, breathing gases are delivered to the patient interface 930 through both the primary flow path 960 and the flushing flow path 950. The primary flow path 960 may have a lower resistance to flow than the flushing flow path 950. Therefore, when all paths are open, more of the gas from the ventilator 910, e.g., substantially more of the gas, may pass through the primary flow path 960 as it is the path of least resistance to the patient interface 930. The flushing flow path 950 or a portion thereof (e.g., nasal prongs at the terminal end of the flushing flow path 950) may have an increased resistance to flow by comparison to the primary flow path 960. Therefore, when the control assembly 920 is restricted, the increased volumetric flow of breathing gases increases, e.g., dramatically increases the velocity of the gases exiting the flushing flow path 950. Increased or high velocity gases may be used to flush one or more of an anatomical dead space (e.g., the patient's nasal cavity) and an apparatus dead space.

Figure 10:
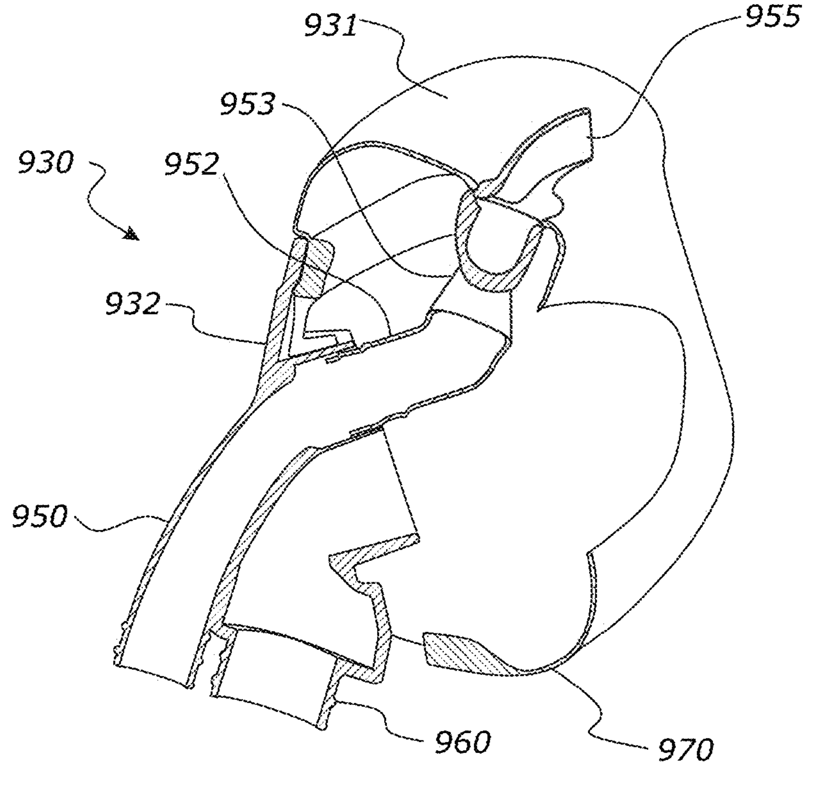
FIG. 10 shows a vertical cross-sectional view of an embodiment of a patient interface.

FIGS. 9B and 10 illustrate the patient interface 930 of FIG. 9A. The patient interface 930 includes a mask body 932 and a mask cushion 931 attached to the mask body. The patient interface 930 also includes an exhaust vent 970, which may be configured to vent gases at a rate corresponding to an internal pressure of the patient interface 930. The patient interface 930 can be similar to the patient interface 330 of FIGS. 3A-3B, except as disclosed herein.

The mask body 932 may be formed from a rigid or semi-rigid material, such as a polycarbonate. The edge(s) of the mask body 932 is attached to a mask cushion 931. The mask cushion 931 is formed of a relatively soft and flexible material such as silicone, foam and/or fabric. The cushion is configured, by one or more of shape and material selection, to conform to the user's face while in use and thereby discourage, reduce, or eliminate uncontrolled leaking of the gas out of the patient interface 330, e.g., from between the user's face (or portion thereof) and the mask cushion 931. The mask body 932 and mask cushion 931 together define a breathing chamber of the patient interface 930. One or more components of the patient interface 930 may be substantially similar to the components of the non-invasive ventilation system 300 discussed in connection with FIGS. 3A-3B. For example, the flushing flow path 950 may correspond to the flushing flow path 350, the primary flow path 960 may correspond to the primary flow path 360, the exhaust vent 970 may correspond to the exhaust vent 370, the nasal prongs 955 may correspond to the nasal prongs 355, the mask cushion 931 may correspond to the mask cushion 331, and the mask body 932 may correspond to the mask body 332, etc. While some components may be similar, substantially similar, or even identical in structure and/or function between the patient interface 930 and the non-invasive ventilation system 300, none are required to be similar, substantially similar, or identical.

Figure 11A:
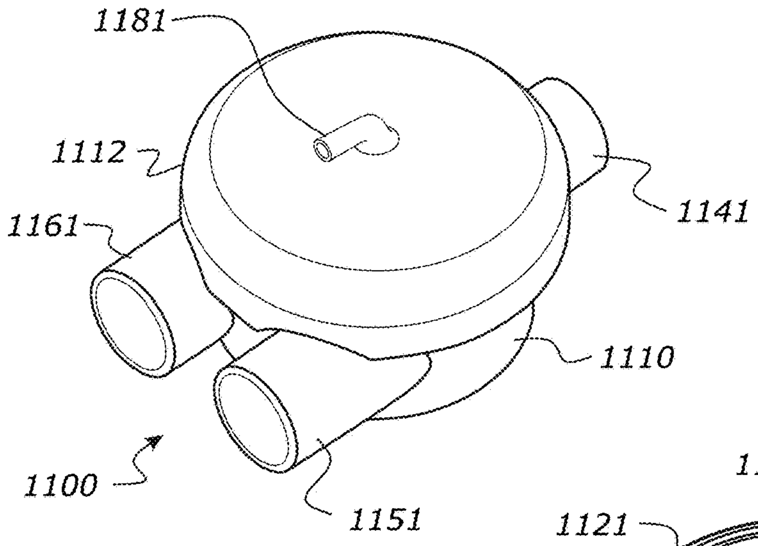
FIGS. 11A-11C show various views of an embodiment of a control assembly that may be used in connection with various embodiments of systems.
Figure 11B:
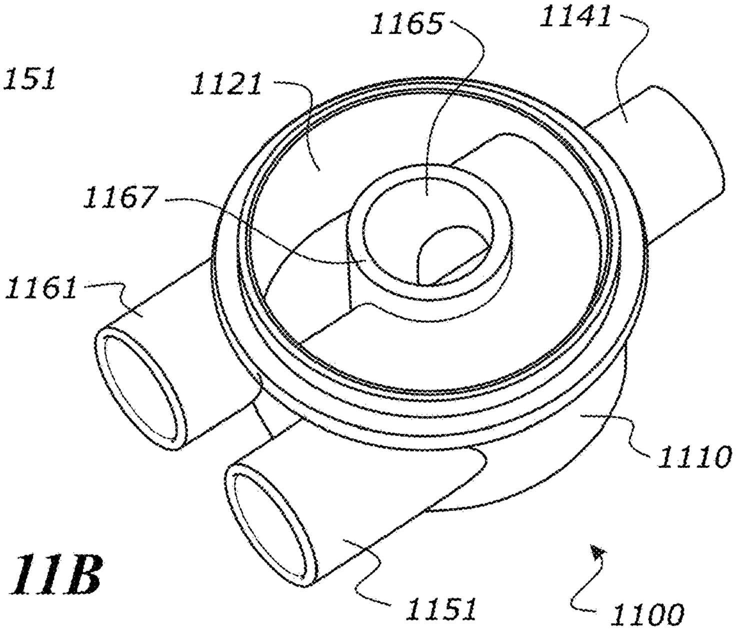
Figure 11C:
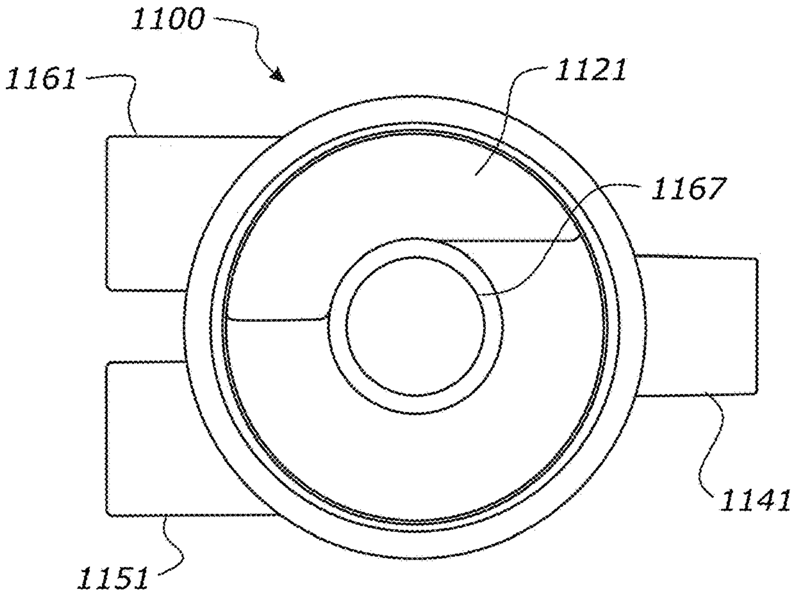

FIGS. 11A-11C show various views of a control assembly 1100 that may be used with various embodiments of a system for noninvasive ventilation. FIG. 11A illustrates an external view of the control assembly 1100 when it is fully assembled. FIGS. 11B and 11C illustrate various views of the control assembly 1100, partially disassembled for illustration purposes.

The control assembly 1100 generally includes a housing or body comprising a control assembly lower body 1110 and a control assembly upper body 1112. The body of the control assembly 1100 contains structures and components that are configured to divert or split a flow of respiratory gases between different flow paths. The control assembly may include a number of ports for incoming gases, e.g., one port for incoming gases, and a number of ports for outgoing gases, e.g., two ports for outgoing gases.

The control assembly 1100 may include one port, e.g., ventilator port 1141, that is configured to receive a flow of gases from a gas source such as a ventilator. The ventilator port 1141 may connect to a ventilator conduit and guide gases received from the ventilator into the body of the control assembly 1100, e.g., the control assembly lower body 1110. The ventilator port 1141 accepts gases at a first pressure (P1) less any pressure losses between the ventilator and the ventilator port and a first flow rate (F1).

The control assembly 1100 may include two ports, e.g., flushing flow port 1151 and primary flow port 1161, that are configured to guide gases out of the control assembly 1100, e.g., out of the control assembly lower body 1110. Gases may leave the flushing flow port 1151 at a second pressure (P2) plus any pressure losses that occur between the flushing flow port and the opening of the nasal cannula and a second flow rate (F2). Gases may leave the primary flow port 1161 at a third pressure (P3) plus any pressure losses that occur between the primary flow port and the primary flow path opening in the mask body and a third flow rate (F3). Each of the ventilator port 1141, the flushing flow port 1151, and the primary flow port 1161 may be connected to or integrally formed with the control assembly lower body 1110.

FIGS. 11B and 11C illustrate the control assembly 1100 without the control assembly upper body 1112 in place. The control assembly lower body 1110 has a split into two different flow paths after the ventilator port inlet; a primary flow path that is in fluid communication with the primary flow port 1161 and a flushing flow path that is in fluid communication with the flushing flow port 1151. The flushing flow path extends directly from the ventilator port 1141 to the flushing flow port 1151. The flushing flow path is in constant fluid communication with the flushing flow port 1151. Therefore, some volume of gas is constantly free to travel from the ventilator port 1141, through the control assembly lower body 1110, and out of the flushing flow port 1151 at all times during operation of the non-invasive ventilation system 1100. The primary flow path extends from the ventilator port 1141, turns toward the control assembly upper body 1112 to extend through an opening 1165 in the control assembly lower body 1110 and to the primary flow port 1161. The primary flow path may be restricted, limited or shut by a movable member in the form of a diaphragm 1121. The movable member is arranged to occlude, block or restrict the opening in the control assembly lower body in order to restrict gas flow through the primary flow path. The opening 1165 is defined or bounded by a tubular portion of the lower body 1110. The tubular portion is substantially cylindrical in cross-section. The tubular portion has an annular or ring end surface 1167.

The diaphragm 1121 is held between the control assembly lower body 1110 and the control assembly upper body 1112. The diaphragm 1121 may be a generally circular member. The diaphragm 1121 may be formed from a flexible material. The diaphragm 1121 may be clamped at or towards its perimeter edge between the control assembly upper body 1112 and control assembly lower body 1110. The diaphragm 1121 is moved towards a restricting position when the pressure on the upper side of the diaphragm 1121 (e.g., the side facing the control assembly upper body 1112 or the patient interface side of the diaphragm) is greater than the pressure on the lower side of the diaphragm 1121 (e.g., the side facing the control assembly lower body 1110 or the gas source side of the diaphragm). The diaphragm 1121 is moved towards a less restricting or open position when the pressure on the upper side of the diaphragm is less than the pressure on the lower side of the diaphragm 1121. Movement of the diaphragm 1121 towards the restricting position involves movement towards the opening in the control assembly lower body 1110 and specifically towards the ring end surface 1167 of the tubular portion. Movement of the diaphragm 1121 towards the open position involves movement away from the opening 1165 in the control assembly lower body 1110 and specifically away the ring end surface 1167 of the tubular portion.

The diaphragm 1121 of the control assembly 1100 can provide a non-binary response to the pressure differential across the diaphragm 1121. For example, when the pressure on the lower side of the diaphragm 1121 is only marginally greater than the pressure on the upper side of the diaphragm 1121, only a small amount of flow (e.g., a small volume of gas) may be allowed to pass from the ventilator port 1141, through the opening (past the ring end surface 1167 and the diaphragm 1121), and out of the primary flow port 1161. If the pressure on the patient interface side of the diaphragm 1121 is significantly large/high enough relative to the pressure on the gas source side, the diaphragm 1121 will be moved into engagement with the ring end surface 1167 of the tubular portion to at least partially scal off the opening in the control assembly lower body 1110. When the pressure on the lower side of the diaphragm 1121 is significantly greater than the pressure on the upper side of the diaphragm 1121, a significant volume of flow may be allowed to pass from the ventilator port 1141, through the opening 1165 and out of the primary flow port 1161. In other words, there may be a relationship between the volumetric flow out of the primary flow port 1161 and the size of the pressure differential between the lower and upper sides of the diaphragm 1121.

The response of the diaphragm 1121 and the flow allowed through the primary flow port 1161 may be changed by changing the construction (e.g., the thickness, compliance, diameter, shape, and/or material selection) of the diaphragm 1121. For example, the diaphragm 1121 may be made out of a thinner or thicker material and/or the diaphragm 1121 may be made out of a less or more compliant material. As the thickness of the diaphragm 1121 approaches zero and the compliance of the diaphragm 1121 approaches infinity, the control assembly becomes more responsive to differences in pressure.

Figure 12A:
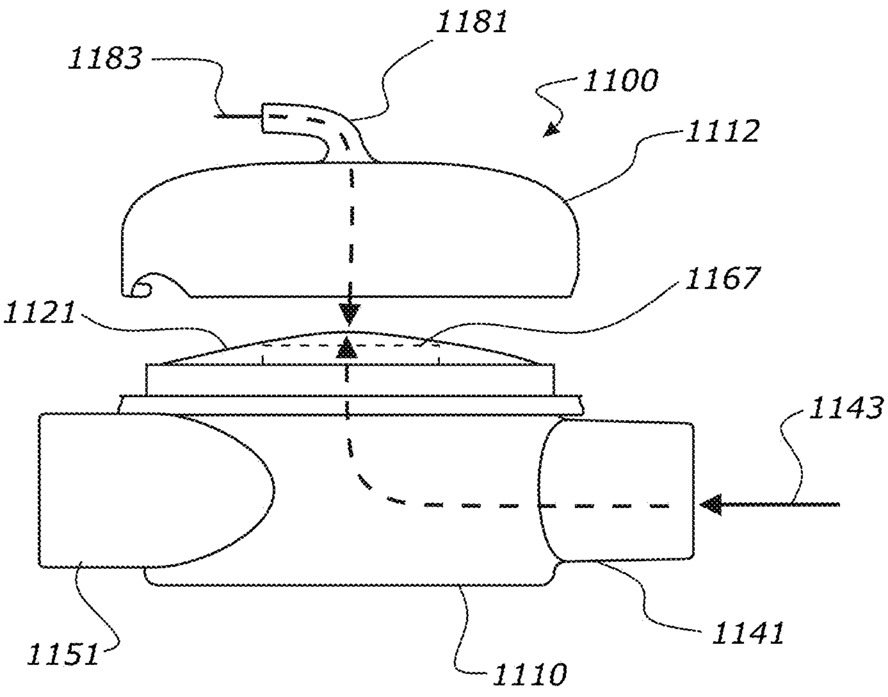
FIGS. 12A-12C show various views of the control assembly of FIGS. 11A-11C in a first operational configuration.
Figure 12B:
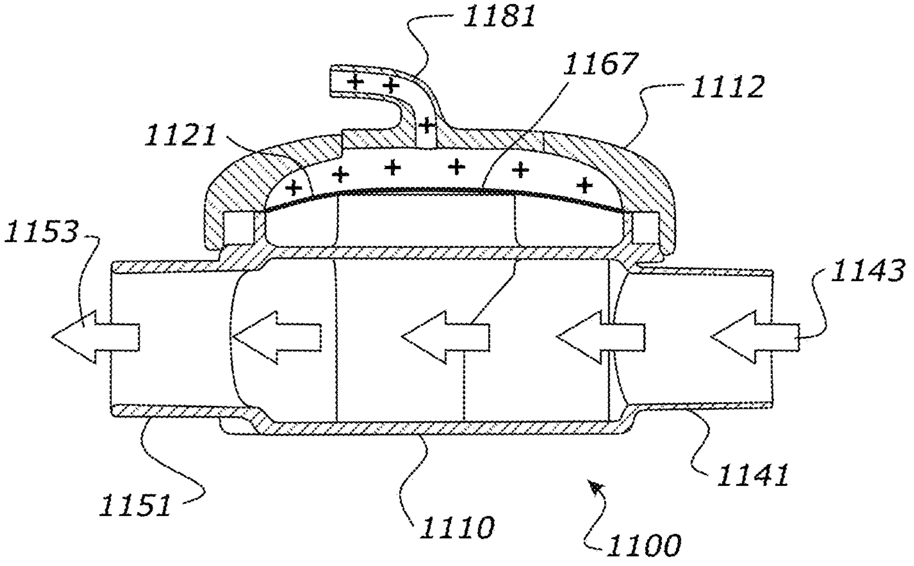
Figure 12C:
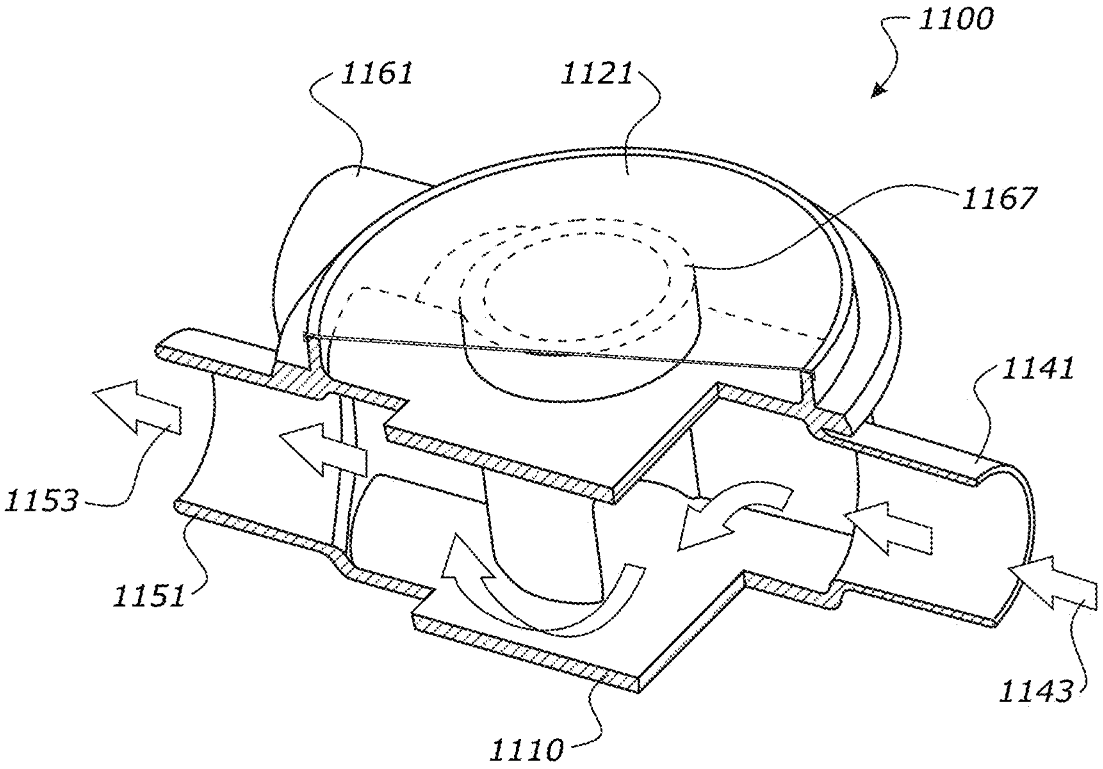

FIGS. 12A-12C illustrate flow of gases through the control assembly 1100 when the diaphragm 1121 is in a restricting position. FIG. 12B illustrates a cross-sectional view of the control assembly 1100 when the pressure on the lower side of the diaphragm 1121 (e.g., in the control assembly lower body 1110 or on the gas source side of the diaphragm 1121) is lower than the pressure on the upper side of the diaphragm 1121 (e.g., in the control assembly upper body 1112 or on the patient interface side of the diaphragm 1121). Ventilator gas flow 1143 is provided, e.g., by a ventilator, and enters the control assembly 1100 via the ventilator port 1141. When the pressure of the ventilator gas flow 1143 is less than the pressure within the control assembly upper body 1112, e.g., provided by the pressure feedback port 1181 (which may be the patient interface breathing chamber pressure less any pressure losses in the feedback port), the diaphragm 1121 is forced towards the ring end surface 1167 that defines the opening 1165 in the primary flow path. In FIGS. 12A-12C, the diaphragm 1121 is shown engaging the ring end surface 1167. However, this engagement may not be a scaling engagement in which case some gas will still pass between the ring wall and the diaphragm (and into the primary flow path). Nevertheless, in the illustrated configuration, the diaphragm 1121 is significantly restricting flow through the primary flow path. Thus, a substantial portion of the ventilator gas flow 1143 entering the ventilator port 1141 is forced to pass through the flushing flow path and out of the flushing flow port 1151 as flushing gas flow 1153. In some embodiments, the velocity of the flushing gas flow 1153 may not be higher or substantially higher than the velocity of the ventilator gas flow 1143 entering the ventilator port 1141. Instead, the flushing flow port 1151 may connect to a conduit which delivers the flushing gas flow 1153 to a final destination, e.g., a patient interface, where it is ultimately accelerated to a high velocity through such means as a cannula with reduced cross sectional area. The pressure feedback port 1181 may be connected, e.g., in pressure or fluid communication, to the breathing chamber of a patient interface. Therefore, the pressure in the control assembly upper body 1112, e.g., provided by the pressure feedback port 1181, may increase when the patient is exhaling, e.g., increasing the pressure within the breathing chamber of the patient interface relative to the pressure of the flow from the ventilator and hence in the control assembly lower body 1110. Thus, the diaphragm 1121 may be configured to move towards the closed or restricting configuration shown in FIGS. 12A-12C when the patient is exhaling.

Figure 12D:
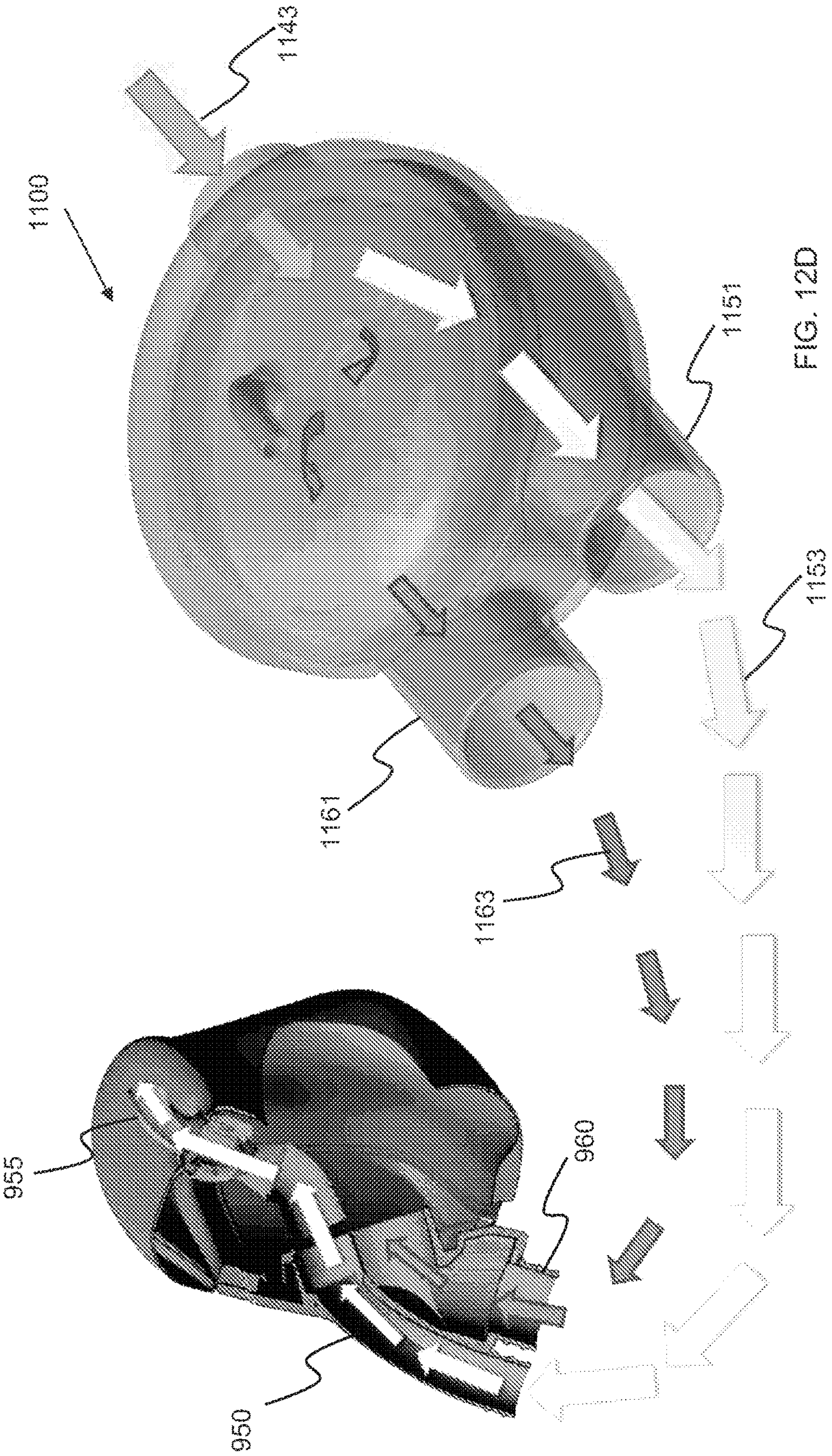
FIG. 12D shows the control assembly of FIGS. 11A-11C and the patient interface of FIG. 10, the interface shown in vertical cross-section, in a first operational configuration.

FIG. 12C illustrates a perspective cut-away view of the control assembly 1100 shown in FIG. 12B, except with the control assembly upper body 1112 removed. Ventilator gas flow 1143 enters the control assembly lower body 1110 of the control assembly 1100 through the ventilator port 1141. As shown in FIG. 12C, the diaphragm 1121 is in a restricting position (due to the pressure above the diaphragm 1121 being higher than the pressure below the diaphragm 1121, e.g., higher than the pressure of the ventilator gas flow 1143). Therefore, the ventilator gas flow 1143 entering the ventilator port 1141 is restricted by the diaphragm 1121 in/from flowing into the primary flow path and a substantial portion of the ventilator gas flow 1143 is forced through the flushing flow path and out of the control assembly 1100 through the flushing flow port 1151. As shown schematically in FIG. 12D the flushing gas flow 1153 travels to the patient interface 930 along the flushing flow path 950 including through and out of the pair of nasal prongs 955. As discussed elsewhere herein, nasal prongs may include a reduced cross-sectional dimension that serves to accelerate the flushing gas flow 1153 as it exits the flushing flow path, thereby creating a high velocity stream of gas that can be directed into the patient's nares. Such a high velocity stream of gas may advantageously flush, at least partially, at least one of an anatomical dead space, e.g., a nasal cavity, and an apparatus dead space. Because the diaphragm 1121 may not seal perfectly against the ring end surface 1167, at least some gas may travel through the primary flow path and out of the primary flow port 1161.

The gas flow out of the primary flow port 1161 travels to the patient interface along the primary flow path, where it enters through the mask body and into the breathing chamber of the patient interface. At least one of the flushing gas flow 1153 and the primary gas flow 1163 may contribute substantially to (e.g., generate and/or maintain) expiratory positive airway pressure (EPAP) and/or positive end expiratory pressure (PEEP) during exhalation.

Figure 13A:
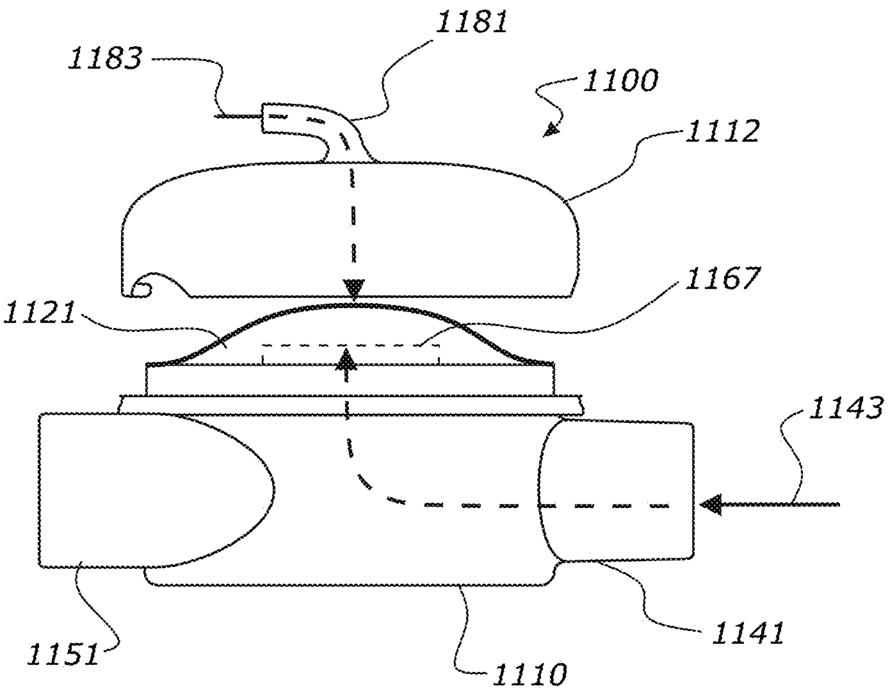
FIGS. 13A-13B show various views of the control assembly of FIGS. 11A-11C in a second operational configuration.
Figure 13B:
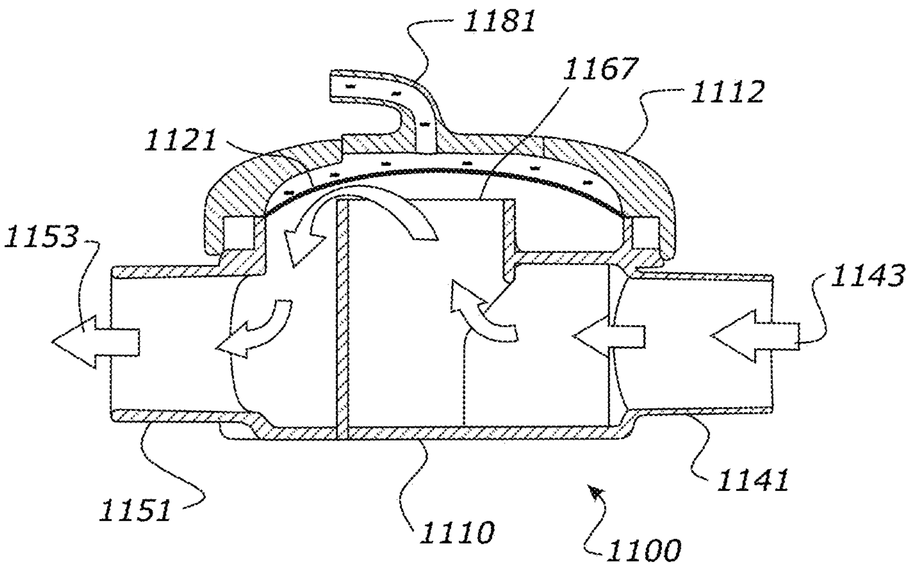
Figure 13C:
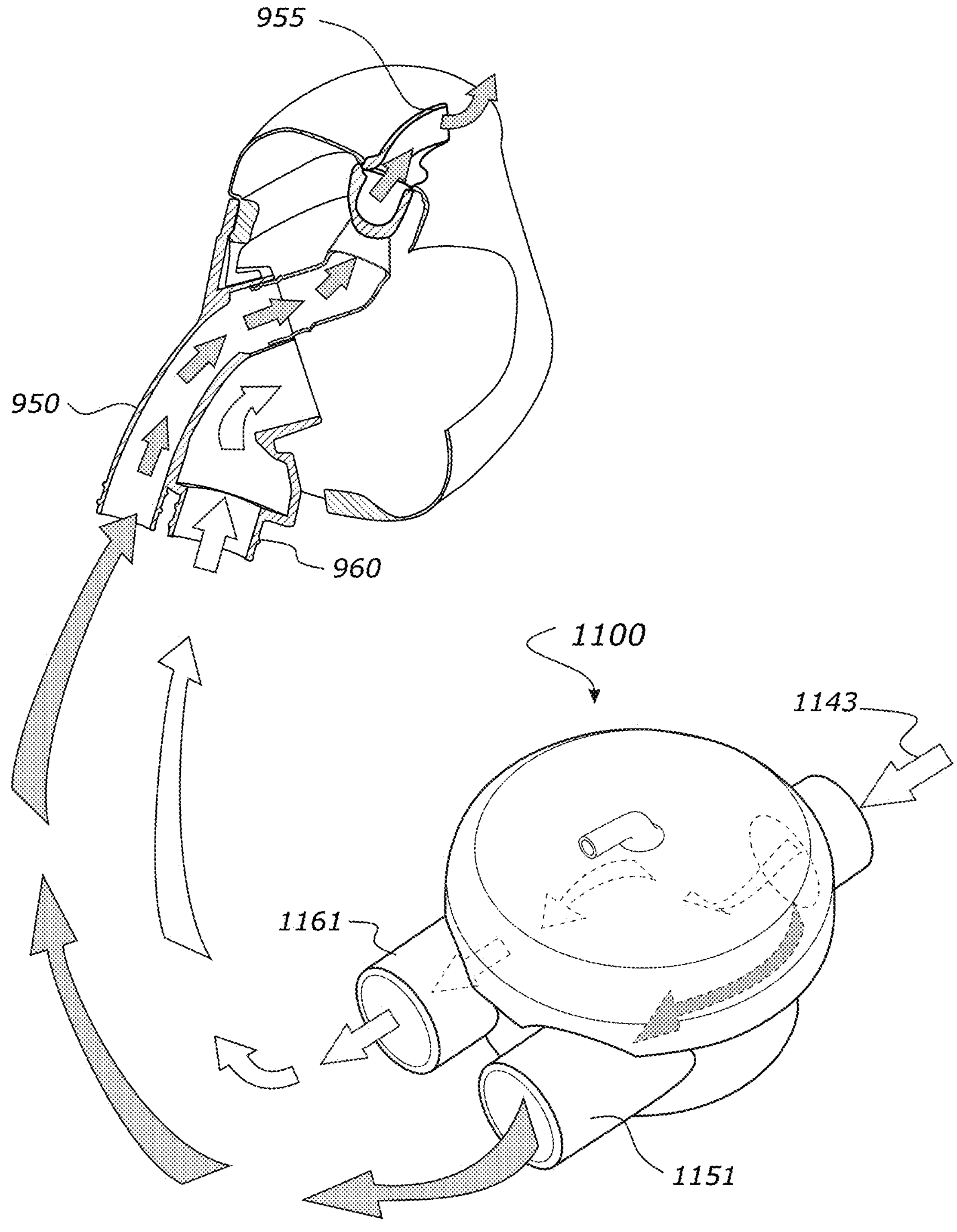
FIG. 13C shows the control assembly of FIGS. 11A-11C and the patient interface of FIG. 10, the interface shown in vertical cross-section, in a second operational configuration.

FIGS. 13A-13C illustrate the flow of gases through the control assembly 1100 when the diaphragm 1121 is in a relatively open position. FIG. 13B illustrates a cross-sectional view of the control assembly 1100 when the pressure on the lower side of the diaphragm 1121 (e.g., in the control assembly lower body 1110 or on the gas source side of the diaphragm) is higher than the pressure on the upper side of the diaphragm 1121 (e.g., in the control assembly upper body 1112 or on the patient interface side of the diaphragm). Ventilator gas flow 1143 enters the control assembly 1100 via the ventilator port 1141. When the pressure of the ventilator gas flow 1143 is greater than the pressure within the control assembly upper body 1112, e.g., provided by the pressure feedback port 1181 which is the patient interface breathing chamber pressure less any pressure losses in the feedback port, the diaphragm 1121 is forced away from the opening defined in the ring end surface 1167 so that gas is allowed to pass with relatively lower restriction through the opening and out of the primary flow port 1161. As discussed herein, the diaphragm 1121 may be at least partially responsive to the pressure within the control assembly lower body 1110, e.g., the higher the pressure within the control assembly lower body 1110 relative to the pressure in the control assembly upper body 1112, the more the diaphragm 1121 opens, and the more gas is allowed to pass through the opening to exit through the primary flow port 1161. The ventilator gas flow 1143 entering the ventilator port 1141 is split. A portion of the gases entering the ventilator port 1141 passes through the continuously unobstructed (or continuously open) flushing flow path and out of the flushing flow port 1151 as flushing gas flow 1153. With the diaphragm 1121 in an open or unrestricting position, a larger portion of the gases entering the ventilator port 1141 passes between the ring end surface 1167 and the diaphragm 1121, and out of the primary flow port 1161 as primary gas flow 1163 in the primary flow path. The pressure in the control assembly upper body 1112 provided by the pressure feedback port 1181 may decrease when the patient is inhaling due to a decrease in the pressure within the breathing chamber of the patient interface. Thus, the diaphragm 1121 is configured to move to a more open position when the patient is inhaling.

Because the diaphragm 1121 is open and the resistance to flow of the primary flow path is less than a resistance to flow of the flushing flow path, most of the ventilator gas flow 1143 is diverted through the opening, past the diaphragm 1121, and through the primary flow path to exit the primary flow port 1161 as the primary gas flow 1163. As discussed herein, the flushing flow path is always open, and a volume of gas may travel through that path, despite its higher resistance to flow (e.g., due to local or global restriction, such as nasal prongs or a comparatively smaller cross-sectional area). Therefore, a comparatively smaller volume of the ventilator gas flow 1143 leaves the control assembly 1100 through the flushing flow port 1151 when the diaphragm 1121 is not restricting flow into/through the primary flow path. During inhalation, when the diaphragm 1121 is in its substantially open position, the primary gas flow 1163 provides the majority contribution to the generation and/or maintenance of inspiratory positive airway pressure (IPAP) although the flushing gas flow may also contribute. The control assembly 1100 may interface with one or more components of the system for noninvasive ventilation as disclosed elsewhere herein.

FIGS. 14A-14B and 15A-15B illustrate a patient interface 1430 that incorporates a control assembly 1420. In other words, the patient interface 1430 is integrally formed with the control assembly. The patient interface 1430 of FIG. 14A may be similar in structure and function to the patient interface 930 of FIGS. 9A-9B. Structure for the patient interface 1430 may be provided, at least partially by a mask housing 1432 and a mask cushion 1431. The mask housing 1432 and the mask cushion 1431 together define a breathing chamber of the patient interface 1430. The mask housing 1432 and mask cushion 1431 form a cushion module. The mask housing 1432 is constructed of a rigid material such as polycarbonate or any other hard plastic while the mask cushion 1431 is constructed from a flexible material such as silicone. A frame 1434 is connected to the cushion module. The frame 1434 is also formed of a rigid material. The frame 1434 comprises a body that overlays an outer surface of the cushion module, a cushion module connector portion 1494, and a conduit connector portion 1490. The cushion module connector portion 1494 is in the form of a collar that extends rearward from the frame body 1433 and is shaped to be received in an aperture in the mask housing 1432. The frame 1434 may be permanently or removably connected to the cushion module. The conduit connector portion 1490 extends downwardly from the frame body 1433 at an angle to the cushion module connector portion 1494. The conduit connector portion 1490 has a generally cylindrical distal end that is configured to be connector to a generally cylindrical conduit of a breathing circuit so as to connect the patient interface to the gas source. The control assembly is incorporated into the frame 1434 of the patient interface. In particular, the control assembly is incorporated into the conduit connector portion 1490 of the frame 1434.

One or more components of the non-invasive ventilation system 1400 may correspond to the non-invasive ventilation system 900 of FIGS. 9A-9B. For example, the mask cushion 1431 may correspond to the mask cushion 931, the patient interface 1430 may correspond to the patient interface 930, the primary flow path 1460 may correspond to the primary flow path 960, and the flushing flow path 1450 may correspond to the flushing flow path 950. The patient interface 1430 may incorporate a nasal delivery portion which may incorporate a nasal cannula or nasal prongs, similar to those disclosed in connection with FIGS. 9A-9B. While some components may be similar, substantially similar, or even identical in structure and/or function between the non-invasive ventilation system 900 and the non-invasive ventilation system 1400 none are required to be similar, substantially similar, or identical.

Figure 14A:
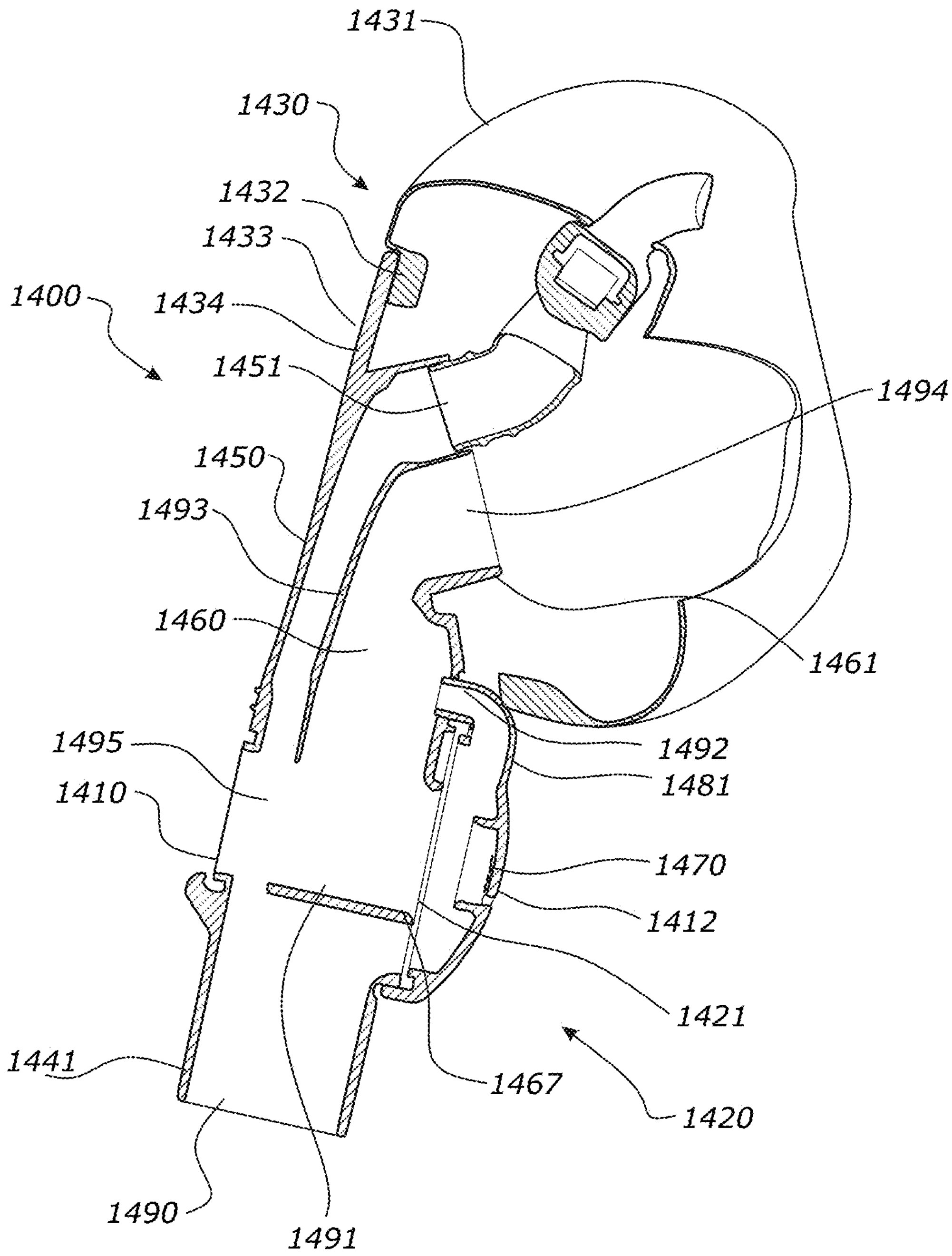
FIGS. 14A-14C show cross-sectional views of portions of an embodiment of a patient interface and a control assembly.

In much the same way, the control assembly 1420 of FIG. 14A may be similar in structure and function to the control assembly 1100 of FIGS. 11A-13C. The control assembly 1420 may include a control assembly lower body 1410 corresponding to the control assembly lower body 1110, a control assembly upper body 1412 corresponding to the control assembly upper body 1112, an inlet port 1441 corresponding to the ventilator port 1141, a flushing flow port 1451 corresponding to the flushing flow port 1151, a primary flow port 1461 corresponding to the primary flow port 1161, a pressure feedback port 1481 corresponding to the pressure feedback port 1181, and a diaphragm 1421 corresponding to the diaphragm 1121. While some components may be similar, substantially similar, or even identical in structure and/or function between the control assembly 1420 and the control assembly 1100, none are required to be similar, substantially similar, or identical.

In the patient interface 1430 of FIGS. 14A-14B and 15A-15B, the control assembly 1420 is located within the conduit connector portion 1490 that is configured to be permanently connected to the patient interface 1430. The conduit connector portion 1490 is permanently connected to the frame body 1433. The conduit connector portion 1490 may be fixed relative to the frame body 1433 or connected to the frame body 1433 via a rotatable connection such as a swivel or a ball and socket connection. Where the conduit connector portion 1490 is fixed to the frame body 1433, the conduit connector portion 1490 may comprise a swivel connection to the breathing circuit. A rotatable connection (either by the swivel connection to the breathing circuit or between the conduit connector portion 1490 and the mask body) enables rotation of a conduit of the breathing circuit that is connected to the patient interface 1430 in order to reduce the effects of hose pull and allow for flexibility in the patient's arrangement relative to the conduit. The conduit connector portion 1490 is generally constructed from the same material as the mask body 1432. The conduit connector portion 1490 is constructed from a hard plastic such as polycarbonate.

The conduit connector portion 1490 comprises an inlet port 1441 configured to be connected to a flow source, and two outlet ports, including a flushing flow port and a primary flow port 1461 configured to direct flow into at least one of the mask housing or patient's nares. Between the inlet and outlet ports there are formed two main flow paths; a flushing flow path 1450, formed between the inlet port 1441 and the flushing flow port, and a primary flow path 1460 formed between the inlet port 1441 and the primary flow port 1461. An exhaust vent 1470 is also provided on the conduit connector portion 1490 that is configured to exhaust gas from the cushion module to atmosphere. The conduit connector portion 1490 also comprises a pressure flow path that is configured to communicate pressure within the patient housing to one side of the control assembly.

The control assembly 1420 comprises a movable member in the form of a diaphragm 1421. The diaphragm 1421 is located within the conduit connector portion 1490 and is configured to affect both the flow through the primary flow path 1460 and flow through the exhaust vent 1470. The exhaust vent 1470 is formed at an end of a hollow or annular protrusion that protrudes inwardly on the conduit connector portion 1490 (e.g., protrudes from an inner surface of the conduit connect portion). The protrusion is generally cylindrical. The protrusion comprises an annular lip at one end configured to be used as a sealing surface. When the diaphragm 1421 is deformed towards the lip of the exhaust vent protrusion, flow through the exhaust vent 1470 will be restricted. The diaphragm 1421 will at least partially seal closed the exhaust vent 1470 if it contacts the sealing surface provided by the lip.

The control assembly 1420 comprises a second hollow or annular protrusion that protrudes towards the exhaust vent protrusion from an interior wall within the conduit connection portion. The second protrusion is located within the primary flow path 1460. The second protrusion is generally cylindrical. The second protrusion comprises an annular lip at one end configured to be used as a sealing surface. When the diaphragm 1421 is deformed towards the second lip, flow through the primary flow path 1460 will be restricted. This second lip is positioned opposite the exhaust vent lip. The diaphragm 1421 is located between the lips of the two protrusions of the control assembly and is configured to be able to be elastically deformed. The diaphragm 1421 thus can be deformed to substantially occlude either the exhaust vent 1470 or the primary flow path 1460, but only occluding one at a time.

The inlet port 1441 of the control assembly bifurcates into the flushing flow path 1450 and the primary flow path 1460 at a splitter arrangement 1495 provided within the conduit connector portion 1490. The flushing flow path 1450 originates at this bifurcation and passes through the conduit connector portion 1490 and into the mask housing unimpeded where it is configured to continue through a nasal delivery portion to be delivered to the patient's nares. The flushing flow path 1450 is always open and has no variable restrictions. The primary flow path 1460 also originates at this bifurcation and extends between the diaphragm 1421 and the second lip, through the second protrusion and continues to the primary flow outlet port which is open through the mask housing into the breathing chamber defined by the cushion module.

The splitter arrangement 1495 comprises a flushing flow path wall 1493 and a baffle 1491. The baffle 1491 is disposed within the conduit connector portion 1490 such that is substantially faces the inlet port 1441. In other words, the baffle 1491 is disposed in a plane that is substantially perpendicular to the flow of gas into the conduit connector portion 1490. The baffle 1491 extends partially across the width of the conduit connector portion 1490. A portion of the second protrusion that provides the lip against which the diaphragm can restrict flow through the primary flow path 1460 is provided by the baffle 1491.

The flushing flow path wall 1493 extends along a substantial portion of the length of the conduit connector portion 1490. The flushing flow path wall 1493 extends from the baffle 1491 to the cushion module connector portion 1494 of the frame 1434. The flushing flow path wall 1493 is located within the conduit connector portion 1490 and is opposed to an outer wall of the of the conduit connector portion 1490. The flushing flow path wall 1493 thus forms a separate gas space within the conduit connector portion 1490. The flushing flow path wall 1493, together with a portion of the cushion module connector portion 1494 of the frame 1434, forms the flushing flow port 1451.

The control assembly 1420 also comprises a cavity 1492 on the exhaust vent side of the diaphragm 1421 that is open to the primary flow path 1460 close to the inlet to the cushion module (e.g., is close to the primary flow port 1461). The cavity 1492 defines at least a portion of the primary flow path 1460 and is configured to communicate a gas pressure that is sufficiently similar to the pressure within the cushion module. The pressure flow path passes from the primary flow path 1460 and connects with the cavity 1492 such that it communicates the pressure within the mask housing to the exhaust vent side of the diaphragm 1421. The cavity 1492 comprises a side chamber extending from the primary flow path 1460. The side chamber is located adjacent to and below the cushion module. The side chamber forms a rearward extension of the conduit connector portion 1490. The side chamber is in fluid communication with the hollow or annular protrusion of the exhaust vent 1470.

In this way the diaphragm 1421 experiences pressure on both sides with the pressure on one side being the same or closely similar to the internal pressure of the cushion module communicated via the pressure flow path and the pressure on the second side being the pressure supplied by the gas source minus any pressure losses between the gas source and the diaphragm 1421.

Figure 14B:
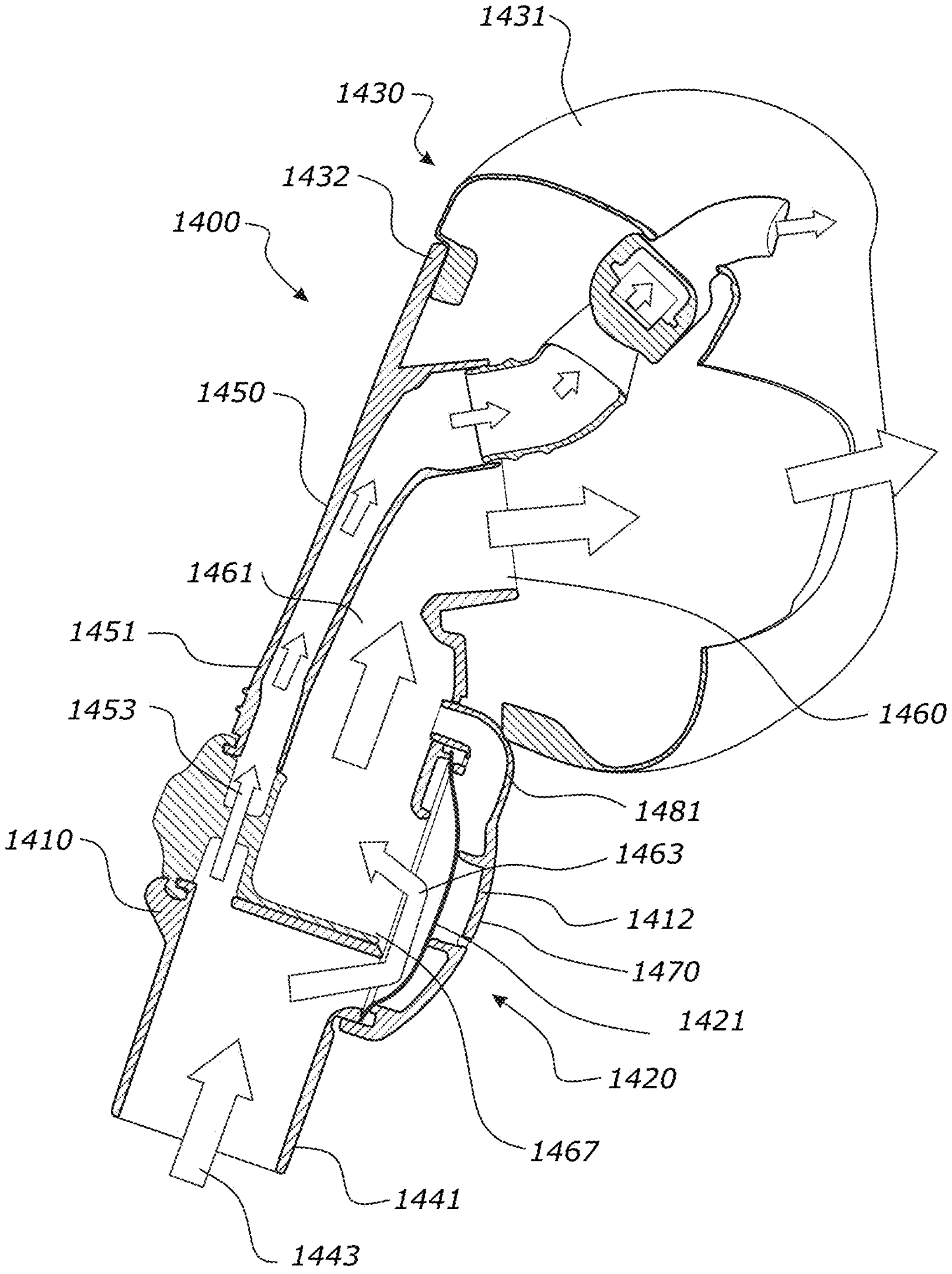
Figure 14C:
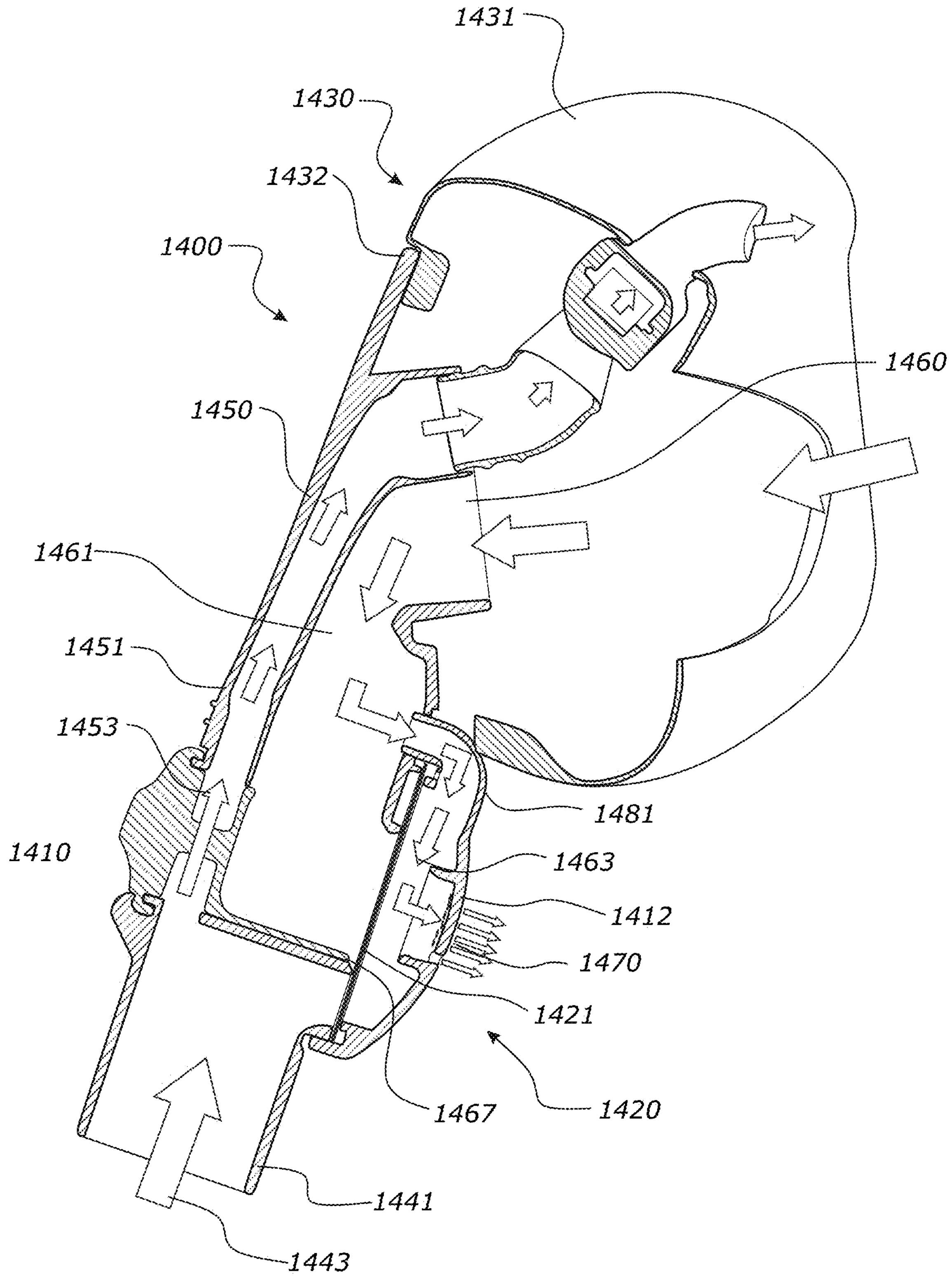
Figure 15B:
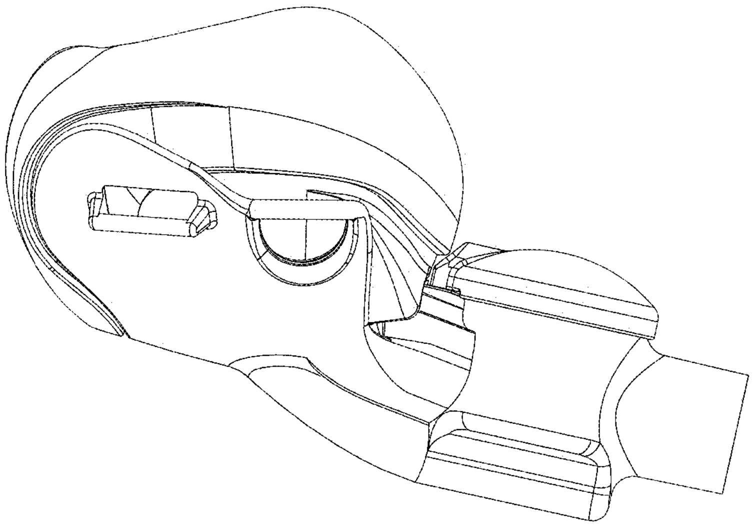
FIGS. 15A-15B show various views of portions of an embodiment of a patient interface and a control assembly.
Figure 15A:
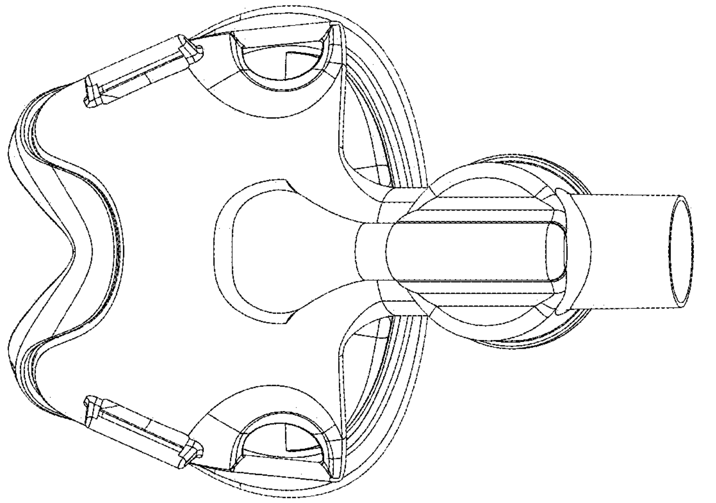

The non-invasive ventilation system 1400 may be similar to the systems shown in FIGS. 17A-17D (as shown in FIGS. 14A-14C), except that the control assembly 1420 is integrated with the patient interface 1430 as a single unit. When similar to FIGS. 17A-17D, the non-invasive ventilation system 1400 vents gases to atmosphere at least through, e.g., primarily through, a vent in the control assembly 1420 (e.g., a vent in the control assembly upper body 1412 of the control assembly 1420) similar to the exhaust vent 1770 shown in FIGS. 17A-17D. The non-invasive ventilation system 1400 may be similar to the systems shown in FIGS. 12D and 13C, except that the control assembly 1420 is integrated with the patient interface 1430 as a single unit. When similar to FIGS. 12D and 13C, the non-invasive ventilation system 1400 vents gases via a vent in the patient interface, similar to the exhaust vent 970 shown in FIGS. 12D and 13C. The integrated control assembly 1420 and patient interface 1430 provides for a more compact system that is easier to set up and use as there are less connections to be made between system parts.

FIG. 14B illustrates a cross-sectional view of the control assembly control assembly 1420 when the pressure on the lower side of the diaphragm 1421 (e.g., in the control assembly lower body 1410 or the gas source side of the diaphragm) is higher than the pressure on the upper side of the diaphragm 1421 (e.g., in the control assembly upper body 1412 or the patient interface side of the diaphragm) and the diaphragm 1421 is in a less restricting position. FIG. 14B shows the non-invasive ventilation system 1400 when a patient is inhaling, causing the pressure in the breathing chamber of the patient interface 1430 to decrease. The pressure drop in the breathing chamber of the patient interface 1430 is communicated to the control assembly 1420 via the pressure feedback port 1481. In its less restricting position, the diaphragm 1421 allows gas to flow through the primary flow path 1460, e.g., past the diaphragm 1421, through the primary flow path 1460, and into the breathing chamber of the patient interface 1430 (as discussed, some gas may also flow through the flushing flow path 1450). The behavior of the control assembly 1420 and its components may be similar to the control assembly 1100 described in connection with FIG. 12B. The pressure in the control assembly upper body 1412 (e.g., in the volume of the control assembly 1420 towards the patient interface from the diaphragm 1421) is determined by the pressure feedback port 1481. The pressure feedback port 1481 in the illustrated embodiment of FIG. 14B is in fluid communication with primary flow path 1460 upstream of the diaphragm 1421. However, the connection of the pressure feedback port 1481 is sufficiently close to an outlet of the primary flow path 1460 into breathing chamber of the patient interface 1430 such that the pressure drop between the pressure feedback port 1481 and the breathing chamber of the patient interface 1430 is not significant enough to affect performance of the system. In some embodiments, the pressure feedback port 1481 is directly connected to the breathing chamber of the patient interface 1430.

As can be seen, when a patient inhales, the pressure in the patient interface 1430 drops, thereby lifting the diaphragm 1421 off the ring end surface 1467 (lessening the restriction of flow through the primary flow path 1460) and up against the vent 1470 (increasing the restriction of flow through the vent 1470). As the diaphragm 1421 lifts off the ring end surface 1467 an increased volume of gas is permitted to flow past the diaphragm 1421, through the primary flow path 1460, and into the patient interface. As the diaphragm 1421 rises towards and restricts the vent 1470, a decreased volume of gas is permitted to escape through the vent 1470. Similar to the control assembly 1720 discussed in connection with FIGS. 17A-17E, the diaphragm 1421 of the control assembly 1420 may have two extreme positions. In one of the diaphragm's 1421 extreme positions, the diaphragm 1421 is as close as possible to the ring end surface 1467, e.g., touching the ring end surface 1467, and as far away as possible from the exhaust vent 1470 sealing ring (similar to exhaust vent scaling ring 1777). When the diaphragm 1421 is as close as possible to the ring end surface 1467, the diaphragm 1421 restricts flow of gases through the primary flow path 1460. When the diaphragm 1421 is as far away as possible from the exhaust vent 1470 sealing ring, the diaphragm 1421 permits unimpeded flow of gases through the exhaust vent 1470. In the other of the diaphragm's 1421 extreme positions, the diaphragm 1421 is as close as possible to the exhaust vent 1470 scaling ring, e.g., touching the ring, and as far away as possible from the ring end surface 1467. When the diaphragm 1421 is as close as possible to the exhaust vent 1470 sealing ring, the diaphragm 1421 restricts flow of gases through or out of the exhaust vent 1470. When the diaphragm 1421 is as far away as possible from the ring end surface 1467, the diaphragm 1421 permits unimpeded flow of gases through the primary flow path 1460.

FIG. 14C illustrates a cross-sectional view of the control assembly control assembly 1420 when the pressure on the lower side of the diaphragm 1421 (e.g., in the control assembly lower body 1410 or the gas source side of the diaphragm) is lower than the pressure on the upper side of the diaphragm 1421 (e.g., in the control assembly upper body 1412 or the patient interface side of the diaphragm) and the diaphragm 1421 is in a restricting position. FIG. 14C shows the non-invasive ventilation system 1400 when a patient is exhaling, causing the pressure in the breathing chamber of the patient interface 1430 to increase. The pressure increase in the patient interface 1430 is communicated to the control assembly 1420 via the pressure feedback port 1481. In its restricting position, the diaphragm 1421 approaches the ring end surface 1467 and restricts gas flow through the primary flow path 1460, thereby forcing the gas to flow through the flushing flow path 1450 (as discussed, the diaphragm 1421 may not sealingly engage the ring end surface 1467 and gas may continue to flow through the primary flow path 1460, even when the diaphragm 1421 is in its restricting position). As can be seen, when a patient exhales, the pressure in the patient interface 1430 increases, pushing the diaphragm 1421 towards the ring end surface 1467 (increasing the restriction of flow through the primary flow path 1460) and away from the vent 1470 (decreasing the restriction of flow through the vent 1470). As the diaphragm 1421 is pushed towards the ring end surface 1467, the diaphragm 1421 restricts the flow of gas through the primary flow path thereby allowing a comparatively decreased volume of gas is permitted to flow past the diaphragm 1421, through the primary flow path 1460, and into the patient interface. As the diaphragm 1421 falls or moves away from the vent 1470, gases are more freely permitted to escape through the vent 1470 to atmosphere. In this case, the pressure feedback port 1481 doubles as a leak path for gas to escape through the exhaust vent 1470 and out of the mask to atmosphere. Decreased flow of gases through the primary flow path 1460 corresponds to a correspondingly increased flow of gases through the flushing flow path 1450. As is discussed elsewhere herein, the flushing flow path 1450 may be configured to accelerate the flushing gas flow 1453 passing through the flushing flow path 1450. The accelerated flushing gas flow 1453 may exit the flushing flow path 1450 via one or more nasal prongs and may flush at least a portion (e.g., some or all) or one or more of an anatomical dead space and an apparatus dead space. Gases being exhaled by the patient may travel through the primary flow port 1461, through the pressure feedback port 1481, and out of the exhaust vent 1470, incorporated into the control assembly upper body 1412. Some embodiments of the flow controlling patient interface 1400 incorporate an exhaust vent 1470 in the control assembly upper body 1412 of the control assembly 1420 and in the mask housing 1432. Some embodiments of the flow controlling patient interface 1400 incorporate an exhaust vent 1470 in only the control assembly upper body 1412 of the control assembly 1420.

Figure 16:
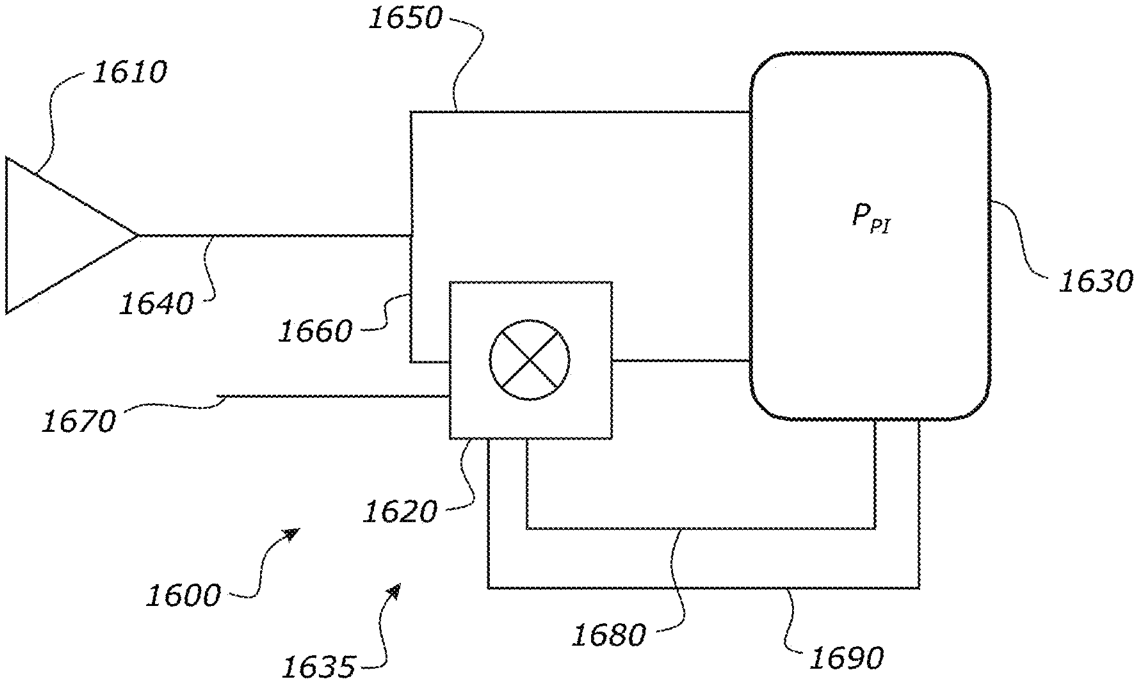
FIG. 16 is a block diagram of an embodiment of a system that may be used for noninvasive ventilation.

FIG. 16 illustrates a block diagram of an embodiment of a system for providing and/or maintaining noninvasive ventilation. The noninvasive ventilation system 1600 includes various components, including a gas source 1610, a control assembly 1620, a patient interface 1630, a breathing circuit 1635, and a feedback arrangement 1680. Such components define a gas source conduit 1640, a primary flow path 1660 and a flushing flow path 1650. The components of the noninvasive ventilation system 1600 may be substantially similar to the components of the noninvasive ventilation system 800 discussed in connection with FIG. 8 and the noninvasive ventilation system 200 discussed in connection with FIG. 2A. For example, the gas source 1610 may correspond to the gas source 810, the gas source conduit 1640 may correspond to the gas source conduit 840, the primary flow path 1660 may correspond to the 860, the flushing flow path 1650 may correspond to the flushing flow path 850, the control assembly 1620 may correspond to the control assembly 820, the patient interface 1630 may correspond to the patient interface 830, and the feedback arrangement 1680 may correspond to the feedback arrangement 880. While some components may be similar, substantially similar, or even identical between the noninvasive ventilation system 800 and the noninvasive ventilation system 200, none are required to be similar, substantially similar, or identical.

The gas source 1610 has an outlet connected to the breathing circuit 1635 by which the gas source supplies breathing gas. The pressure and flow at the outlet of the gas source are nominally a first pressure, P1 and a first volumetric flow rate, F1. The gas source 1610 is controlled to provide a first pressure and first flow rate (P1, F1) to achieve a desired pressure at the patient interface 1630, in particular in a breathing chamber of a mask. The first pressure and first flow rate (P1, F1) may therefore be controlled to account for any system pressure losses between the gas source 1610 and the patient interface 1630. As previously mentioned, the desired pressure at the patient interface 1630 may vary during the user's respiration cycle (e.g., between an IPAP and an EPAP).

The breathing circuit 1635 divides, bifurcates, or splits into the flushing flow path 1650 and the primary flow path 1660, each flow path having separate outlets in the patient interface 1630 through which breathing gas is delivered to the user. The pressure and flow at the outlet of the flushing flow path 1450 are nominally a second pressure, P2 and a second volumetric flow rate, F2. The pressure and flow at the outlet of the primary flow path 1460 are nominally a third pressure, P3 and a third volumetric flow rate, F3.

The feedback arrangement 1680 is in the form of a connection, port, or line that communicates the pressure within the breathing chamber of the patient interface 1630 to the control assembly 1620. The control assembly 1620 may modulate the flow allowed through the primary flow path 1660 based on the pressure of the gas within the patient interface 1630, e.g., the pressure communicated to the control assembly 1620 by the pressure arrangement line 1680.

The control assembly 1620, at least in part, defines the inlet to the primary flow path 1660 from the gas source 1610. The flushing flow path 1650 is connected to the gas source 1610 via a set flow path that is not directly changed or modified by the control assembly 1620 (though it may be indirectly changed and/or modified). The control assembly 1620 has a gas source side and a patient interface side. The gas source side of the control assembly 1620 includes an inlet to the control assembly 1620. The patient interface side of the control assembly 1620 includes the pressure line 1680. The control assembly 1620 is configured to vary the flow resistance of the primary flow path 1660. The control assembly 1620 is operable such that when the pressure on the gas source side of the control assembly 1620 (generally corresponding to P1 less any pressure losses between the gas source outlet and the control assembly) is higher than pressure on the patient side of the control assembly 1620 (generally corresponding to the pressure in the patient interface breathing chamber less any pressure loss across the pressure feedback arrangement 1680), flow through the primary flow path 1660 is open or less restricted by the control assembly 1620. The greater the pressure differential between the gas source side and the patient interface side of the control assembly 1620 (with the gas source side being a higher pressure than the patient interface side), the less restricted the primary flow path 1660 will be.

The control assembly 1620 is also operable such that when pressure on the patient interface side of the control assembly 1620 (generally corresponding to the pressure in the patient interface breathing chamber less any pressure loss across the pressure feedback arrangement 1680) is greater than the pressure on the gas source side of the control assembly 1620 (generally corresponding to P1 less any pressure losses between the gas source outlet and the control assembly), flow through the primary flow path 1660 is restricted or more restricted by the control assembly 1620. The greater the positive pressure differential between the patient interface side and the gas source side, the more restricted the flow through the primary flow path 1660 may be.

When the control assembly restricts flow through the primary flow path 1660, for the same pressure (P1) at the outlet of the gas source, the flow (F3) through the outlet of the primary flow path 1660 is reduced and the flow (F2) through the outlet of the flushing flow path 1650 is increased. As the volumetric flow rate through the flushing flow path 1650 is increased the velocity of the gas flow through the flushing flow path 1650 is also increased. The system is configured so that the velocity of the gas flow through the flushing flow path 1650 is sufficiently high enough for a sufficient duration of the user's breathing cycle to achieve flushing of the anatomical and/or apparatus dead space. Similarly, when the control assembly 1620 opens flow through the primary flow path 1660, for the same pressure (P1) at the outlet of the gas source 1610, the flow (F3) through the outlet of the primary flow path 1660 is increased and the flow (F2) through the outlet of the flushing flow path 1650 is decreased due to the lowered resistance to flow through the primary flow path 1660.

An increase in pressure on the patient interface side of the control assembly 1620 relative to the pressure on the gas source side of the control assembly 1620 generally occurs during user exhalation. This is because the user is breathing out and adding mass to the fixed volume of gas in the patient interface 1630 and thus increasing the pressure in the patient interface breathing chamber. During user inhalation, the pressure on the patient interface side of the control assembly 1620 is usually lowered relative to the pressure on the gas source side of the control assembly 1620 because the user is drawing air in from the patient interface 1630. As a result, the system may be configured to provide flushing of the anatomical and/or apparatus dead space mostly during exhalation and may rarely, if at all provide flushing during inhalation. The noninvasive ventilation system 1600 also comprises a venting flow path 1690. The venting flow path 1690 is configured to provide a flow path for gas to vent from the patient interface 1630 through the control assembly 1620. In some embodiments, the venting flow path 1690 may be combined with the feedback arrangement 1680, e.g., there is not a separate venting flow path 1690 and feedback arrangement 1680, but rather a single conduit that communicates both pressure and venting flow between the patient interface 1630 and the control assembly 1620. When the patient exhales, the expired gases are collected by the breathing chamber of the patient interface 1630 and passed out of the breathing chamber through the venting flow path 1690 to the control assembly 1620. After arriving at the control assembly 1620, expired or exhaled gases may affect performance of the control assembly 1620 and/or the expired or exhaled gases may be vented from the control assembly 1620 to the atmosphere. For example, expired or exhaled gases may be expired to atmosphere if the pressure of the exhaled gasses is higher than the pressure of flow being received by the control assembly 1620 from the gas source. In this way, the control assembly 1620 may be dynamically responsive to the breathing cycle of the patient.

In some embodiments, the noninvasive ventilation system 1600 provides for active venting of expired gases. The control assembly 1620 may be configured to close or restrict flow through the venting flow path 1690 when the pressure in the patient interface (PPI) is less than a pressure in another part of the system. In some embodiments, the control assembly 1620 is configured to close or restrict flow through the venting flow path 1690 when the pressure in the patient interface (PPI) is less than the first pressure (P1) of the gas flow at outlet of the gas source less any pressure losses between the gas source and the control assembly. In other words, the venting flow path 1690 is closed or restricted when the pressure on the patient interface side of the control assembly is less than the pressure on the gas source side of the control assembly. Closing or restricting flow through the venting flow path 1690 when the pressure in the patient interface (PPI) is comparatively low may advantageously prevent atmospheric air from being drawn into the system, through the venting flow path 1690, in response to the lower pressure in the patient interface (PPI). It also means the gas source does not have to overcome the vent leak during inhalation and so does less work overall while supplying the patient with the same pressure of gas. The control assembly 1620 may be configured to open or reduce the restriction on the venting flow path 1690 when the pressure in the patient interface (PPI) is greater than a pressure in another part of the system. In some embodiments, the control assembly 1620 is configured to open or reduce the restriction on the venting flow path 1690 when the pressure in the patient interface (PPI) is greater than the first pressure (P1) of the gas flow at outlet of the gas source less any pressure losses between the gas source and the control assembly. In other words, the venting flow path 1690 is opened or the restriction reduced when the pressure on the patient interface side of the control assembly is greater than the pressure on the gas source side of the control assembly.

FIGS. 17A-17E illustrate an embodiment of a control assembly 1720 that may form part of various noninvasive ventilation systems disclosed herein, e.g., the noninvasive ventilation system 1600 shown in FIG. 16. The control assembly 1720 of FIGS. 17A-17D includes various components that may be substantially similar to the components of the control assembly 1100 of FIGS. 11A-11B. For example, the control assembly lower body 1710 may correspond to the control assembly lower body 1110, the inlet flow port 1741 may correspond to the ventilator port 1141, the flushing flow port 1751 (not shown in certain of FIGS. 17A-17D) may correspond to the flushing flow port 1151, the opening in the primary flow path and associated primary flow sealing surface 1767 may correspond to the opening and primary flow sealing surface 1167, and the diaphragm 1721 may correspond to the diaphragm 1121. While some components may be similar, substantially similar, or even identical in structure and/or function between the control assembly 1720 and the control assembly 1100, none are required to be similar, substantially similar, or identical. For example, the control assembly 1720 of FIGS. 17A-17D may differ from the control assembly 1100 of FIGS. 11A-11B in the structure and functionality of its control assembly upper body 1712.

As discussed herein, the control assembly upper body 1112 of the control assembly 1100 serves as a cap for the control assembly lower body 1110 that covers the diaphragm 1121. Pressure changes in the control assembly upper body 1112 relative to the pressure in the control assembly lower body 1110 cause the diaphragm 1121 to increase and decrease the restriction applied by the diaphragm to flow through the primary flow path. These changes result in the changes in the relative volumetric flow rates of gas through the primary flow path and the flushing flow path.

The control assembly 1720 includes a pressure feedback port 1781 that guides gases from a breathing chamber of a patient interface into the control assembly upper body 1712. The pressure feedback port 1781 may be configured to accept a feedback gas flow 1783, which may comprise some, substantially all, or all of the gases exhaled by the patient (e.g., the patient interface connected to the control assembly 1720 may be sealingly attached to the patient's face and configured such that most or all of the gases exhaled into the patient interface are forced to pass to the pressure feedback port 1781 as feedback gas flow 1783). Pressure changes in the control assembly upper body 1712 (e.g., due to fluid (e.g., pressure) communication between the control assembly upper body 1712 and the breathing chamber of a patient interface through the pressure feedback port 1781) may cause the diaphragm 1721 to move towards or away from an opening in the primary flow path. When the pressure of the ventilator gas flow 1743 is less than the pressure within the control assembly upper body 1712, e.g., provided by the pressure feedback port 1781 which is the patient interface breathing chamber pressure less any pressure losses in the feedback port, the diaphragm 1721 is forced towards the primary flow sealing surface 1767 that defines the opening in the primary flow path. This limits flow through the primary flow path out of the primary flow port 1761 and, provided a large restriction in the primary flow path is created, causes a significant portion of the flow from the ventilator to travel only through the flushing flow path.

When the pressure of the ventilator gas flow 1743 is greater than the pressure within the control assembly upper body 1712, e.g., provided by the pressure feedback port 1781 which is the patient interface breathing chamber pressure less any pressure losses in the feedback port, the diaphragm 1721 is forced away from the primary flow sealing surface 1767 that defines the opening in the primary flow path. Opening the primary flow path to the extent that the diaphragm is not significantly limiting flow through the primary flow path causes the majority of the ventilator gas flow to flow along the primary flow path in preference to the flushing flow path due to the greater resistance to flow of the flushing flow path.

Figure 17A:
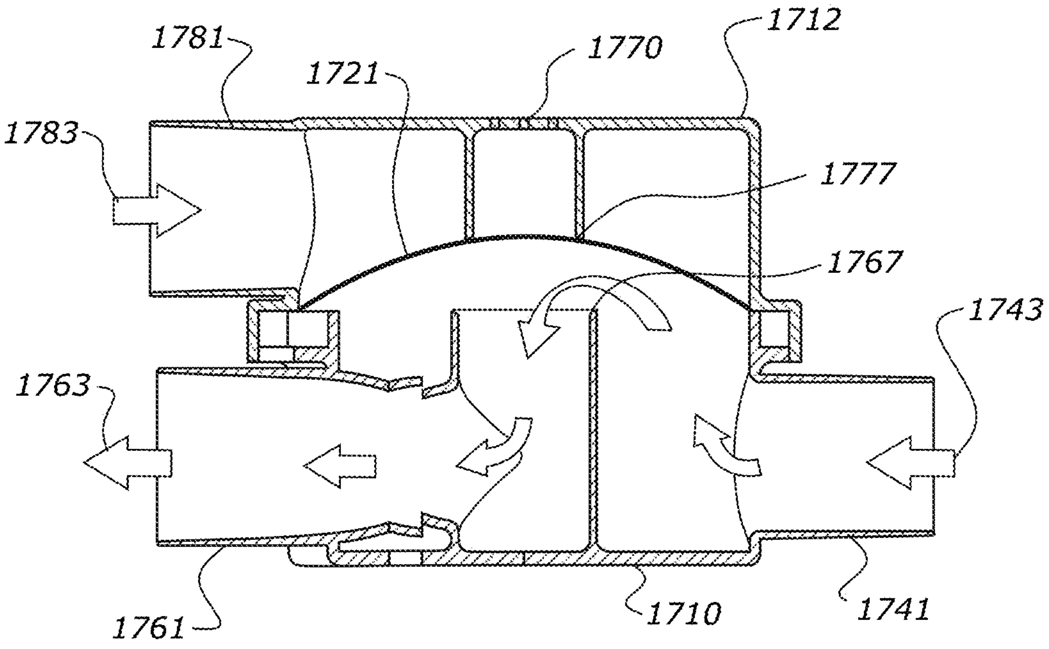
FIGS. 17A-17E show various cross-sectional views of an embodiment of a control assembly.
Figure 17B:
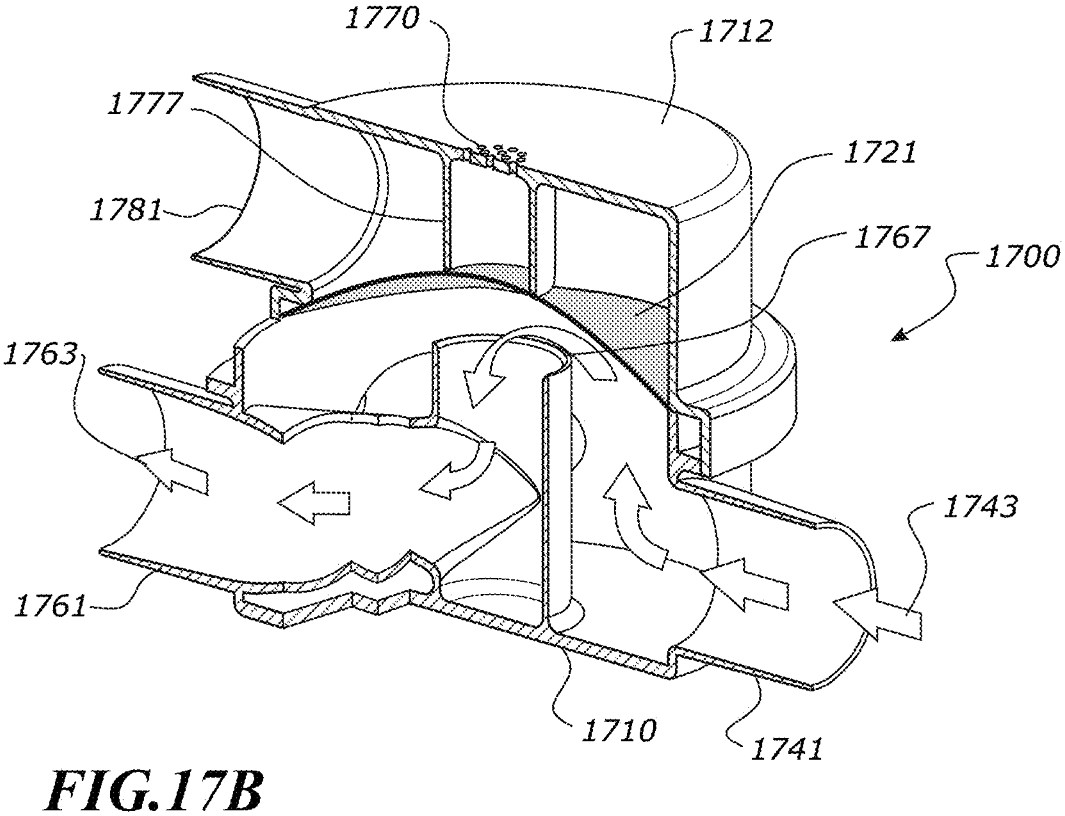

The control assembly upper body 1712 may also include an exhaust vent 1770 having a vent opening and an exhaust vent sealing surface 1777. The exhaust vent 1770 may serve to vent air exhaled by the patient and received in the control assembly from the patient interface through the pressure feedback port 1781. The vent opening is formed in the exhaust vent sealing surface 1777. The ability to vent may be particularly advantageous when the exhaust vent 1770 is connected to a sealing (or substantially sealing) patient interface, e.g., an interface that seals against the patient's face, that does not incorporate a vent. The exhaust vent sealing surface 1777 may be configured to be sealingly engaged by the diaphragm 1721 to close the vent opening when the diaphragm 1721 is in an open position and not restricting flow through the primary flow path. As shown in FIGS. 17A-17B, when the diaphragm 1721 is in its fully open position (e.g., allowing gas to travel through the primary flow path and out of the primary flow port 1761 without restriction), the diaphragm 1721 is raised up toward the control assembly upper body 1712 and against the exhaust vent sealing surface 1777. When the diaphragm 1721 is in sealing engagement with the exhaust vent sealing surface 1777, gases received through the pressure feedback port 1781, e.g., exhalation gases, are not permitted to vent out of the exhaust vent 1770 (or only a small volume of gases are permitted to vent). As the diaphragm 1721 begins to close or restrict flow through the primary flow path, the diaphragm 1721 moves away from the exhaust vent sealing surface 1777 and toward the primary flow sealing surface 1767. As this occurs, the venting flow path is opened, allowing gases received through the pressure feedback port 1781 to leave the control assembly 1720 through the exhaust vent 1770.

During inhalation, e.g., shown in FIGS. 17A-17B, the patient's inspiration of gases decreases the pressure within the breathing chamber of the patient interface (e.g., relative to the gas flow from the ventilator). Decreased pressure in the breathing chamber of the patient interface is communicated to the control assembly 1720 through the pressure feedback port 1781 and causes the pressure in the control assembly upper body 1712, above the diaphragm 1721, to drop relative to the pressure below the diaphragm. When this occurs, the diaphragm 1721 may open (either partially or substantially), as discussed herein, and a large proportion of the gases received from a ventilator are allowed to pass through the primary flow path, out of the primary flow port 1761 and to the patient interface. When the diaphragm 1721 is open, the upper side of the diaphragm 1721 restricts or closes the vent opening in the exhaust vent sealing surface 1777, e.g., in sealing or substantially scaling engagement against the exhaust vent sealing surface 1777. This restricts leak of gas from the patient interface through the venting flow path during inhalation.

Figure 17C:
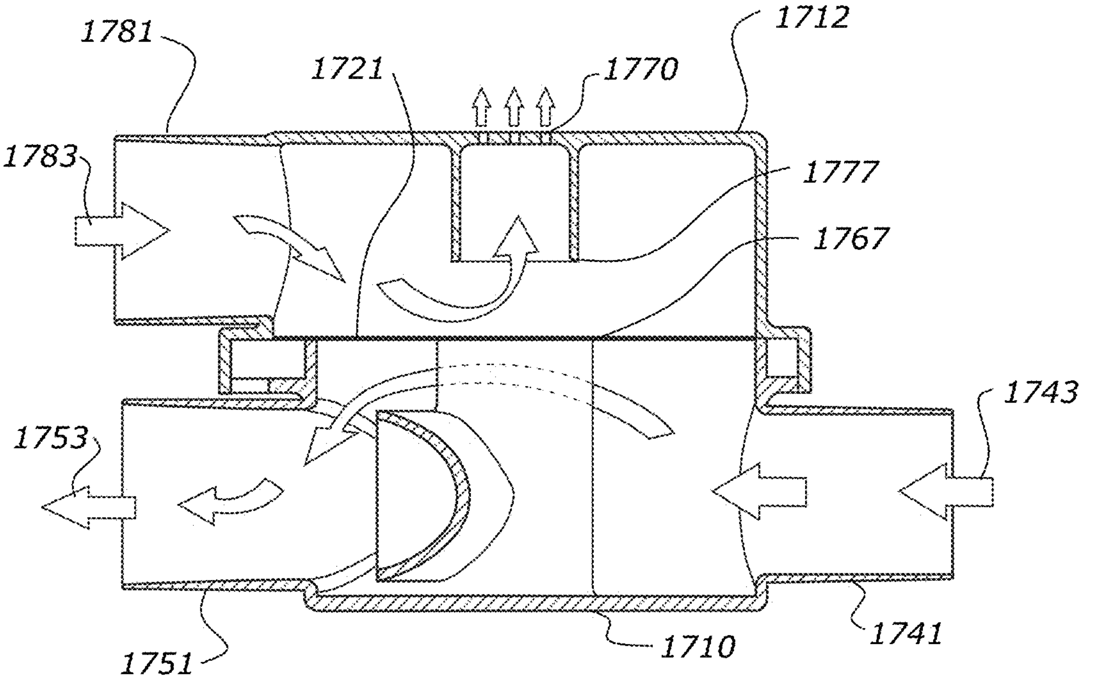
Figure 17D:
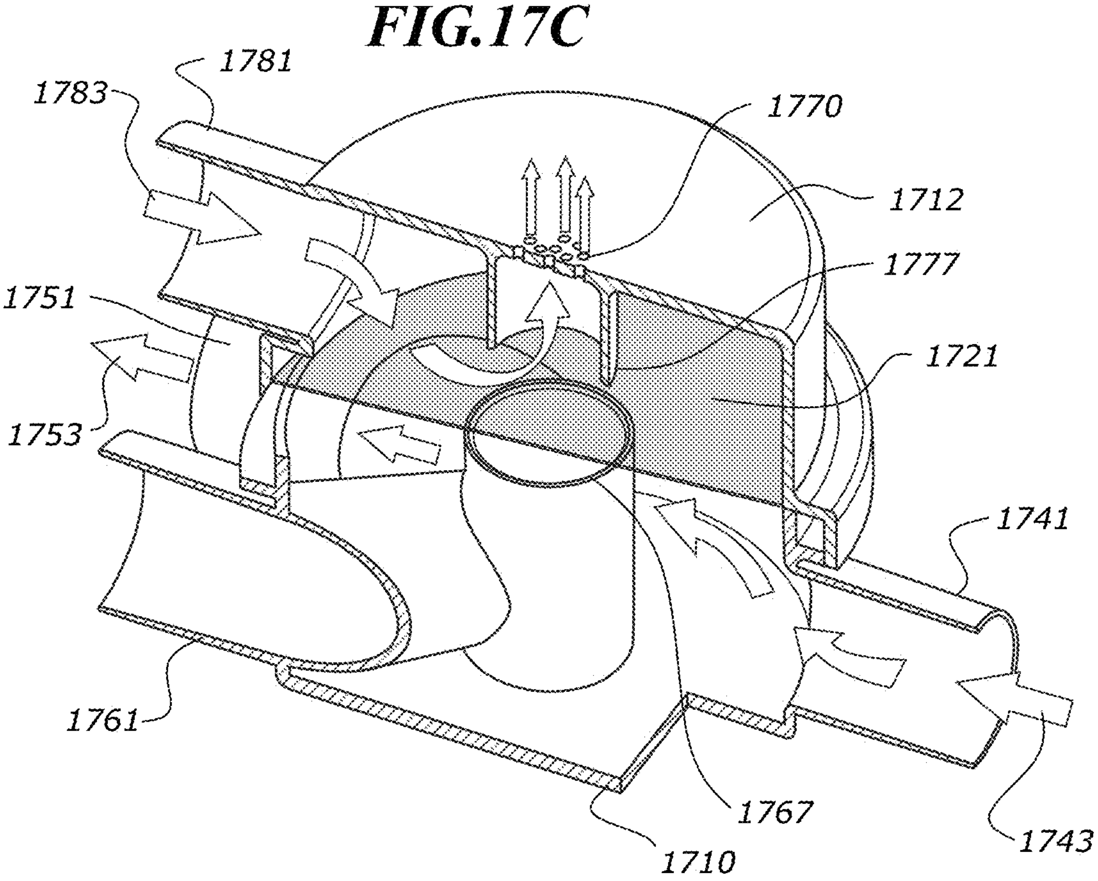
Figure 17E:
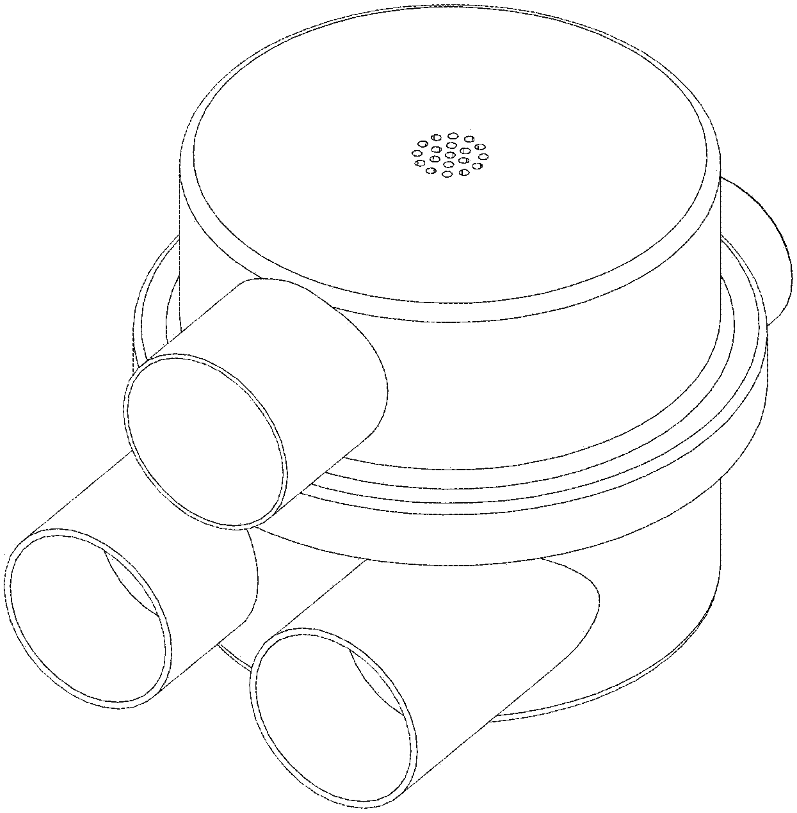

During exhalation, e.g., shown in FIGS. 17C-17D, the patient's expiration of gases increases the pressure within the breathing chamber of the patient interface relative to the gas flow from the ventilator. This is communicated to the control assembly 1720 through the pressure feedback port 1781 and causes the pressure in the control assembly upper body 1712, above the diaphragm 1721, to increase relative to the pressure below the diaphragm. When this occurs, the diaphragm 1721 may close (either partially or substantially), as discussed herein, and gases received from a ventilator are blocked or restricted from passing through the primary flow path and a substantial portion of the gas pass through the flushing flow path and out of the flushing flow port 1751 (as discussed herein, the gases passing through the flushing flow path may be accelerated such that upon release from the nasal prongs they may advantageously flush at least one of an anatomical dead space and an apparatus dead space). At the same time, movement of the diaphragm towards closure or restriction of flow through the primary flow path also results in the upper side of the diaphragm 1721 moving away from the exhaust vent sealing surface 1777, opening he venting flow path and enabling the exhaled air received from the patient interface through the pressure feedback port 1781 to vent to the atmosphere out of the exhaust vent 1770 such that dead space flushing occurs while the patients exhaled breath is vented to atmosphere.

The control assembly housing 1708 comprises two bodies, each of which comprise a cylindrically shaped structure closed at one end and with one end open. The two open ends of the bodies are configured to interact with each other such that they are connected to create a cavity between them that defines the control assembly housing 1708. The control assembly upper body 1712 comprises an internal protrusion extending from the closed end. The internal protrusion is open at one end and at the opposed end, a plurality of orifices is provided that extend through the housing. In use, the plurality of orifices provide an exhaust vent 1770. A cylindrical external projection projects from the sidewall of the housing and defines an inlet port to allow flow into the control assembly upper body 1712.

The control assembly lower body 1710 comprises three external cylindrical projections projecting from the sidewall of the lower body of the housing. Two of the external projections are located next to each other on one side of the housing, with the third external projection located on the opposite side of the control assembly lower body 1710. The separately located external projection defines an inlet flow port 1741 and is in fluid communication with the internal cavity of the control assembly housing 1708. Of the other two external projections, one defines the flushing flow port 1751. The third external projection is configured to extend through the sidewall of the control assembly housing 1708 and intersect an internal cylindrical protrusion extending upwardly from the closed end of the lower body such that a flow path is defined from inside the housing, down the internal protrusion that extends upwardly from the closed end of the control assembly lower body 1710 and along the external projection extending through the sidewall of the control assembly lower body 1710.

The control assembly 1720 further comprises a diaphragm 1721 that is located at or near the junction between the control assembly upper body 1712 and control assembly lower body 1710 of the control assembly 1720. The diaphragm 1721 may be sandwiched between the control assembly upper body 1712 and control assembly lower body 1710 of the control assembly 1720.

Both the exhaust flow path and primary flow path 1760 are configured to be directly affected by operation of the diaphragm 1721 within the control assembly 1720. The internal protrusion extending up from the closed end of the control assembly lower body 1710 has rim that provides a scaling surface (e.g., primary flow sealing surface 1767) at one end and an outlet at the other. When the diaphragm 1721 is deformed towards the sealing surface 1767 of the internal protrusion of the control assembly lower body 1710, flow through the primary flow path 1760 is restricted. The exhaust flow path comprises the internal protrusion extending downwardly from the closed end of the control assembly upper body 1712. The internal protrusion has a rim defining a sealing surface at one end. When the diaphragm 1721 is deformed towards the sealing surface 1777 of the internal protrusion of the control assembly upper body 1712, flow through the exhaust flow path is restricted.

The diaphragm 1721 is configured to be movable between two extreme positions. In one position the diaphragm 1721 is deformed such that it contacts the scaling surface of the primary flow path 1767 and substantially occludes flow through the primary flow path 1760 enabling unimpeded flow from the mask through the exhaust flow path and out to atmosphere. In the second position the diaphragm 1721 is configured to contact the sealing surface 1777 of the exhaust flow path and substantially occlude flow through the exhaust flow path while allowing unimpeded flow through the primary flow path 1760.

FIGS. 18A-18C and 19A-19B illustrate an embodiment of a control assembly 1820 that may form part of various noninvasive ventilation systems disclosed herein, e.g., the noninvasive ventilation system 1600 shown in FIG. 16. The control assembly 1820 of FIGS. 18A-18C and 19A-19B includes various components that may be substantially similar to components of the control assembly 1720 of FIGS. 17A-17D and/or the control assembly 1100 of FIGS. 11A-11B. For example, the ventilator port 1841 may correspond to the inlet flow port 1741, the primary flow port 1861 may correspond to the primary flow port 1761, the flushing flow port 1851 may correspond to the flushing flow port 1751, the pressure feedback port 1881 may correspond to the pressure feedback port 1781, and the exhaust vent 1870 may correspond to the exhaust vent 1770. While some components may be similar, substantially similar, or even identical in structure and/or function between the control assembly 1820 and the control assembly 1720, none are required to be similar, substantially similar, or identical.

The control assembly 1820 includes a ventilator port 1841 that is configured to accept gas flow 1843 from a gas source. Like other control assemblies discussed herein, the control assembly 1820 is configured to divert, split, or bifurcate the gas flow 1843 into one or both of a primary flow path, which leaves the control assembly 1820 through the primary flow port 1861, and a flushing flow path, which leaves the control assembly 1820 through the flushing flow port 1851. The flushing flow path may be continuously open and not directly affected by the operation of the control assembly. The primary flow path may be more or less restricted by the control assembly 1820 (which may define an inlet, beginning, or opening to the primary flow path). As discussed elsewhere, the flushing flow path may have a higher resistance to flow than the primary flow path. Consequently, when the primary flow path is less restricted by the control assembly 1820, the gas flow 1843 may preferentially flow, e.g., a substantial portion of the volume of gas will flow, through the primary flow path and out of the primary flow port 1861 (in this case, only a volume of gas will flow through the flushing flow path). Gases that do not flow through the primary flow path are diverted to the flushing flow path and exit the control assembly 1820 through the flushing flow port 1851. Therefore, when the primary flow path is being restricted by the control assembly 1820, a comparatively larger volume of the gas flow 1843 will pass through the flushing flow path and out of the flushing flow port 1851 (though, the control assembly 1820 generally does not completely seal the primary flow path and, even when restricting the primary flow path, allows some volume of gas to pass through the primary flow path and out of the primary flow port 1861).

The control assembly 1820 includes a control assembly body 1810 that generally provides structure for the rest of the device. On one side, e.g., the top, of the control assembly body 1810 is a control assembly upper cap 1812 and on the other side, e.g., the bottom, is a control assembly lower cap 1813. Between the control assembly body 1810 and the control assembly upper cap 1812 is an upper diaphragm 1821. Between the control assembly body 1810 and the control assembly lower cap 1813 is a lower diaphragm 1822. The control assembly 1720 discussed in connection with FIGS. 17A-17D relies on the pressures on the upper and lower sides of its diaphragm 1721, e.g., the patient side and the gas source side of the diaphragm 1721, respectively, to increase and/or decrease the restriction of its primary flow path. The control assembly 1820 may not rely on the pressure between the upper diaphragm 1821 and the control assembly upper cap 1812 or the pressure between the lower diaphragm 1822 and the control assembly lower cap 1813. Therefore, the volume between the upper diaphragm 1821 and the control assembly upper cap 1812 and the volume between the lower diaphragm 1822 and the control assembly lower cap 1813 may be in fluid communication with the atmosphere. In some embodiments, the volume between the upper diaphragm 1821 and the control assembly upper cap 1812 and the volume between the lower diaphragm 1822 and the control assembly lower cap 1813 may be enclosed and operate, at least partially, in conjunction with one or more pressure port lines.

The upper diaphragm 1821 is configured to rise off of the primary flow path sealing surface 1867 which defines the opening to the primary flow path. The upper diaphragm 1821 has a flow restricting position and a flow permitting position. When the upper diaphragm 1821 is in its flow restricting position, the lower side of the upper diaphragm 1821 approaches or nears the primary flow path sealing surface 1867 and restricts gases from flowing through the opening of primary flow path (e.g., when the upper diaphragm 1821 nears the primary flow path sealing surface 1867 and restricts the primary flow path, a comparatively higher volume of gases are forced through the flushing flow path and out of the flushing flow port 1851). When the upper diaphragm 1821 is in its less restricting or flow permitting position, the lower side of the upper diaphragm 1821 lifts off the primary flow path sealing surface 1867 and allows gases to pass between the primary flow path sealing surface 1867 and the upper diaphragm 1821, thereby allowing gases to flow through the opening to the primary flow path and out of the control assembly 1820 via the primary flow port 1861.

When unrestricted by the control assembly 1820, the primary flow path through the control assembly 1820 may have a much lower restriction to flow than the flushing flow path through the control assembly 1820. Therefore, when the upper diaphragm 1821 is in its less restricting or flow permitting position, a substantial portion of the volume of gases entering the ventilator port 1841 will pass through the primary flow path and exit via the primary flow port 1861. When the upper diaphragm 1821 restricts the primary flow path, the volume of gases that pass through the primary flow path is decreased and the volume of gases that pass through the flushing flow path is increased.

The lower diaphragm 1822 has a less restricting or flow permitting position and a restricting position. When the lower diaphragm 1822 is in its restricting position, the upper side of the lower diaphragm 1822 approaches or nears the exhaust conduit scaling surface 1877 and restricts gases from flowing through the pressure feedback port 1881 and out of the exhaust vent 1870. When the lower diaphragm 1822 is in its less restricting or flow permitting position, the upper side of the lower diaphragm 1822 moves away from the exhaust conduit sealing surface 1877 and allows gases to travel from the pressure feedback port 1881, between the exhaust conduit sealing surface 1877 and the lower diaphragm 1822, and out of the exhaust vent 1870.

The upper diaphragm 1821 may be connected to the lower diaphragm 1822 by the diaphragm connector 1823. The diaphragm connector 1823 may be a connector with a substantially fixed length, e.g., the diaphragm connector 1823 may have little or no compliance or elasticity. The diaphragm connector 1823 may have a length such that when the lower diaphragm 1822 is in its flow permitting or less restricting position, the diaphragm connector 1823 forces the upper diaphragm 1821 into its restricting position (e.g., as the lower diaphragm 1822 goes down, e.g., moves away from the exhaust conduit scaling surface 1877, the diaphragm connector 1823 pulls down on the upper diaphragm 1821, restricting the primary flow path). The diaphragm connector 1823 may have a length such that when the upper diaphragm 1821 is in its flow permitting or less restricting position, the diaphragm connector 1823 forces the lower diaphragm 1822 into its restricting position (e.g., as the upper diaphragm 1821 goes up, e.g., moves away from the primary flow path sealing surface 1867, the diaphragm connector 1823 pulls up on the lower diaphragm 1822, restricting the flow between the pressure feedback port 1881 and the exhaust vent 1870.

The control assembly 1820 includes a pressure feedback port 1881 that guides gases from a breathing chamber of a patient interface into the control assembly 1820, above the lower diaphragm 1822. The pressure feedback port 1881 may be configured to accept a feedback gas flow 1883, which may include gases exhaled by the patient (e.g., the patient interface connected to the control assembly 1820 may be sealingly attached to the patient's face and configured such that most or all of the gases exhaled into the patient interface are guided via a conduit to the pressure feedback port 1881 as feedback gas flow 1883). Pressure changes in the portions of the control assembly body 1810 that are connected to the pressure feedback port 1881 (above the lower diaphragm 1822) (e.g., due to fluid (e.g., pressure) communication between the control assembly body 1810 and the breathing chamber of a patient interface via the pressure feedback port 1881) may cause the lower diaphragm 1822 (and, because of the diaphragm connector 1823, the upper diaphragm 1821) to move towards or away from the exhaust vent sealing ring 1877 to increase or decrease, respectively, restriction of the flow from the pressure feedback port 1881 and out of the exhaust vent 1870.

Figure 18A:
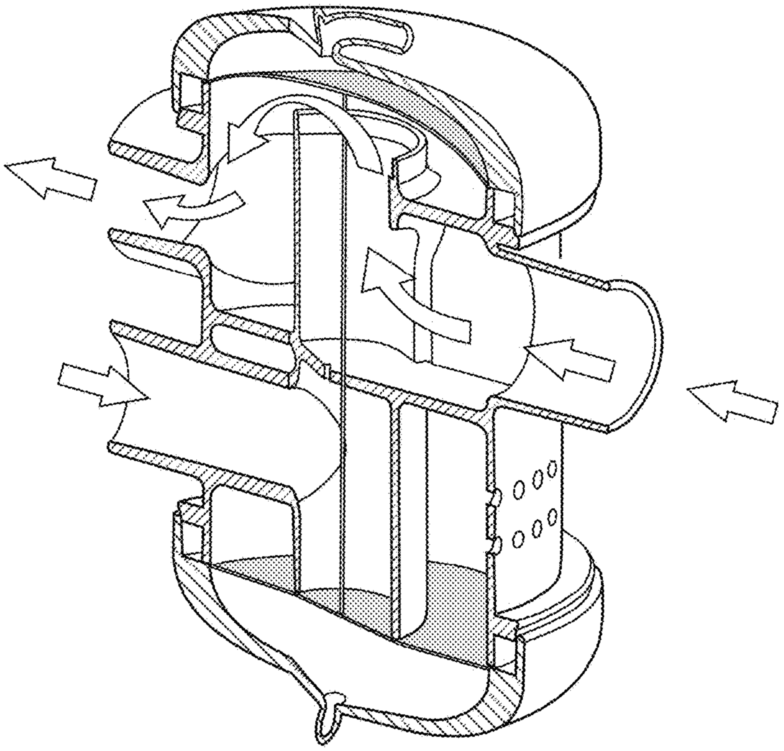
FIGS. 18A-18B show various cross-sectional views of an embodiment of a control assembly.

The exhaust vent 1870 may vent air exhaled by a patient and received from the patient interface via the pressure feedback port 1881. The lower diaphragm 1822 is configured to move towards and away from the exhaust conduit sealing surface 1877 to increase and decrease restriction to flow of gas from the pressure feedback port 1881 out of the exhaust vent 1870. As shown in FIGS. 18A, when the upper diaphragm 1821 is in its least restricting position (e.g., allowing gas to travel substantially unrestricted through the primary flow path and out of the primary flow port 1861), the lower diaphragm 1822 is raised up toward the exhaust conduit sealing surface 1877. When the lower diaphragm 1822 is moved toward the exhaust conduit sealing surface 1877, gases received through the pressure feedback port 1881, e.g., exhalation gases, are restricted (e.g., substantially restricted) from venting out of the exhaust vent 1870 (e.g., only a comparatively small volume of gases are permitted to vent). As the upper diaphragm 1821 moves toward the primary flow path sealing surface 1867 and restricts the primary flow path, the lower diaphragm 1822 moves away from the exhaust conduit sealing surface 1877. As the lower diaphragm 1822 moves away from the exhaust conduit sealing surface 1877, the flow of gases from the pressure feedback port is less restricted, allowing gases received through the pressure feedback port 1881 to leave the control assembly 1820 through the exhaust vent 1870. In this way, the control assembly 1820 may be responsive, e.g., dynamically responsive, to pressures generated by the patient during respiration.

Figure 19A:
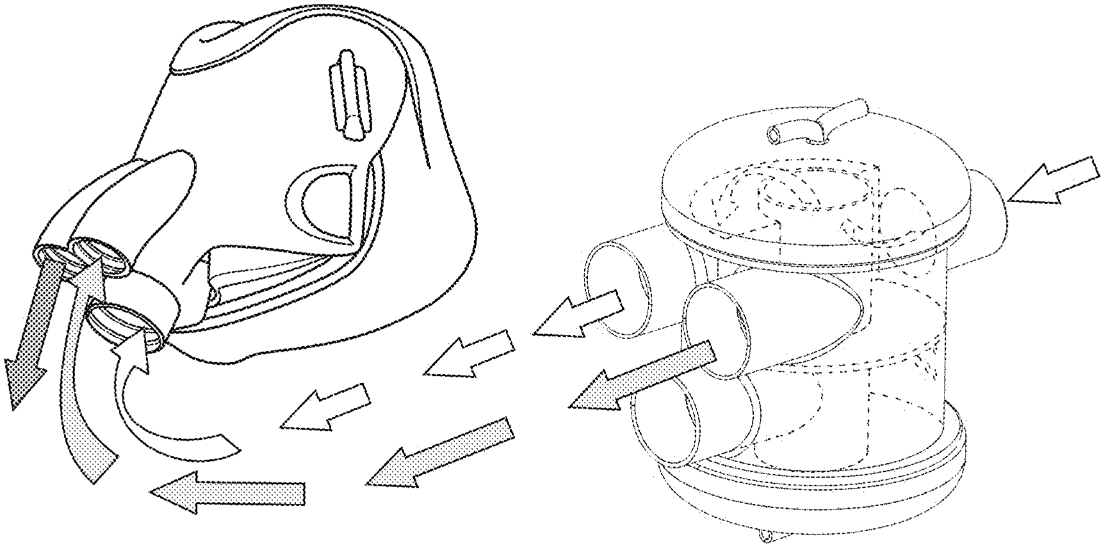
FIGS. 19A-19B schematically show the control assembly of FIGS. 18A-18C during operation (with internal parts shown in phantom outline).

During inhalation, e.g., shown in FIGS. 18A and 19A, the patient's inspiration of gases removes mass from the fixed volume of gas within the breathing chamber of the patient interface and causes the pressure in the patient interface to decrease. Decreased pressure in the breathing chamber of the patient interface is communicated to the control assembly 1820 through the pressure feedback port 1881 and causes the pressure in the control assembly body 1810 above the lower diaphragm 1822, to drop. When the pressure above the lower diaphragm 1822 drops, the lower diaphragm 1822 may move toward the exhaust vent scaling ring 1877, as discussed herein. When the lower diaphragm 1822 moves toward the exhaust vent scaling ring 1877, it pushes upward on the diaphragm connector 1823, which, in turn, pushes up on the upper diaphragm 1821, thereby biasing the upper diaphragm 1821 upward and into its less restricting or flow permitting position and gases received from a gas source via the port 1841 are allowed to pass through the primary flow path, out of the primary flow port 1861 and to the patient interface (as discussed herein, gases may flow preferentially through the open primary flow port 1861, rather than the open flushing flow port 1851, due to the comparatively lower resistance to flow of the primary flow path versus the flushing flow path). When the lower diaphragm 1822 is in its most restricting position (and the upper diaphragm 1821 is in its least restricting position), the upper side of the lower diaphragm 1822 is moved towards the exhaust conduit sealing surface 1877, thereby decreasing inflow of atmospheric air, which could increase the pressure in the pressure feedback port 1881 and allow the upper diaphragm 1821 to prematurely seal.

Figure 18B:
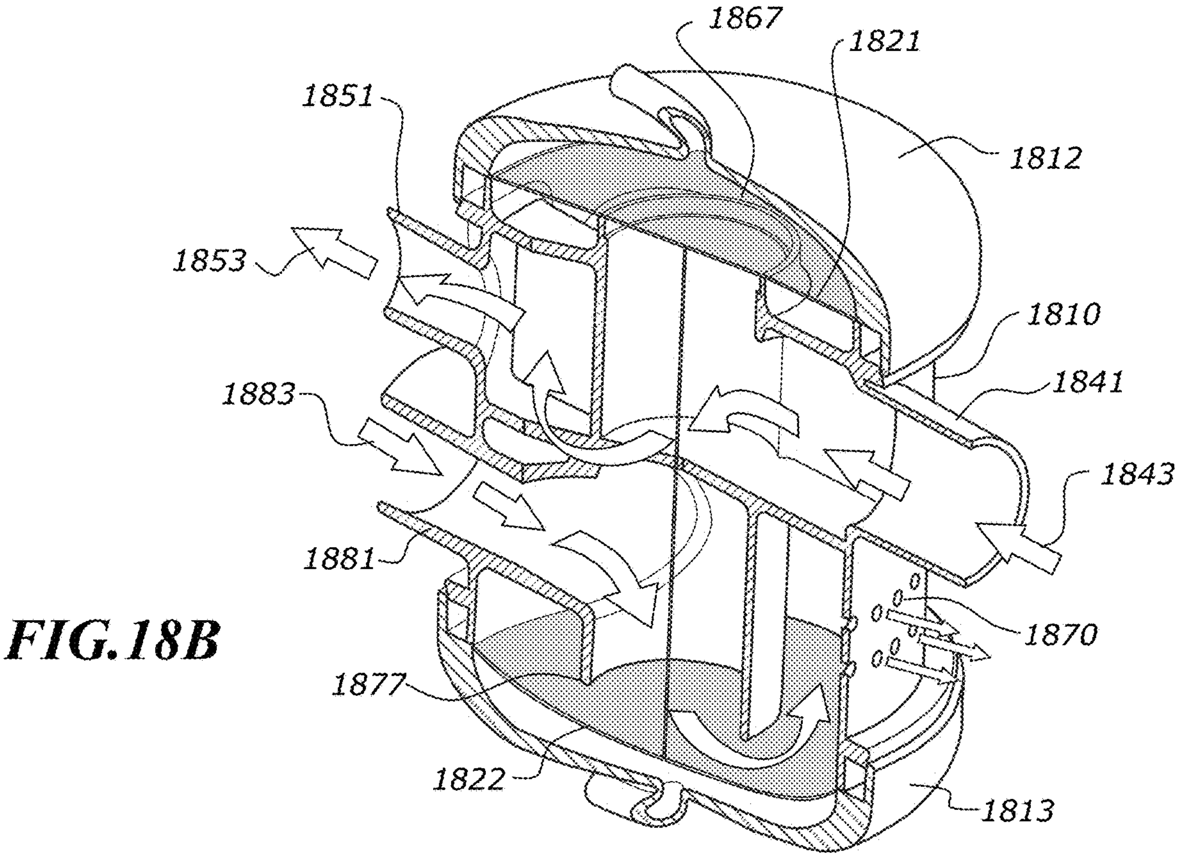
Figure 18C:
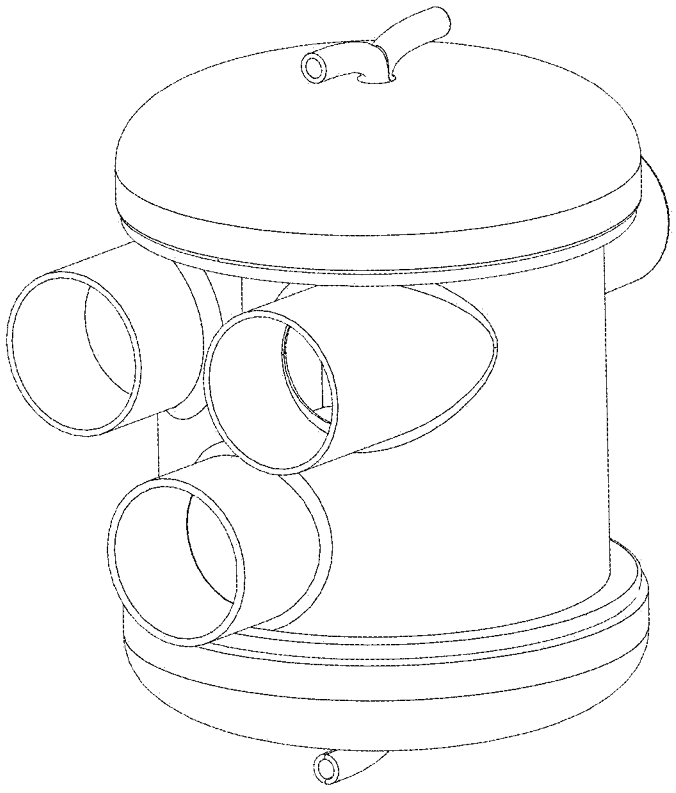
FIG. 18C shows a ghost view of the control assembly.
Figure 19B:
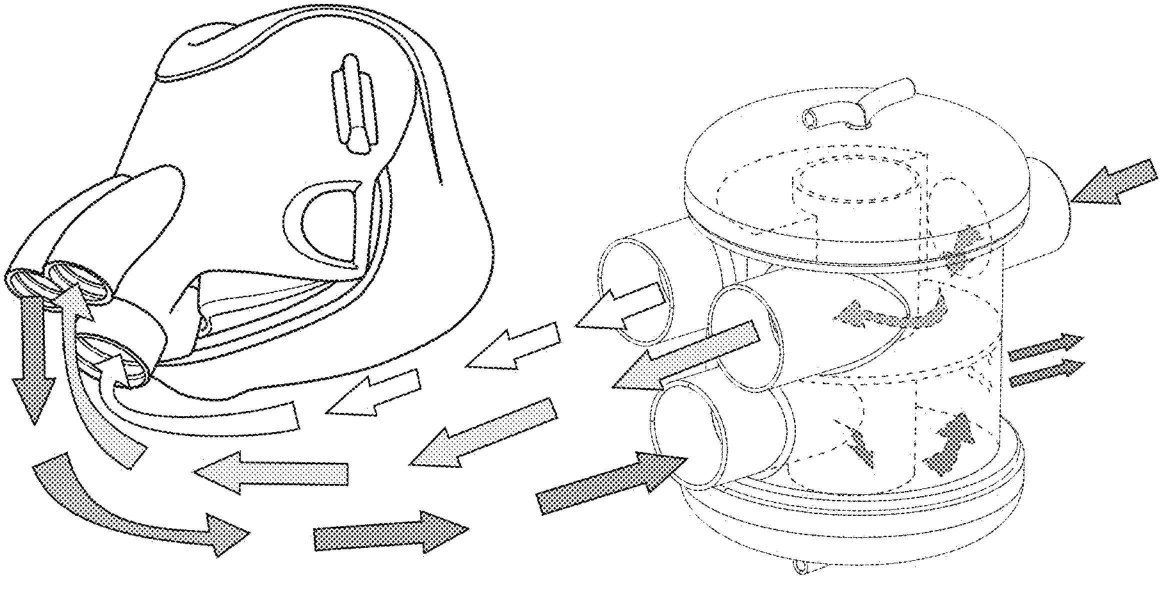

During exhalation, e.g., shown in FIGS. 18B & 19B, the patient's expiration of gases adds additional gases to the fixed volume of the breathing chamber of the patient interface and increases the pressure within the breathing chamber. Increased pressure in the breathing chamber of the patient interface is communicated to the control assembly 1820 through the pressure feedback port 1881 and causes the pressure in the control assembly body 1810 above the lower diaphragm 1822, to increase. When the pressure above the lower diaphragm 1822 increases (e.g., first in the pressure feedback port 1881), the lower diaphragm 1822 moves away from the exhaust vent sealing ring 1877, thereby pulling down on both the diaphragm connector 1823 and the upper diaphragm 1821 drawing the upper diaphragm 1821 closer to the primary flow path sealing surface 1867. As the upper diaphragm 1821 moves toward the primary flow path sealing surface 1867, gases received from the gas source are restricted from passing through the primary flow path and are forced to pass through the flushing flow path and out of the flushing flow port 1851 to reach the patient interface (as discussed herein, the gases passing through the flushing flow path may be accelerated such that upon release in the patient interface they may flush at least one of an anatomical dead space and an apparatus dead space). As the lower diaphragm 1822 moves away from the exhaust vent sealing ring 1877, gases are allowed to more freely pass from the pressure feedback port 1881, past the lower diaphragm 1822, and out of the exhaust vent 1870. In this way, the control assembly 1820 may passively vent gases expired by the patient during exhalation.

Figure 20A:
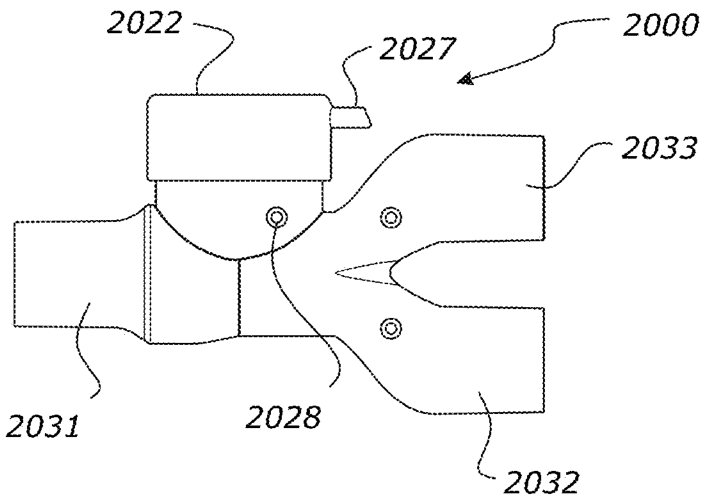
FIGS. 20A-20C show various views of another embodiment of a control assembly.
Figure 20B:
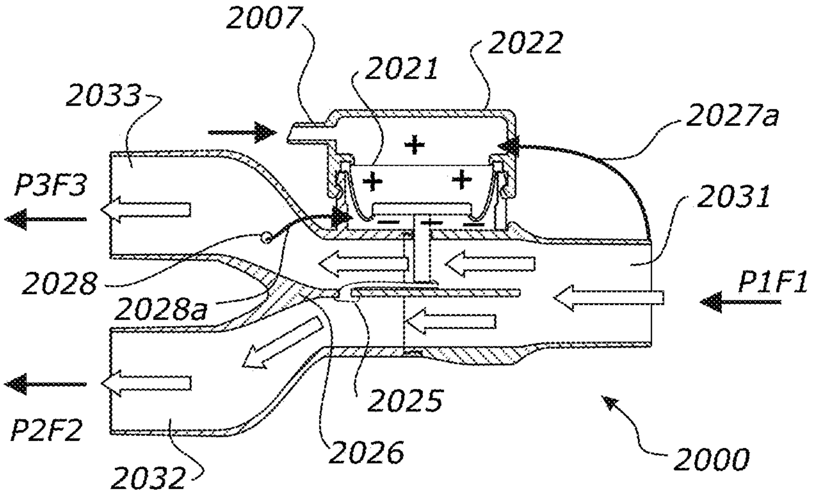
Figure 20C:
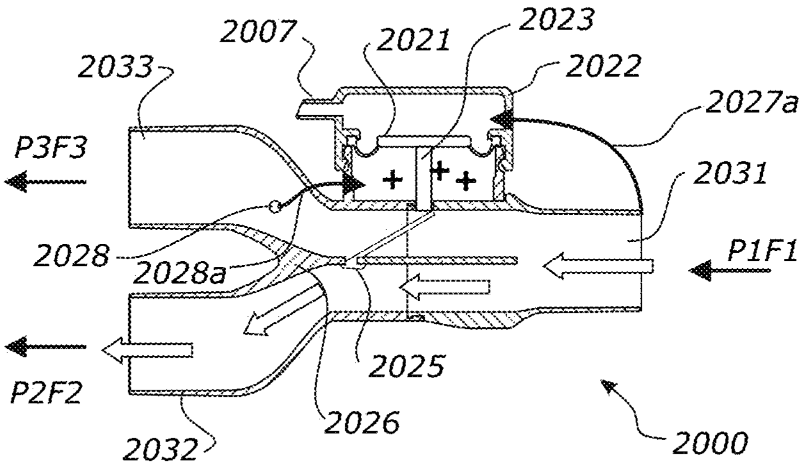

FIGS. 20A-20C show various views of another embodiment of a control assembly. FIG. 20A shows the control assembly in side view. FIG. 20B illustrates the control assembly in longitudinal cross-section and in a first operational state. FIG. 20C illustrates the control assembly in longitudinal cross-section and in a second operational state. In this embodiment the movable member of the control assembly 2000 comprises a flap valve 2024 that is coupled to a diaphragm 2021 that is configured to move the flap valve to modulate the primary and flushing gas flows.

The control assembly 2000 comprises a housing with internal gas flow porting, which bifurcates from a gas source port 2031 to a primary flow port 2032 and a flushing flow port 2033. Arrows P1F1, P2F2, and P3F3 in FIGS. 20B and 20C indicate the source gas flow, flushing flow, and primary gas flow respectively. The resiliently flexible diaphragm 2021 is held by its peripheral edge in a diaphragm chamber 2022 of the control assembly. A first gas pressure feedback port 2027 is provided into the diaphragm chamber 2022 on one side of the diaphragm. The first gas pressure feedback port 2027 is coupled in use to receive gas source pressure, as schematically indicated by arrow 2027*a* in FIGS. 20B and 20C. A second gas pressure feedback port 2028 is provided into the diaphragm chamber 2022 on the opposite side of the diaphragm. The second gas pressure feedback port 2028 is coupled in use to receive gas pressure indicative of the pressure in a patient interface as schematically indicated by arrow 2028*a* in FIGS. 20B and 20C. The pressure in the patient interface varies with and is indicative of whether the patient wearing the interface is inhaling or exhaling.

A connector 2023 is connected at one end to the diaphragm 2021 so that the connector 2023 moves with movement of the diaphragm. The connector 2023 engages, at an opposite end, to a flap valve 2024. The connector 2023 may or may not be permanently connected to the flap valve. The flap valve is positioned within the interior of the control assembly in the primary flow path. The flap valve is mounted for pivotal movement about a pivot or hinge point 2025. The flap valve 2024 may for example be attached to an internal wall 2026 within the control assembly which divides an interior of the control assembly into the primary and flushing gas flow paths. The flap valve may be attached to the internal wall 2026 by a living hinge for example, at 2025. The diaphragm 2021 and flap valve 2024 may move between the first operational state shown in FIG. 20B in which the flap valve 2024 allows maximum primary gas flow, and thus flushing gas flow is at a relative minimum, and the second operational state shown in FIG. 20C in which the flap valve 2024 closes (or substantially restricts) primary gas flow, and thus flushing gas flow is at a maximum, or any intermediate position between.

In operation, the diaphragm 2021 moves the flap valve 2024 between these two states. On patient inhalation, pressure on the gas source side of the diaphragm 2021 is higher than pressure on the opposite, patient side of the diaphragm, causing the diaphragm to move thus moving the linked flap valve 2024 to open the primary gas flow port 2033 maximally to the gas source, and relatively reduce flushing gas flow. On patient exhalation, breathe out pressure from the patient on the patient side of the diaphragm 2021 is higher than pressure on the gas source side of the diaphragm, causing the diaphragm to move thus moving the linked flap valve 2024 to restrict gas flow through the primary gas flow port 2033 from the gas source, and increase gas flow through the flushing gas flow port 2032. Thus, in use and as in other embodiments, the control assembly operates dynamically in response to patient inspiration and exhalation, to modulate the flushing and primary gas flows. In this embodiment the control assembly is configured to bias flow towards the flushing flow path on exhalation, but need not be i.e. could be non-biased. In earlier described and other embodiments the control assembly may or may not also be configured to bias flow towards the flushing flow path on exhalation.

Figure 21A:
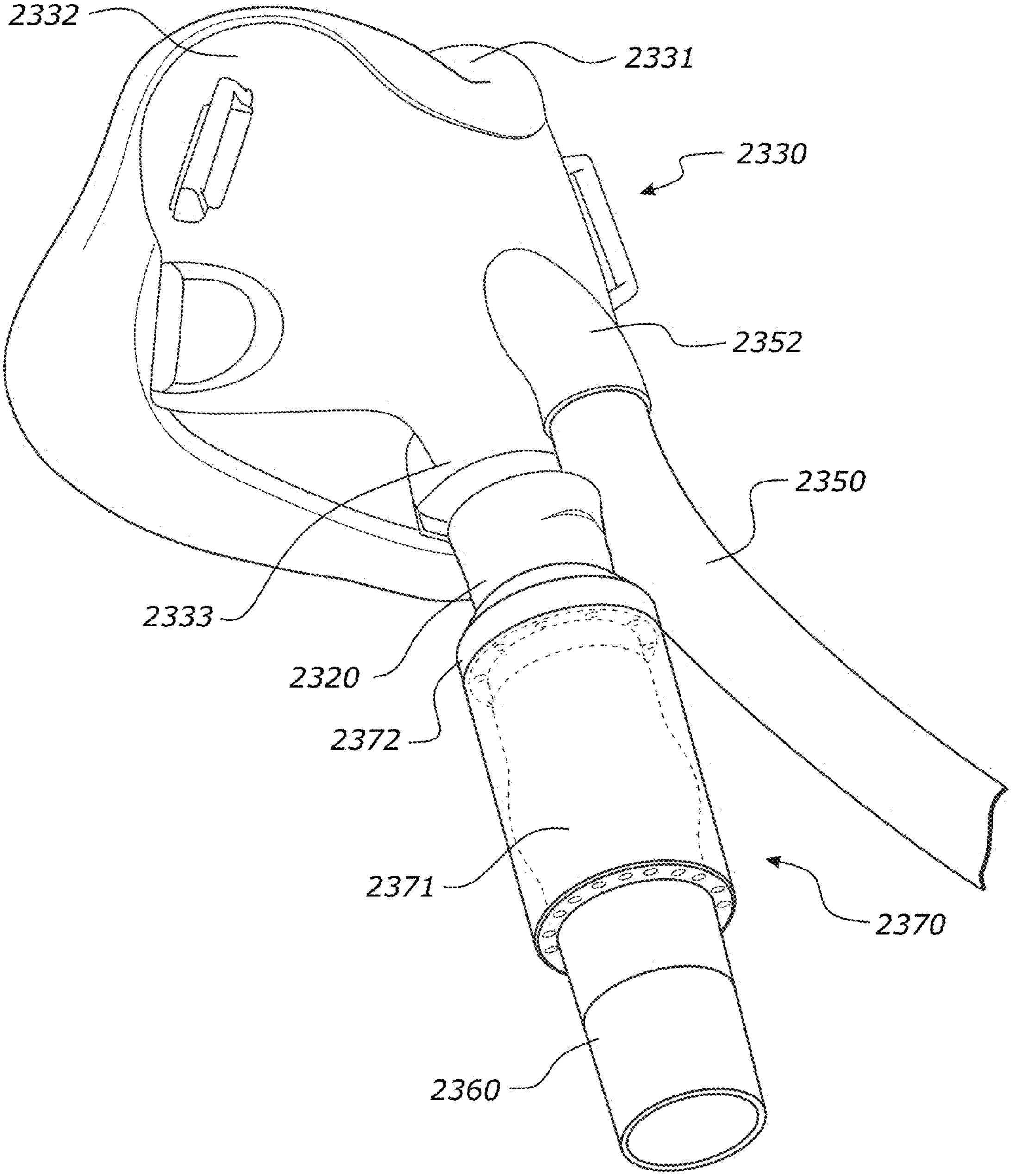
FIG. 21A shows a patient interface incorporating an embodiment of an exhaust vent (with internal parts shown in phantom outline).
Figure 21B:
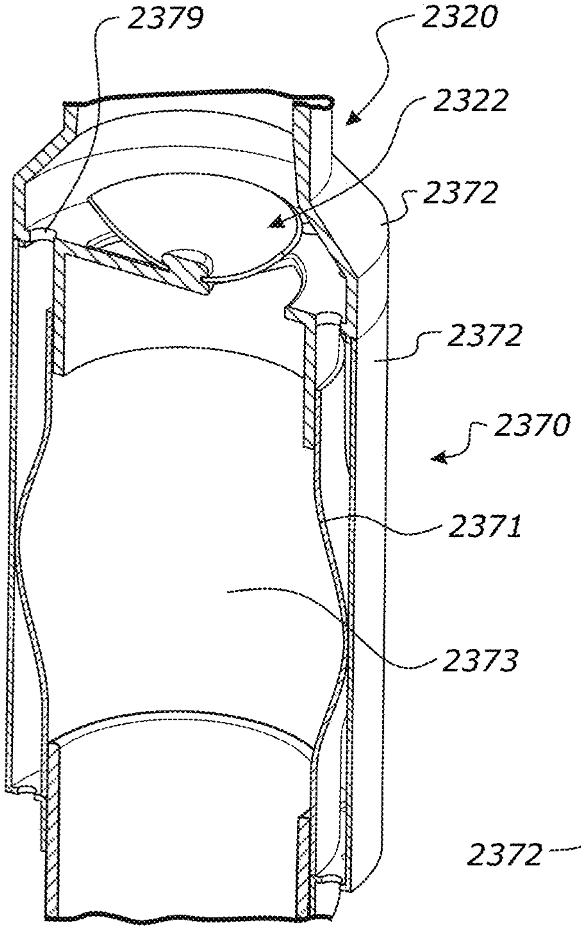
FIGS. 21B and 21C show longitudinal cross-section views and FIGS. 21D and 21E show schematic longitudinal cross-section views of the exhaust vent of FIG. 21A, in different operational states.
Figure 21C:
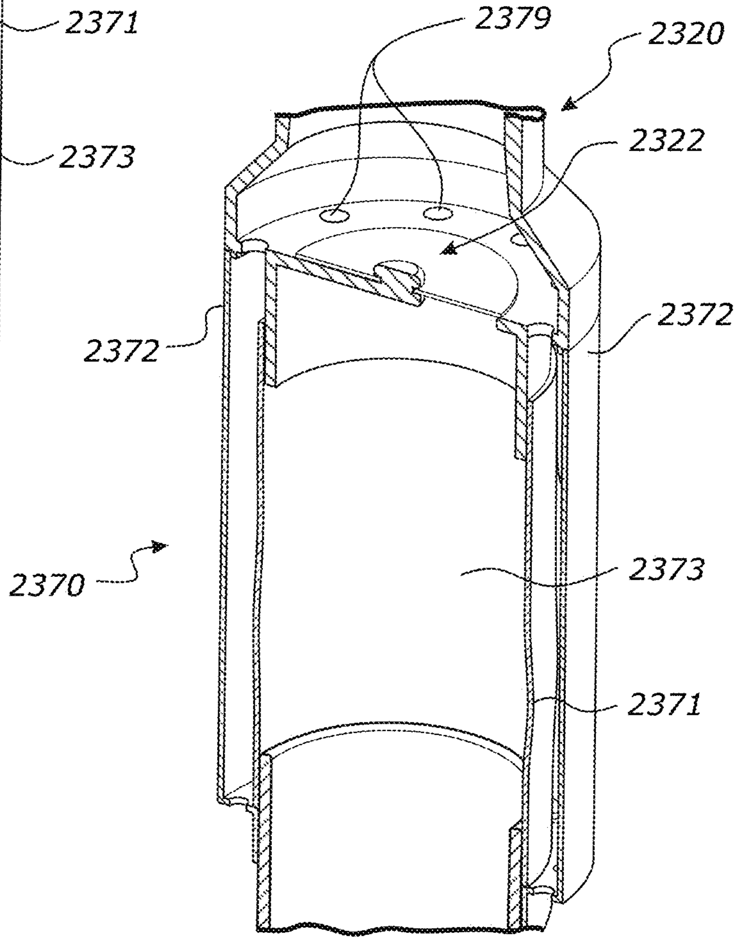
Figure 21D:
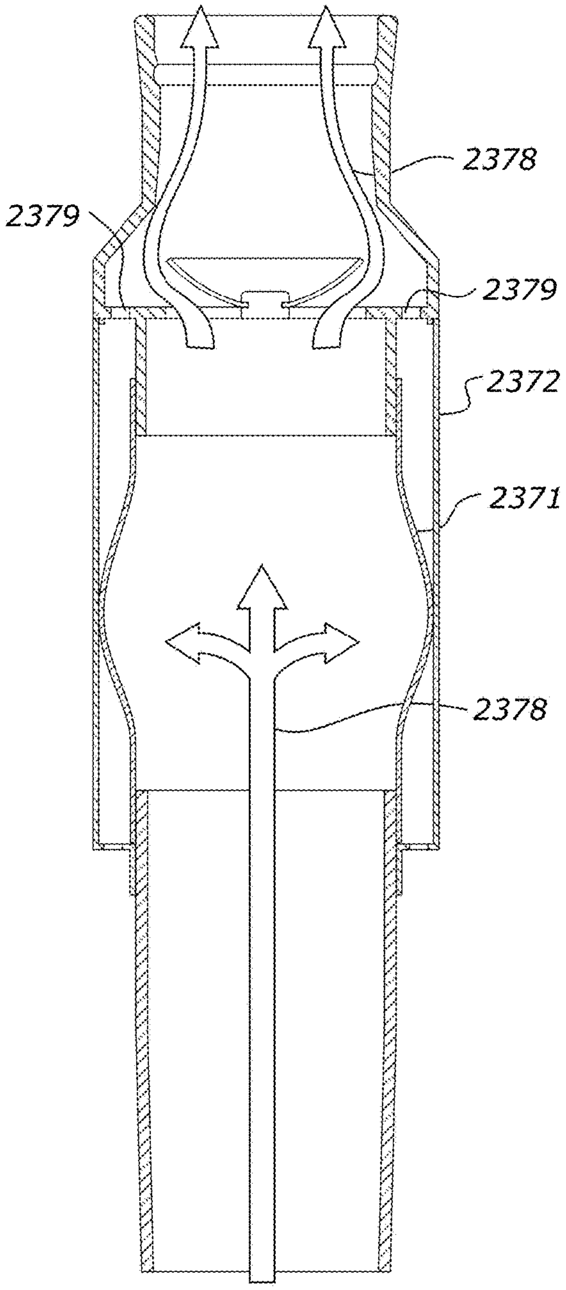
Figure 21E:
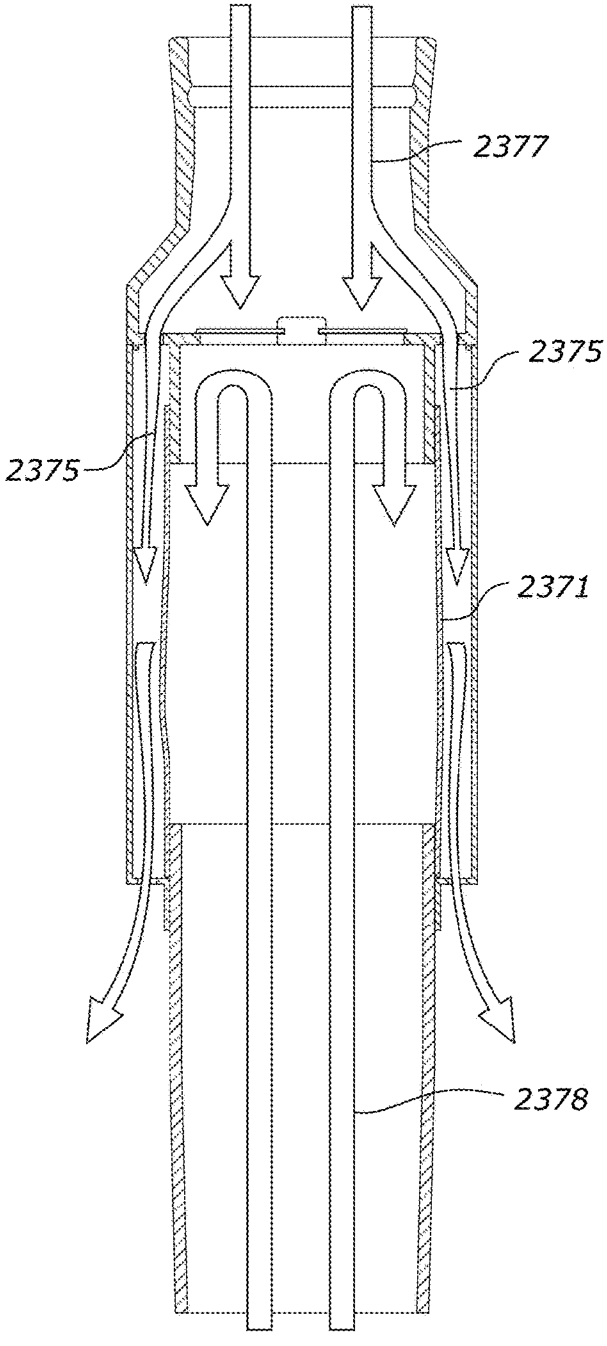

FIG. 21A shows a patient interface incorporating an embodiment of a one way valve as an exhaust vent. FIGS. 21B and 21C show longitudinal cross-section views and FIGS. 21D and 21E show schematic longitudinal cross-section views, of the exhaust vent of FIG. 21, in different operational states. The patient interface indicated at 2330, may comprise a mask body 2332 and a mask cushion 2331 which together define a breathing chamber of the patient interface. The patient interface may be in any of the forms described herein in relation to FIGS. 3-7, 9,10,14 and 15 or in any other form. In the embodiment shown in FIG. 21A the interface comprises a flushing flow path 2350 comprising a conduit which is connected via a nasal elbow fitting 2352 to the mask body 2332, and may for example terminate in one or more nasal cannula or prongs (not shown in FIG. 21A but as described previously in relation to for example FIG. 3) or any other structure which directs air flow to the nasal openings of the patient. The interface comprises a primary flow path 2360 comprising a conduit which couples to the mask body 2332 via coupling portion 2333. A control assembly 2320 as in the embodiment of FIG. 3 is contained in-line with the primary flow path 2360. In other embodiments the control assembly may be in any other form described, and/or a single conduit may supply the interface from a gas source and the primary and flushing flow paths may divide within the interface or at their entry to the interface. In yet other embodiments the interface which may be in any form such as described above, may not provide both primary and flushing gas flows to the patient but a single flow of respiratory gas, in an NIV or CPAP or other respiratory application.

The patient interface 2320 comprises a one way valve system as an exhaust valve 2370 comprising an expanding exhaust gas flow control element 2371. In the embodiment shown the exhaust valve 2370 is provided in the primary flow path conduit 2360 below coupling portion 2333 and control assembly 2320. The exhaust valve 2370 comprises an exhaust valve body 2372 having a hollow interior defining an internal through passage, and housing expanding exhaust gas flow control element 2371. The flow control element 2371 also comprises a hollow interior defining an internal through passage 2373, which permits primary gas flow through the flow control element 2371 and thus exhaust valve.

An exhaust gas flow space 2374 is defined between the exterior of the flow control element 2371 and an interior of the exhaust valve body 2372—see especially FIG. 21C which shows the flow control element 2371 in an unexpanded state. When the flow control element 2371 is unexpanded, as shown in FIG. 21C, an exhaust gas flow path is defined around and through a space between the exterior of the expanding flow control element 2321 and the interior of the exhaust valve body 2372, as indicated by arrows 2375 in FIG. 21E. In the embodiment shown this occurs under exhalation gas pressure from the patient against the pressure of the primary flow pressure, when also the control assembly umbrella flap valve member 2322 closes (or restricts) the primary flow 2378 to the interface from the gas source the patient exhalation pressure. In FIG. 21E arrows 2378 indicate the primary gas flow. Apertures 2379 into this space comprise the exhaust vent. Conversely under inhalation gas pressure from the patient, when also the control assembly umbrella flap valve member 2322 opens allowing primary flow to the interface from the gas source, then in the absence of patient exhalation gas pressure around the exterior of the flow control element 2321, the flow control element 2321 which is formed of a resiliently elastic or deformable material, expands against the interior of the exhaust valve body 2372 as shown in FIG. 21B. This closes the exhaust flow path between the exterior of the expanding flow control element 2321 and the interior of the exhaust valve body 2372, as also shown in FIG. 21E. In use the exhaust valve operates dynamically in response to patient inspiration and exhalation, closing or restricting flow under inspiration and opening under exhalation as described, to provide under exhalation a pathway to the external atmosphere for high $CO_2$ washout gases from within the patient interface but closing this pathway under inhalation.

In the embodiment described the exhaust valve 2370 is incorporated in a conduit adapted to be coupled to a patient interface, and in particular in the interface end of a lead up conduit used with the interface. Alternatively the exhaust valve 2370 in the form shown or any other form can be incorporated in a patient interface. For example the exhaust valve can be incorporated in a frame part of the interface which supports a cushion or seal, for example interface body 2332. The exhaust valve can be incorporated in an elbow connection of the interface. The exhaust valve can be incorporated in a short gas flow conduit permanently or removably attached to a frame part of the interface.

The foregoing description and examples have been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

The term 'restrict' in relation to a gas flow or a gas port can include to fully close or block the gas flow or a gas port where the context indicates, or where the context does not indicate otherwise, and 'restricting' and 'restriction' have a similar meaning.

Although systems and methods for improved ventilation including noninvasive ventilation have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for improved ventilation including noninvasive ventilation. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

What is claimed is:

1. A method for providing non-invasive ventilation to a patient, the method comprising:

providing positive pressure breathing gases to a patient through a patient interface apparatus comprising a sealing mask forming a seal with a mouth and a nose of the patient, an inlet that receives the positive pressure breathing gases from a pressurized gas flow source, and a gas outlet;

wherein:

during patient inhalation, the flow of gas is provided to the patient through one or more of the mouth and the nose of the patient; and during patient exhalation, a flow restrictor of the patient interface apparatus is configured to increase a portion of the positive pressure breathing gases along a flow path that provides anatomical dead space flushing through a nasal cavity of the patient and out through the gas outlet.

2. The method of claim 1, wherein the flow restrictor causes the increase in the portion of the positive pressure breathing gases along the flow path that provides anatomical dead space flushing based at least in part on an increase of pressure within the patient interface apparatus.

3. The method of claim 2, wherein the increase in pressure within the patient interface apparatus is further caused by exhalation of the patient.

4. The method of claim 2, wherein the flow path that provides anatomical dead space flushing comprises flow through a non-sealing cannula comprising two prongs positioned within a chamber that seals about the mouth and nose of the patient.

5. The method of claim 1, wherein the flow restrictor is configured to cause the increase in the portion of the positive pressure breathing gases along the flow path that provides anatomical dead space flushing during patient exhalation and to a start of patient inhalation.

6. The method of claim 1, wherein the flow path that provides anatomical dead space flushing comprises flow in through the nose of the patient, out through the mouth of the patient or out through the nose of the patient, and out through the gas outlet.

7. The method of claim 1, wherein the sealing mask comprises a non-sealing cannula comprising two prongs positioned within a chamber that seals about the mouth and nose of the patient.

8. The method of claim 7, wherein each of the two prongs is configured in size and shape to direct and/or accelerate at least a portion of the positive pressure breathing gases into nares of the patient.

9. The method of claim 1, wherein the gas outlet comprises a bias vent.

10. The method of claim 1, wherein the gas outlet is configured to connect to an expiratory limb.

11. The method of claim 1, wherein the positive pressure breathing gases are provided continuously.

* * * * *